US012673086B2

(12) United States Patent
DeRosa et al.

(10) Patent No.: US 12,673,086 B2
(45) Date of Patent: Jul. 7, 2026

(54) PROCESS AND FORMULATION OF LIPID NANOPARTICLES

(71) Applicant: TRANSLATE BIO, INC., Waltham, MA (US)

(72) Inventors: Frank DeRosa, Chelmsford, MA (US); Hardip R. Gopani, Acton, MA (US); Shrirang Karve, Acton, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 355 days.

(21) Appl. No.: 18/247,976

(22) PCT Filed: Oct. 6, 2021

(86) PCT No.: PCT/US2021/053776
§ 371 (c)(1),
(2) Date: Apr. 5, 2023

(87) PCT Pub. No.: WO2022/076562
PCT Pub. Date: Apr. 14, 2022

(65) Prior Publication Data

US 2023/0372440 A1 Nov. 23, 2023

Related U.S. Application Data

(60) Provisional application No. 63/088,047, filed on Oct. 6, 2020.

(51) Int. Cl.

| | |
|---|---|
| ***A61K 38/17*** | (2006.01) |
| ***A61K 9/1272*** | (2025.01) |
| ***A61K 9/19*** | (2006.01) |
| ***A61K 47/18*** | (2017.01) |
| ***A61K 47/22*** | (2006.01) |
| ***A61K 47/26*** | (2006.01) |
| ***C12N 15/88*** | (2006.01) |

(52) U.S. Cl.
CPC ........ *A61K 38/1709* (2013.01); *A61K 9/1272* (2013.01); *A61K 9/19* (2013.01); *A61K 47/183* (2013.01); *A61K 47/22* (2013.01); *A61K 47/26* (2013.01); *C12N 15/88* (2013.01)

(58) Field of Classification Search
CPC .... A61K 38/1709; A61K 9/1272; A61K 9/19; A61K 47/183; A61K 47/22; A61K 47/26; C12N 15/88
See application file for complete search history.

(56) References Cited

U.S. PATENT DOCUMENTS

| | | | |
|---|---|---|---|
| 4,373,071 | A | 2/1983 | Itakura |
| 4,401,796 | A | 8/1983 | Itakura |
| 4,415,732 | A | 11/1983 | Caruthers et al. |
| 4,458,066 | A | 7/1984 | Caruthers et al. |
| 4,500,707 | A | 2/1985 | Caruthers et al. |
| 4,668,777 | A | 5/1987 | Caruthers et al. |
| 4,897,355 | A | 1/1990 | Eppstein et al. |
| 4,973,679 | A | 11/1990 | Caruthers et al. |
| 5,047,524 | A | 9/1991 | Andrus et al. |
| 5,132,418 | A | 7/1992 | Caruthers et al. |
| 5,153,319 | A | 10/1992 | Caruthers et al. |
| 5,171,678 | A | 12/1992 | Behr et al. |
| 5,262,530 | A | 11/1993 | Andrus et al. |
| 5,334,761 | A | 8/1994 | Gebeyehu et al. |
| 5,700,642 | A | 12/1997 | Monforte et al. |
| 5,744,335 | A | 4/1998 | Wolff et al. |
| 5,885,613 | A | 3/1999 | Holland et al. |
| 8,278,036 | B2 | 10/2012 | Kariko et al. |
| 2008/0193509 | A1 | 8/2008 | Yoshino et al. |
| 2012/0195936 | A1 | 8/2012 | Rudolph et al. |
| 2014/0134221 | A1 | 5/2014 | Beyer et al. |
| 2015/0190343 | A1 * | 7/2015 | Zal .......................... A61P 7/08 514/13.5 |
| 2015/0376220 | A1 | 12/2015 | Derosa et al. |

(Continued)

FOREIGN PATENT DOCUMENTS

| | | | |
|---|---|---|---|
| WO | 2005121348 | A1 | 12/2005 |
| WO | 2010042877 | A1 | 4/2010 |

(Continued)

OTHER PUBLICATIONS

Ball et al.; Achieving long-term stability of lipid nanoparticles: examining the effect of pH, temperature, and lyophilization; Dove Press; International Journal of Nanomedicine 2017:12 305-315. (Year: 2017).*
International Search Report and Written Opinion, dated Feb. 22, 2022, issued in corresponding Int'l. App. No. PCT/US2021/053776 (10 pages).
Abysalh et al., "Methods and Composition for Messenger RNA Purification," U.S. Appl. No. 62/757,612, filed Nov. 8, 2018, 65 pages.
Abysalh et al., "Methods for Purification of Messenger RNA," U.S. Appl. No. 62/891,781, filed Aug. 26, 2019, 86 pages.

(Continued)

*Primary Examiner* — Robert A Wax
*Assistant Examiner* — John W Lippert, III
(74) *Attorney, Agent, or Firm* — MH2 Technology Law Group, LLP

(57) ABSTRACT

The present invention provides an improved process for preparing a stable lyophilized composition comprising lipid nanoparticles encapsulating mRNA, which results in high mRNA integrity suitable for both short- and long-term storage for therapeutic use. In some embodiments, the present invention provides a method of preparing a stable lyophilized composition comprising the steps of adding ascorbic acid to an aqueous solution comprising one or more lipid nanoparticles, freezing the aqueous solution to obtain a frozen solution, drying the frozen solution to obtain a lyophilized composition, and increasing and holding the temperature of the lyophilized composition to a temperature of between 15° C. to 30° C.

20 Claims, 7 Drawing Sheets

(56) References Cited

U.S. PATENT DOCUMENTS

2016/0032356 A1 2/2016 Heartlein et al.
2016/0040154 A1 2/2016 Heartlein et al.
2017/0172920 A1* 6/2017 Li .......................... A61P 1/04
2018/0125989 A1 5/2018 Derosa et al.
2018/0251754 A1 9/2018 Derosa et al.
2018/0251755 A1 9/2018 Abysalh et al.
2018/0258423 A1 9/2018 Dias et al.
2018/0333457 A1* 11/2018 Heartlein .............. A61K 47/26
2018/0361342 A1 12/2018 Zhang et al.
2019/0160152 A1* 5/2019 Hershkovitz ............ A61P 3/10
2020/0085745 A1 3/2020 Karve et al.

FOREIGN PATENT DOCUMENTS

WO 2010053572 A2 5/2010
WO 2010144740 A1 12/2010
WO 2011012316 A1 2/2011
WO 2012170889 A1 12/2012
WO 2013063468 A1 5/2013
WO 2013149140 A1 10/2013
WO 2015095340 A1 6/2015
WO 2015184256 A2 12/2015
WO 2015199952 A1 12/2015
WO 2016004202 A1 1/2016
WO 2016118724 A1 7/2016
WO 2016118725 A1 7/2016
WO 2016205691 A1 12/2016
WO 2017004143 A1 1/2017
WO 2017049245 A2 3/2017
WO 2017075531 A1 5/2017
WO 2017117528 A1 7/2017
WO 2017173054 A1 10/2017
WO 2019222424 A1 11/2019

OTHER PUBLICATIONS

Behr et al., "Efficient gene transfer into mammalian primary endocrine cells with lipopolyamine-coated DNA," Proceedings of the National Academy of Sciences (PNAS), vol. 86, Sep. 1989, pp. 6982-6986 (6 pages total).
Berge et al., "Pharmaceutical Salts," Journal of Pharmaceutical Sciences, vol. 66, Issue 1, Jan. 1977, pp. 1-19.
Budker et al., "Protein/Amphipathic Polyamine Complexes Enable Highly Efficient Transfection with Minimal Toxicity," BioTechniques, vol. 23, No. 1, Jul. 1997, pp. 139-147.
Felgner et al., "Lipofection: A highly efficient, lipid-mediated DNA-transfection procedure," Proceedings of the National Academy of Sciences USA, vol. 84, Nov. 1987, p. 7413-7417.
Frelichowska, J. (PCT Authorized Officer), International Search Report and Written Opinion of the International Searching Authority for International Application No. PCT/US2021/053776 dated Feb. 22, 2022, 11 pages.
Gao et al., "A Novel Cationic Liposome Reagent for Efficient Transfection of Mammalian Cells," Biochemical and Biophysical Research Communications, vol. 179, No. 1, Aug. 30, 1991, pp. 280-285.
Heyes et al., "Cationic lipid saturation influences intracellular delivery of encapsulated nucleic acids," Journal of Controlled Release, vol. 107, 2005 (Available online Jul. 28, 2005), pp. 276-287.
Klibanov et al., "Amphipathic polyethyleneglycols effectively prolong the circulation time of liposomes," FEBS Letters, vol. 268, No. 1, Jul. 1990, pp. 235-237.
Lasic, "Novel applications of liposomes," Trends in Biotechnology, vol. 16, No. 7, Jul. 1998, pp. 307-321.
McClellan et al., "Genetic Heterogeneity in Human Disease," Cell, vol. 141, Apr. 16, 2010, pp. 210-217.
Morrissey et al., "Potent and persistent in vivo anti-HBV activity of chemically modified siRNAs," Nature Biotechnology, vol. 23, No. 8, Aug. 2005 (Published Jul. 24, 2005), pp. 1002-1007.
Semple et al., "Rational Design of Cationic Lipids for siRNA Delivery," Nature Biotechnology, vol. 28, No. 2, Feb. 2010 (Published online Jan. 17, 2010), pp. 172-176 (7 pages total).
Whitehead et al., "Degradable Lipid Nanoparticles with Predictable In Vivo siRNA Delivery Activity," Nature Communications, vol. 5, No. 4277, 2014 (Available in PMC Dec. 27, 2014), 22 pages.
Zhang, Y., et al., "Cyclic Amino Acid Lipids," U.S. Appl. No. 62/758,179, filed Nov. 9, 2018, 157 pages.
Chinese Search Report for Chinese Application No. 202180076850.8 dated Jul. 29, 2025, 4 pages including English translation.
Hou et al., "Vitamin lipid nanoparticles enable adoptive macrophage transfer for the treatment of multidrug-resistant bacterial sepsis," Nature Nanotechnology, Jan. 2020 (Published online Jan. 6, 2020), vol. 15, pp. 41-46 (8 pages).

* cited by examiner

| Sample | %mRNA integrity after X Months | | |
|---|---|---|---|
| | 0 | 1 | 3 |
| A | 59 | 51 | 47 |
| B | 64 | 59 | |
| C | 43 | 37 | 32 |
| D | 55 | 52 | 46 |
| E | 69 | 40 | 40 |
| F | 59 | 59 | |
| G | 57 | 55 | 49 |
| H | 58 | 63 | |
| I | 59 | 56 | |
| J | 55 | 49 | 51 |

PROCESS AND FORMULATION OF LIPID NANOPARTICLES

RELATED APPLICATIONS

This application is a 35 U.S.C. § 371 National Stage Application of International Application No. PCT/US2021/053776, filed on Oct. 6, 2021, which claims priority to U.S. Provisional Application No. 63/088,047, filed on Oct. 6, 2020. The contents of each of the foregoing applications are hereby incorporated by reference in their entireties.

BACKGROUND

Lipid nanoparticle delivery of encapsulated messenger RNA (mRNA) is becoming an increasingly important approach for the treatment of a variety of diseases. However, mRNA is susceptible to degradation due to its inherent stability and sensitivity to temperature. Therefore, maintaining the integrity of the mRNA encapsulated in the lipid nanoparticle for both short- and long-term storage for therapeutic use is critical.

SUMMARY OF INVENTION

The present invention provides, among other things, an improved process for preparing a lyophilized composition comprising lipid nanoparticles encapsulating mRNA (mRNA-LNPs). The invention is based on the surprising discovery that each step of 1) adding ascorbic acid for lyophilization process, 2) pretreating the mRNA-LNP composition with a buffer to maintain pH prior to the lyophilization process, and 3) increasing and holding the temperature of the lyophilized composition (e.g., during the secondary drying step) to a high temperature (e.g., between 15° C. to 30° C.), can individually and collectively improve integrity of mRNA encapsulated in lipid nanoparticles post-lyophilization, resulting in highly stable lyophilized mRNA-LNP composition that is able to withstand long-term storage Furthermore, lyophilization process according to the present invention prolongs integrity of mRNA encapsulated in lipid nanoparticles during lyophilization, while also maintaining size, PDI, and encapsulation efficiency of mRNA-LNPs. Thus, in one aspect, the present invention provides an improved method of preparing stable lyophilized mRNA with high mRNA integrity for long-term and short-term storages.

In one aspect, the invention provides, among other things, a method of preparing a stable lyophilized composition comprising one or more lipid nanoparticles encapsulating mRNA, the method comprising the steps of (a) adding between 5 mM and 200 mM ascorbic acid to an aqueous solution comprising one or more lipid nanoparticles encapsulating mRNA having an initial mRNA integrity, (b) freezing the aqueous solution to obtain a frozen solution.

In some embodiments, upon reconstitution of the lyophilized composition following storage of the lyophilized composition for four weeks at a temperature of 15 to 25° C., the mRNA integrity following reconstitution is at least 50% the initial mRNA integrity. In some embodiments, upon reconstitution of the lyophilized composition following storage of the lyophilized composition for four weeks at a temperature of 15 to 25° C., the mRNA integrity following reconstitution is at least 55% the initial mRNA integrity. In some embodiments, upon reconstitution of the lyophilized composition following storage of the lyophilized composition for four weeks at a temperature of 15 to 25° C., the mRNA integrity following reconstitution is at least 60% the initial mRNA integrity. In some embodiments, upon reconstitution of the lyophilized composition following storage of the lyophilized composition for four weeks at a temperature of 15 to 25° C., the mRNA integrity following reconstitution is at least 65% the initial mRNA integrity. In some embodiments, upon reconstitution of the lyophilized composition following storage of the lyophilized composition for four weeks at a temperature of 15 to 25° C., the mRNA integrity following reconstitution is at least 70% the initial mRNA integrity. In some embodiments, upon reconstitution of the lyophilized composition following storage of the lyophilized composition for four weeks at a temperature of 15 to 25° C., the mRNA integrity following reconstitution is at least 75% the initial mRNA integrity. In some embodiments, upon reconstitution of the lyophilized composition following storage of the lyophilized composition for four weeks at a temperature of 15 to 25° C., the mRNA integrity following reconstitution is at least 80% the initial mRNA integrity. In some embodiments, upon reconstitution of the lyophilized composition following storage of the lyophilized composition for four weeks at a temperature of 15 to 25° C., the mRNA integrity following reconstitution is at least 85% the initial mRNA integrity. In some embodiments, upon reconstitution of the lyophilized composition following storage of the lyophilized composition for four weeks at a temperature of 15 to 25° C., the mRNA integrity following reconstitution is at least 90% the initial mRNA integrity. In some embodiments, upon reconstitution of the lyophilized composition following storage of the lyophilized composition for four weeks at a temperature of 15 to 25° C., the mRNA integrity following reconstitution is at least 95% the initial mRNA integrity.

In some embodiments, the method includes prior to step (a), a step of removing citric acid from the aqueous solution. In some embodiments, the step of removing citric acid comprises washing the aqueous solution comprising citric acid and EDTA at a pH of pH 6 to pH 8. In some embodiments, the step of removing citric acid comprises washing the aqueous solution comprising 10 mM citric acid and 1 mM EDTA at a pH of pH 6 to pH 8. In some embodiments, the step of removing citric acid comprises washing the aqueous solution comprising citric acid and EDTA at a pH of pH 6 to pH 8. In some embodiments, the aqueous solution comprises 1 mM citrate buffer. In some embodiments, the aqueous solution comprises 2 mM citrate buffer. In some embodiments, the aqueous solution comprises 5 mM citrate buffer. In some embodiments, the aqueous solution comprises 8 mM citrate buffer. In some embodiments, the aqueous solution comprises 10 mM citrate buffer. In some embodiments, the aqueous solution comprises 15 mM citrate buffer. In some embodiments, the aqueous solution comprises 20 mM citrate buffer. In some embodiments, the aqueous solution comprises 25 mM citrate buffer. In some embodiments, the aqueous solution comprises 50 mM citrate buffer. In some embodiments, the aqueous solution comprises 0.1 mM EDTA. In some embodiments, the aqueous solution comprises 0.5 mM EDTA. In some embodiments, the aqueous solution comprises 1 mM EDTA. In some embodiments, the aqueous solution comprises 2.5 mM EDTA. In some embodiments, the aqueous solution comprises 5 mM EDTA. In some embodiments, the aqueous solution comprises 7.5 mM EDTA. In some embodiments, the aqueous solution comprises 10 mM EDTA.

In some embodiments, the method includes, following step (c), step of (d) increasing and holding the temperature of the lyophilized composition to a temperature of between 15° C. to 30° C.

In some embodiments, an aqueous solution comprises about 1 mM to 500 mM ascorbic acid. In some embodiments, an aqueous solution comprises about 5 mM to 200 mM ascorbic acid. In some embodiments, an aqueous solution comprises about 10 mM to 100 mM ascorbic acid. In some embodiments, an aqueous solution comprises about 10 mM to 50 mM ascorbic acid. In some embodiments, an aqueous solution comprises about 20 mM to 50 mM ascorbic acid. In some embodiments, an aqueous solution comprises about 20 mM to 30 mM ascorbic acid. In some embodiments, an aqueous solution comprises about 10 mM to 30 mM ascorbic acid. In some embodiments, an aqueous solution comprises about 10 mM to 20 mM ascorbic acid.

In some embodiments, an aqueous solution comprises about 1 mM ascorbic acid. In some embodiments, an aqueous solution comprises about 2 mM ascorbic acid. In some embodiments, an aqueous solution comprises about 3 mM ascorbic acid. In some embodiments, an aqueous solution comprises about 5 mM ascorbic acid. In some embodiments, an aqueous solution comprises about 8 mM ascorbic acid. In some embodiments, an aqueous solution comprises about 10 mM ascorbic acid. In some embodiments, an aqueous solution comprises about 15 mM ascorbic acid. In some embodiments, an aqueous solution comprises about 20 mM ascorbic acid. In some embodiments, an aqueous solution comprises about 25 mM ascorbic acid. In some embodiments, an aqueous solution comprises about 30 mM ascorbic acid. In some embodiments, an aqueous solution comprises about 40 mM ascorbic acid. In some embodiments, an aqueous solution comprises about 50 mM ascorbic acid. In some embodiments, an aqueous solution comprises about 75 mM ascorbic acid. In some embodiments, an aqueous solution comprises about 100 mM ascorbic acid. In some embodiments, an aqueous solution comprises about 125 mM ascorbic acid. In some embodiments, an aqueous solution comprises about 150 mM ascorbic acid. In some embodiments, an aqueous solution comprises about 175 mM ascorbic acid. In some embodiments, an aqueous solution comprises about 200 mM ascorbic acid. In some embodiments, an aqueous solution comprises about 250 mM ascorbic acid. In some embodiments, an aqueous solution comprises about 300 mM ascorbic acid. In some embodiments, an aqueous solution comprises about 400 mM ascorbic acid. In some embodiments, an aqueous solution comprises about 500 mM ascorbic acid.

In some embodiments, a drying step is performed for longer than 5 hours. In some embodiments, a drying step is performed for longer than 10 hours. In some embodiments, a drying step is performed for longer than 15 hours. In some embodiments, a drying step is performed for longer than 20 hours. In some embodiments, a drying step is performed for longer than 30 hours. In some embodiments, a drying step is performed for longer than 50 hours. In some embodiments, a drying step is performed for longer than 75 hours. In some embodiments, a drying step is performed for longer than 100 hours. In some embodiments, a drying step is performed for longer than 110 hours. In some embodiments, a drying step is performed for longer than 120 hours. In some embodiments, a drying step is performed for longer than 130 hours. In some embodiments, a drying step is performed for longer than 140 hours. In some embodiments, a drying step is performed for longer than 150 hours. In some embodiments, a drying step is performed for longer than 160 hours. In some embodiments, a drying step is performed for longer than 170 hours. In some embodiments, a drying step is performed for longer than 200 hours.

In some embodiments, a drying step is performed for about 10 to 300 hours. In some embodiments, a drying step is performed for about 50 to 200 hours. In some embodiments, a drying step is performed for about 100 to 150 hours. In some embodiments, a drying step is performed for about 120 hours. In some embodiments, a drying step is performed for about 130 hours. In some embodiments, a drying step is performed for about 140 hours. In some embodiments, a drying step is performed for about 150 hours. In some embodiments, a drying step is performed for about 160 hours.

In some embodiments, a lyophilized composition is held at a temperature of between 5° C. and 40° C. for longer than 1 hour. In some embodiments, a lyophilized composition is held at a temperature of between 5° C. and 40° C. for longer than 2 hours. In some embodiments, a lyophilized composition is held at a temperature of between 5° C. and 40° C. for longer than 3 hours. In some embodiments, a lyophilized composition is held at a temperature of between 5° C. and 40° C. for longer than 4 hours. In some embodiments, a lyophilized composition is held at a temperature of between 5° C. and 40° C. for longer than 5 hours. In some embodiments, a lyophilized composition is held at a temperature of between 5° C. and 40° C. for longer than 7 hours. In some embodiments, a lyophilized composition is held at a temperature of between 5° C. and 40° C. for longer than 10 hours. In some embodiments, a lyophilized composition is held at a temperature of between 5° C. and 40° C. for longer than 15 hours.

In some embodiments, a lyophilized composition is held at a temperature of between 10° C. and 30° C. for longer than 1 hour. In some embodiments, a lyophilized composition is held at a temperature of between 10° C. and 30° C. for longer than 2 hours. In some embodiments, a lyophilized composition is held at a temperature of between 10° C. and 30° C. for longer than 3 hours. In some embodiments, a lyophilized composition is held at a temperature of between 10° C. and 30° C. for longer than 4 hours. In some embodiments, a lyophilized composition is held at a temperature of between 10° C. and 30° C. for longer than 5 hours. In some embodiments, a lyophilized composition is held at a temperature of between 10° C. and 30° C. for longer than 7 hours. In some embodiments, a lyophilized composition is held at a temperature of between 10° C. and 30° C. for longer than 10 hours. In some embodiments, a lyophilized composition is held at a temperature of between 10° C. and 30° C. for longer than 15 hours.

In some embodiments, a lyophilized composition is held at a temperature of between 20° C. and 30° C. for longer than 1 hour. In some embodiments, a lyophilized composition is held at a temperature of between 20° C. and 30° C. for longer than 2 hours. In some embodiments, a lyophilized composition is held at a temperature of between 20° C. and 30° C. for longer than 3 hours. In some embodiments, a lyophilized composition is held at a temperature of between 20° C. and 30° C. for longer than 4 hours. In some embodiments, a lyophilized composition is held at a temperature of between 20° C. and 30° C. for longer than 5 hours. In some embodiments, a lyophilized composition is held at a temperature of between 20° C. and 30° C. for longer than 7 hours. In some embodiments, a lyophilized composition is held at a temperature of between 20° C. and 30° C. for longer than 10 hours. In some embodiments, a lyophilized composition is held at a temperature of between 20° C. and 30° C. for longer than 15 hours.

In some embodiments, a lyophilized composition is held at a temperature of about 20° C. for longer than 1 hours. In some embodiments, a lyophilized composition is held at a temperature of about 20° C. for longer than 2 hours. In some embodiments, a lyophilized composition is held at a temperature of about 20° C. for longer than 3 hours. In some embodiments, a lyophilized composition is held at a temperature of about 20° C. for longer than 4 hours. In some embodiments, a lyophilized composition is held at a temperature of about 20° C. for longer than 5 hours. In some embodiments, a lyophilized composition is held at a temperature of about 20° C. for longer than 7 hours. In some embodiments, a lyophilized composition is held at a temperature of about 20° C. for longer than 10 hours. In some embodiments, a lyophilized composition is held at a temperature of about 20° C. for longer than 15 hours.

In some embodiments, an initial mRNA integrity is higher than 40% and the mRNA integrity following reconstitution remains higher than 40%. In some embodiments, an initial mRNA integrity is higher than 45% and the mRNA integrity following reconstitution remains higher than 45%. In some embodiments, an initial mRNA integrity is higher than 50% and the mRNA integrity following reconstitution remains higher than 50%. In some embodiments, an initial mRNA integrity is higher than 55% and the mRNA integrity following reconstitution remains higher than 55%. In some embodiments, an initial mRNA integrity is higher than 60% and the mRNA integrity following reconstitution remains higher than 60%.

In some embodiments, an initial mRNA integrity is higher than 40% and the mRNA integrity following reconstitution is higher than 30%. In some embodiments, an initial mRNA integrity is higher than 45% and the mRNA integrity following reconstitution is higher than 35%. In some embodiments, an initial mRNA integrity is higher than 50% and the mRNA integrity following reconstitution is higher than 40%. In some embodiments, an initial mRNA integrity is higher than 55% and the mRNA integrity following reconstitution is higher than 45%. In some embodiments, an initial mRNA integrity is higher than 60% and the mRNA integrity following reconstitution is higher than 50%. In some embodiments, an initial mRNA integrity is higher than 65% and the mRNA integrity following reconstitution is higher than 55%.

In some embodiments, an mRNA integrity of the lyophilized composition is about or higher than 20% upon storage at a temperature of between 2° C. and 8° C. for longer than one month. In some embodiments, an mRNA integrity of the lyophilized composition is about or higher than 30% upon storage at a temperature of between 2° C. and 8° C. for longer than one month. In some embodiments, an mRNA integrity of the lyophilized composition is about or higher than 40% upon storage at a temperature of between 2° C. and 8° C. for longer than one month. In some embodiments, an mRNA integrity of the lyophilized composition is about or higher than 45% upon storage at a temperature of between 2° C. and 8° C. for longer than one month. In some embodiments, an mRNA integrity of the lyophilized composition is about or higher than 50% upon storage at a temperature of between 2° C. and 8° C. for longer than one month. In some embodiments, an mRNA integrity of the lyophilized composition is about or higher than 55% upon storage at a temperature of between 2° C. and 8° C. for longer than one month. In some embodiments, an mRNA integrity of the lyophilized composition is about or higher than 60% upon storage at a temperature of between 2° C. and 8° C. for longer than one month. In some embodiments, an mRNA integrity of the lyophilized composition is about or higher than 65% upon storage at a temperature of between 2° C. and 8° C. for longer than one month. In some embodiments, an mRNA integrity of the lyophilized composition is about or higher than 70% upon storage at a temperature of between 2° C. and 8° C. for longer than one month. In some embodiments, an mRNA integrity of the lyophilized composition is about or higher than 80% upon storage at a temperature of between 2° C. and 8° C. for longer than one month.

In some embodiments, an mRNA integrity of the lyophilized composition is about or higher than 20% upon storage at a temperature of between 2° C. and 8° C. for longer than two months. In some embodiments, an mRNA integrity of the lyophilized composition is about or higher than 30% upon storage at a temperature of between 2° C. and 8° C. for longer than two months. In some embodiments, an mRNA integrity of the lyophilized composition is about or higher than 40% upon storage at a temperature of between 2° C. and 8° C. for longer than two months. In some embodiments, an mRNA integrity of the lyophilized composition is about or higher than 45% upon storage at a temperature of between 2° C. and 8° C. for longer than two months. In some embodiments, an mRNA integrity of the lyophilized composition is about or higher than 50% upon storage at a temperature of between 2° C. and 8° C. for longer than two months. In some embodiments, an mRNA integrity of the lyophilized composition is about or higher than 55% upon storage at a temperature of between 2° C. and 8° C. for longer than two months. In some embodiments, an mRNA integrity of the lyophilized composition is about or higher than 60% upon storage at a temperature of between 2° C. and 8° C. for longer than two months. In some embodiments, an mRNA integrity of the lyophilized composition is about or higher than 65% upon storage at a temperature of between 2° C. and 8° C. for longer than two months. In some embodiments, an mRNA integrity of the lyophilized composition is about or higher than 70% upon storage at a temperature of between 2° C. and 8° C. for longer than two months. In some embodiments, an mRNA integrity of the lyophilized composition is about or higher than 80% upon storage at a temperature of between 2° C. and 8° C. for longer than two months.

In some embodiments, an mRNA integrity of the lyophilized composition is about or higher than 20% upon storage at a temperature of between 2° C. and 8° C. for longer than three months. In some embodiments, an mRNA integrity of the lyophilized composition is about or higher than 30% upon storage at a temperature of between 2° C. and 8° C. for longer than three months. In some embodiments, an mRNA integrity of the lyophilized composition is about or higher than 40% upon storage at a temperature of between 2° C. and 8° C. for longer than three months. In some embodiments, an mRNA integrity of the lyophilized composition is about or higher than 45% upon storage at a temperature of between 2° C. and 8° C. for longer than three months. In some embodiments, an mRNA integrity of the lyophilized composition is about or higher than 50% upon storage at a temperature of between 2° C. and 8° C. for longer than three months. In some embodiments, an mRNA integrity of the lyophilized composition is about or higher than 55% upon storage at a temperature of between 2° C. and 8° C. for longer than three months. In some embodiments, an mRNA integrity of the lyophilized composition is about or higher than 60% upon storage at a temperature of between 2° C. and 8° C. for longer than three months. In some embodiments, an mRNA integrity of the lyophilized composition is about or higher than 65% upon storage at a temperature of between 2° C. and 8° C. for longer than three months. In some embodiments, an mRNA integrity of the lyophilized composition is about or higher than 70% upon storage at a temperature of between 2° C. and 8° C. for longer than three months. In some embodiments, an mRNA integrity of the lyophilized composition is about or higher than 80% upon storage at a temperature of between 2° C. and 8° C. for longer than three months.

In some embodiments, an mRNA integrity of the lyophilized composition is about or higher than 20% upon storage at a temperature of between 2° C. and 8° C. for longer than five months. In some embodiments, an mRNA integrity of the lyophilized composition is about or higher than 30% upon storage at a temperature of between 2° C. and 8° C. for longer than five months. In some embodiments, an mRNA integrity of the lyophilized composition is about or higher than 40% upon storage at a temperature of between 2° C. and 8° C. for longer than five months. In some embodiments, an mRNA integrity of the lyophilized composition is about or higher than 45% upon storage at a temperature of between 2° C. and 8° C. for longer than five months. In some embodiments, an mRNA integrity of the lyophilized composition is about or higher than 50% upon storage at a temperature of between 2° C. and 8° C. for longer than five months. In some embodiments, an mRNA integrity of the lyophilized composition is about or higher than 55% upon storage at a temperature of between 2° C. and 8° C. for longer than five months. In some embodiments, an mRNA integrity of the lyophilized composition is about or higher than 60% upon storage at a temperature of between 2° C. and 8° C. for longer than five months. In some embodiments, an mRNA integrity of the lyophilized composition is about or higher than 65% upon storage at a temperature of between 2° C. and 8° C. for longer than five months. In some embodiments, an mRNA integrity of the lyophilized composition is about or higher than 70% upon storage at a temperature of between 2° C. and 8° C. for longer than five months. In some embodiments, an mRNA integrity of the lyophilized composition is about or higher than 80% upon storage at a temperature of between 2° C. and 8° C. for longer than five months.

In some embodiments, an mRNA integrity of the lyophilized composition is about or higher than 20% upon storage at a room temperature (e.g., between 15° C. and 25° C.) for longer than three days. In some embodiments, an mRNA integrity of the lyophilized composition is about or higher than 20% upon storage at a temperature of between 15° C. and 25° C. for longer than three days. In some embodiments, an mRNA integrity of the lyophilized composition is about or higher than 30% upon storage at a temperature of between 15° C. and 25° C. for longer than three days. In some embodiments, an mRNA integrity of the lyophilized composition is about or higher than 40% upon storage at a temperature of between 15° C. and 25° C. for longer than three days. In some embodiments, an mRNA integrity of the lyophilized composition is about or higher than 45% upon storage at a temperature of between 15° C. and 25° C. for longer than three days. In some embodiments, an mRNA integrity of the lyophilized composition is about or higher than 50% upon storage at a temperature of between 15° C. and 25° C. for longer than three days. In some embodiments, an mRNA integrity of the lyophilized composition is about or higher than 55% upon storage at a temperature of between 15° C. and 25° C. for longer than three days. In some embodiments, an mRNA integrity of the lyophilized composition is about or higher than 60% upon storage at a temperature of between 15° C. and 25° C. for longer than three days. In some embodiments, an mRNA integrity of the lyophilized composition is about or higher than 65% upon storage at a temperature of between 15° C. and 25° C. for longer than three days. In some embodiments, an mRNA integrity of the lyophilized composition is about or higher than 70% upon storage at a temperature of between 15° C. and 25° C. for longer than three days.

In some embodiments, an mRNA integrity of the lyophilized composition is about or higher than 20% upon storage at a room temperature (e.g., between 15° C. and 25° C.) for longer than one week. In some embodiments, an mRNA integrity of the lyophilized composition is about or higher than 20% upon storage at a temperature of between 15° C. and 25° C. for longer than one week. In some embodiments, an mRNA integrity of the lyophilized composition is about or higher than 30% upon storage at a temperature of between 15° C. and 25° C. for longer than one week. In some embodiments, an mRNA integrity of the lyophilized composition is about or higher than 40% upon storage at a temperature of between 15° C. and 25° C. for longer than one week. In some embodiments, an mRNA integrity of the lyophilized composition is about or higher than 45% upon storage at a temperature of between 15° C. and 25° C. for longer than one week. In some embodiments, an mRNA integrity of the lyophilized composition is about or higher than 50% upon storage at a temperature of between 15° C. and 25° C. for longer than one week. In some embodiments, an mRNA integrity of the lyophilized composition is about or higher than 55% upon storage at a temperature of between 15° C. and 25° C. for longer than one week. In some embodiments, an mRNA integrity of the lyophilized composition is about or higher than 60% upon storage at a temperature of between 15° C. and 25° C. for longer than one week. In some embodiments, an mRNA integrity of the lyophilized composition is about or higher than 65% upon storage at a temperature of between 15° C. and 25° C. for longer than one week. In some embodiments, an mRNA integrity of the lyophilized composition is about or higher than 70% upon storage at a temperature of between 15° C. and 25° C. for longer than one week.

In some embodiments, an mRNA integrity of the lyophilized composition is about or higher than 20% upon storage at a room temperature (e.g., between 15° C. and 25° C.) for longer than two weeks. In some embodiments, an mRNA integrity of the lyophilized composition is about or higher than 20% upon storage at a temperature of between 15° C. and 25° C. for longer than two weeks. In some embodiments, an mRNA integrity of the lyophilized composition is about or higher than 30% upon storage at a temperature of between 15° C. and 25° C. for longer than two weeks. In some embodiments, an mRNA integrity of the lyophilized composition is about or higher than 40% upon storage at a temperature of between 15° C. and 25° C. for longer than two weeks. In some embodiments, an mRNA integrity of the lyophilized composition is about or higher than 45% upon storage at a temperature of between 15° C. and 25° C. for longer than two weeks. In some embodiments, an mRNA integrity of the lyophilized composition is about or higher than 50% upon storage at a temperature of between 15° C. and 25° C. for longer than two weeks. In some embodiments, an mRNA integrity of the lyophilized composition is about or higher than 55% upon storage at a temperature of between 15° C. and 25° C. for longer than two weeks. In some embodiments, an mRNA integrity of the lyophilized composition is about or higher than 60% upon storage at a temperature of between 15° C. and 25° C. for longer than two weeks. In some embodiments, an mRNA integrity of the lyophilized composition is about or higher than 65% upon storage at a temperature of between 15° C. and 25° C. for longer than two weeks. In some embodiments, an mRNA integrity of the lyophilized composition is about or higher than 70% upon storage at a temperature of between 15° C. and 25° C. for longer than two weeks.

In some embodiments, an mRNA integrity of the lyophilized composition is about or higher than 20% upon storage at a room temperature (e.g., between 15° C. and 25° C.) for longer than three weeks. In some embodiments, an mRNA integrity of the lyophilized composition is about or higher than 20% upon storage at a temperature of between 15° C. and 25° C. for longer than three weeks. In some embodiments, an mRNA integrity of the lyophilized composition is about or higher than 30% upon storage at a temperature of between 15° C. and 25° C. for longer than three weeks. In some embodiments, an mRNA integrity of the lyophilized composition is about or higher than 40% upon storage at a temperature of between 15° C. and 25° C. for longer than three weeks. In some embodiments, an mRNA integrity of the lyophilized composition is about or higher than 45% upon storage at a temperature of between 15° C. and 25° C. for longer than three weeks. In some embodiments, an mRNA integrity of the lyophilized composition is about or higher than 50% upon storage at a temperature of between 15° C. and 25° C. for longer than three weeks. In some embodiments, an mRNA integrity of the lyophilized composition is about or higher than 55% upon storage at a temperature of between 15° C. and 25° C. for longer than three weeks. In some embodiments, an mRNA integrity of the lyophilized composition is about or higher than 60% upon storage at a temperature of between 15° C. and 25° C. for longer than three weeks. In some embodiments, an mRNA integrity of the lyophilized composition is about or higher than 65% upon storage at a temperature of between 15° C. and 25° C. for longer than three weeks. In some embodiments, an mRNA integrity of the lyophilized composition is about or higher than 70% upon storage at a temperature of between 15° C. and 25° C. for longer than three weeks.

In some embodiments, an mRNA integrity of the lyophilized composition is about or higher than 20% upon storage at a room temperature (e.g., between 15° C. and 25° C.) for longer than four weeks. In some embodiments, an mRNA integrity of the lyophilized composition is about or higher than 20% upon storage at a temperature of between 15° C. and 25° C. for longer than four weeks. In some embodiments, an mRNA integrity of the lyophilized composition is about or higher than 30% upon storage at a temperature of between 15° C. and 25° C. for longer than four weeks. In some embodiments, an mRNA integrity of the lyophilized composition is about or higher than 40% upon storage at a temperature of between 15° C. and 25° C. for longer than four weeks. In some embodiments, an mRNA integrity of the lyophilized composition is about or higher than 45% upon storage at a temperature of between 15° C. and 25° C. for longer than four weeks. In some embodiments, an mRNA integrity of the lyophilized composition is about or higher than 50% upon storage at a temperature of between 15° C. and 25° C. for longer than four weeks. In some embodiments, an mRNA integrity of the lyophilized composition is about or higher than 55% upon storage at a temperature of between 15° C. and 25° C. for longer than four weeks. In some embodiments, an mRNA integrity of the lyophilized composition is about or higher than 60% upon storage at a temperature of between 15° C. and 25° C. for longer than four weeks. In some embodiments, an mRNA integrity of the lyophilized composition is about or higher than 65% upon storage at a temperature of between 15° C. and 25° C. for longer than four weeks. In some embodiments, an mRNA integrity of the lyophilized composition is about or higher than 70% upon storage at a temperature of between 15° C. and 25° C. for longer than four weeks.

In some embodiments, an mRNA integrity of the lyophilized composition is about or higher than 20% upon storage at a room temperature (e.g., between 15° C. and 25° C.) for longer than five weeks. In some embodiments, an mRNA integrity of the lyophilized composition is about or higher than 20% upon storage at a temperature of between 15° C. and 25° C. for longer than five weeks. In some embodiments, an mRNA integrity of the lyophilized composition is about or higher than 30% upon storage at a temperature of between 15° C. and 25° C. for longer than five weeks. In some embodiments, an mRNA integrity of the lyophilized composition is about or higher than 40% upon storage at a temperature of between 15° C. and 25° C. for longer than five weeks. In some embodiments, an mRNA integrity of the lyophilized composition is about or higher than 45% upon storage at a temperature of between 15° C. and 25° C. for longer than five weeks. In some embodiments, an mRNA integrity of the lyophilized composition is about or higher than 50% upon storage at a temperature of between 15° C. and 25° C. for longer than five weeks. In some embodiments, an mRNA integrity of the lyophilized composition is about or higher than 55% upon storage at a temperature of between 15° C. and 25° C. for longer than five weeks. In some embodiments, an mRNA integrity of the lyophilized composition is about or higher than 60% upon storage at a temperature of between 15° C. and 25° C. for longer than five weeks. In some embodiments, an mRNA integrity of the lyophilized composition is about or higher than 65% upon storage at a temperature of between 15° C. and 25° C. for longer than five weeks. In some embodiments, an mRNA integrity of the lyophilized composition is about or higher than 70% upon storage at a temperature of between 15° C. and 25° C. for longer than five weeks.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 50% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 50% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 50% that of the initial mRNA integrity.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 60% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 60% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 60% that of the initial mRNA integrity.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 45% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 45% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 45% that of the initial mRNA integrity.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 40% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 40% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for four weeks at a temperature of 15 to 25° C., the mRNA integrity following reconstitution is at least 40% that of the initial mRNA integrity.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 75% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 75% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 75% that of the initial mRNA integrity.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 80% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 80% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 85% that of the initial mRNA integrity.

In some embodiments, a stable lyophilized composition comprising one or more lipid nanoparticles encapsulating mRNA is prepared by adding 5 mM and 200 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 90% that of the initial mRNA integrity.

In some embodiments, a stable lyophilized composition comprising one or more lipid nanoparticles encapsulating mRNA is prepared by adding 10 mM and 30 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 90% that of the initial mRNA integrity.

In some embodiments, a stable lyophilized composition comprising one or more lipid nanoparticles encapsulating mRNA is prepared by adding about 20 mM ascorbic acid to an aqueous solution having the lipid nanoparticles encapsulating mRNA measured to have an initial mRNA integrity, and upon reconstitution of the lyophilized composition following storage of the lyophilized composition for 6 months at a temperature of 2 to 8° C., the mRNA integrity following reconstitution is at least 90% that of the initial mRNA integrity.

In some embodiments, mRNA integrity is determined by capillary electrophoresis (CE). In some embodiments, mRNA integrity is determined by gel electrophoresis. In some embodiments, mRNA integrity is determined by a microfluidic device. In some embodiments, mRNA integrity is determined by RT-qPCR. In some embodiments, mRNA integrity is determined by capillary gel electrophoresis (CGE). In some embodiments, mRNA integrity is determined by capillary zone electrophoresis (CZE). In some embodiments, mRNA integrity is determined by capillary micellular electrokinetic capillary chromatography (MEKC). In some embodiments, mRNA integrity is determined by capillary isoelectric focusing (cIEF). In some embodiments, mRNA integrity is determined by capillary electrochromatography (CEC).

In some embodiments, a drying step is performed at a temperature below freezing point. In some embodiments, a drying step is performed at a temperature of between 0° C. and −100° C. In some embodiments, a drying step is performed at a temperature of between −10° C. and −50° C. In some embodiments, a drying step is performed at a temperature of between −20° C. and −30° C. In some embodiments, a drying step is performed at a temperature of about −30° C. In some embodiments, a drying step is performed at a temperature of about −25° C. In some embodiments, a drying step is performed at a temperature of about −20° C. In some embodiments, a drying step is performed at a temperature of about −15° C. In some embodiments, a drying step is performed at a temperature of about −10° C.

In some embodiments, a drying step is performed at a pressure below 4580 mTorr (4.58 Torr). In some embodiments, a drying step is performed at a pressure of between 0 mTorr and 300 mTorr. In some embodiments, a drying step is performed at a pressure of between 10 mTorr and 200 mTorr. In some embodiments, a drying step is performed at a pressure of between 20 mTorr and 60 mTorr. In some embodiments, a drying step is performed at a pressure of about 100 mTorr. In some embodiments, a drying step is performed at a pressure of about 80 mTorr. In some embodiments, a drying step is performed at a pressure of about 60 mTorr. In some embodiments, a drying step is performed at a pressure of about 50 mTorr. In some embodiments, a drying step is performed at a pressure of about 40 mTorr. In some embodiments, a drying step is performed at a pressure of about 30 mTorr. In some embodiments, a drying step is performed at a pressure of about 20 mTorr.

In some embodiments, the temperature of the lyophilized composition is increased and held at a temperature of between 0° C. and 40° C. in step (d) (e.g., secondary drying step). In some embodiments, the temperature of the lyophilized composition is increased and held at a temperature of between 5° C. and 30° C. in step (d). In some embodiments, the temperature of the lyophilized composition is increased and held at a temperature of between 20° C. and 30° C. in step (d). In some embodiments, the temperature of the lyophilized composition is increased and held at a temperature of about 10° C. in step (d). In some embodiments, the temperature of the lyophilized composition is increased and held at a temperature of about 15° C. in step (d). In some embodiments, the temperature of the lyophilized composition is increased and held at a temperature of about 20° C. in step (d). In some embodiments, the temperature of the lyophilized composition is increased and held at a temperature of about 25° C. in step (d). In some embodiments, the temperature of the lyophilized composition is increased and held at a temperature of about 30° C. in step (d). In some embodiments, the temperature of the lyophilized composition is increased and held at a temperature of about 35° C. in step (d).

In some embodiments, an aqueous solution comprises a lyoprotectant. In some embodiments, an aqueous solution comprises (free) carbohydrates such as glucose, fructose, galactose, sorbose, mannose, and combinations thereof. In some embodiments, an aqueous solution comprises disaccharides such as lactose, maltose, sucrose, trehalose, cellobiose, and thereof. In some embodiments, an aqueous solution comprises polysaccharides, such as raffinose, melezitose, maltodextrins, dextrans, dextrins, cellulose, starches and combinations thereof. In some embodiments, an aqueous solution comprises alditols, such as glycerol, mannitol, xylitol, maltitol, lactitol, xylitol sorbitol, pyranosyl sorbitol, myoinositol, and combinations thereof. In some embodiments, an aqueous solution comprises lactose. In some embodiments, an aqueous solution comprises lactose mannose. In some embodiments, an aqueous solution comprises lactose. In some embodiments, an aqueous solution comprises mannitol. In some embodiments, an aqueous solution comprises sucrose. In some embodiments, an aqueous solution comprises trehalose.

In some embodiments, an aqueous solution has a pH below 9.0. In some embodiments, an aqueous solution has a pH below 8.5. In some embodiments, an aqueous solution has a pH below 8.0. In some embodiments, an aqueous solution has a pH below 7.8. In some embodiments, an aqueous solution has a pH below 7.5. In some embodiments, an aqueous solution has a pH below 7.3. In some embodiments, an aqueous solution has a pH below 7.0. In some embodiments, an aqueous solution has a pH below 6.8. In some embodiments, an aqueous solution has a pH below 6.5. In some embodiments, an aqueous solution has a pH below 6.3. In some embodiments, an aqueous solution has a pH below 6.2. In some embodiments, an aqueous solution has a pH below 6.0. In some embodiments, an aqueous solution has a pH below 5.8. In some embodiments, an aqueous solution has a pH below 5.5. In some embodiments, an aqueous solution has a pH below 5.2. In some embodiments, an aqueous solution has a pH below 5.0. In some embodiments, an aqueous solution has a pH below 4.8. In some embodiments, an aqueous solution has a pH below 4.5. In some embodiments, an aqueous solution has a pH below 4.3. In some embodiments, an aqueous solution has a pH below 4.0. In some embodiments, an aqueous solution has a pH below 3.8. In some embodiments, an aqueous solution has a pH ranging between 3.0 and 7.5. In some embodiments, an aqueous solution has a pH ranging between 4.0 and 7.0. In some embodiments, an aqueous solution has a pH ranging between 4.5 and 6.5.

In one aspect, the invention provides, among other things, a stable lyophilized composition comprising one or more lipid nanoparticles encapsulating mRNA prepared by the method of the present invention.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for four weeks at a temperature of 15 to 25° C., the integrity of the mRNA following reconstitution is at least 40% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for four weeks at a temperature of 15 to 25° C., the integrity of the mRNA following reconstitution is at least 40% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for four weeks at a temperature of 15 to 25° C., the integrity of the mRNA following reconstitution is at least 40% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for four weeks at a temperature of 15 to 25° C., the integrity of the mRNA following reconstitution is at least 45% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for four weeks at a temperature of 15 to 25° C., the integrity of the mRNA following reconstitution is at least 45% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for four weeks at a temperature of 15 to 25° C., the integrity of the mRNA following reconstitution is at least 45% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for four weeks at a temperature of 15 to 25° C., the integrity of the mRNA following reconstitution is at least 50% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for four weeks at a temperature of 15 to 25° C., the integrity of the mRNA following reconstitution is at least 50% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for four weeks at a temperature of 15 to 25° C., the integrity of the mRNA following reconstitution is at least 50% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for four weeks at a temperature of 15 to 25° C., the integrity of the mRNA following reconstitution is at least 60% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for four weeks at a temperature of 15 to 25° C., the integrity of the mRNA following reconstitution is at least 60% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for four weeks at a temperature of 15 to 25° C., the integrity of the mRNA following reconstitution is at least 60% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for six months at a temperature of 2 to 8° C., the integrity of the mRNA following reconstitution is at least 75% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for six months at a temperature of 2 to 8° C., the integrity of the mRNA following reconstitution is at least 75% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for six months at a temperature of 2 to 8° C., the integrity of the mRNA following reconstitution is at least 75% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for six months at a temperature of 2 to 8° C., the integrity of the mRNA following reconstitution is at least 80% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for six months at a temperature of 2 to 8° C., the integrity of the mRNA following reconstitution is at least 80% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for six months at a temperature of 2 to 8° C., the integrity of the mRNA following reconstitution is at least 80% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for six months at a temperature of 2 to 8° C., the integrity of the mRNA following reconstitution is at least 85% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for six months at a temperature of 2 to 8° C., the integrity of the mRNA following reconstitution is at least 85% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for six months at a temperature of 2 to 8° C., the integrity of the mRNA following reconstitution is at least 85% the initial mRNA integrity.

In one aspect, the present invention provides a stable lyophilized composition comprising one or more lipid nanoparticles encapsulating mRNA and between 5 mM and 200 mM ascorbic acid, wherein upon reconstitution of the lyophilized composition following storage of the lyophilized composition for six months at a temperature of 2 to 8° C., the integrity of the mRNA following reconstitution is at least 90% the initial mRNA integrity.

In one aspect, the present invention provides a stable lyophilized composition comprising one or more lipid nanoparticles encapsulating mRNA and between 10 mM and 30 mM ascorbic acid, wherein upon reconstitution of the lyophilized composition following storage of the lyophilized composition for six months at a temperature of 2 to 8° C., the integrity of the mRNA following reconstitution is at least 90% the initial mRNA integrity.

In one aspect, the present invention provides a stable lyophilized composition comprising one or more lipid nanoparticles encapsulating mRNA and about 20 mM ascorbic acid, wherein upon reconstitution of the lyophilized composition following storage of the lyophilized composition for six months at a temperature of 2 to 8° C., the integrity of the mRNA following reconstitution is at least 90% the initial mRNA integrity.

In some embodiments, an mRNA integrity of a stable lyophilized composition is about or higher than 20%. In some embodiments, an mRNA integrity of a stable lyophilized composition is about or higher than 30%. In some embodiments, an mRNA integrity of a stable lyophilized composition is about or higher than 40%. In some embodiments, an mRNA integrity of a stable lyophilized composition is about or higher than 45%. In some embodiments, an mRNA integrity of a stable lyophilized composition is about or higher than 50%. In some embodiments, an mRNA integrity of a stable lyophilized composition is about or higher than 55%. In some embodiments, an mRNA integrity of a stable lyophilized composition is about or higher than 60%. In some embodiments, an mRNA integrity of a stable lyophilized composition is about or higher than 65%. In some embodiments, an mRNA integrity of a stable lyophilized composition is about or higher than 70%. In some embodiments, an mRNA integrity of a stable lyophilized composition is about or higher than 75%. In some embodiments, an mRNA integrity of a stable lyophilized composition is about or higher than 80%. In some embodiments, an mRNA integrity of a stable lyophilized composition is about or higher than 85%. In some embodiments, an mRNA integrity of a stable lyophilized composition is about or higher than 90%. In some embodiments, an mRNA integrity of a stable lyophilized composition is about or higher than 95%.

In some embodiments, a stable lyophilized composition comprises less than 5 mM citrate. In some embodiments, a stable lyophilized composition comprises less than 4 mM citrate. In some embodiments, a stable lyophilized composition comprises less than 3 mM citrate. In some embodiments, a stable lyophilized composition comprises less than 2 mM citrate. In some embodiments, a stable lyophilized composition comprises less than 1 mM citrate. In some embodiments, a stable lyophilized composition comprises less than 0.5 mM citrate. In some embodiments, a stable lyophilized composition comprises less than 0.3 mM citrate.

In some embodiments, a stable lyophilized composition comprises less than 0.2 mM citrate. In some embodiments, a stable lyophilized composition comprises less than 0.1 mM citrate. In some embodiments, a stable lyophilized composition comprises less than 0.05 mM citrate. In some embodiments, a stable lyophilized composition comprises substantially no residual citrate.

In some embodiments, a stable lyophilized composition comprises about 1 mM to 500 mM ascorbic acid. In some embodiments, a stable lyophilized composition comprises about 5 mM to 200 mM ascorbic acid. In some embodiments, a stable lyophilized composition comprises about 10 mM to 100 mM ascorbic acid. In some embodiments, a stable lyophilized composition comprises about 10 mM to 50 mM ascorbic acid. In some embodiments, a stable lyophilized composition comprises about 20 mM to 50 mM ascorbic acid. In some embodiments, a stable lyophilized composition comprises about 20 mM to 30 mM ascorbic acid.

In some embodiments, a stable lyophilized composition comprises about 1 mM ascorbic acid. In some embodiments, a stable lyophilized composition comprises about 2 mM ascorbic acid. In some embodiments, a stable lyophilized composition comprises about 3 mM ascorbic acid. In some embodiments, a stable lyophilized composition comprises about 5 mM ascorbic acid. In some embodiments, a stable lyophilized composition comprises about 8 mM ascorbic acid. In some embodiments, a stable lyophilized composition comprises about 10 mM ascorbic acid. In some embodiments, a stable lyophilized composition comprises about 15 mM ascorbic acid. In some embodiments, a stable lyophilized composition comprises about 20 mM ascorbic acid. In some embodiments, a stable lyophilized composition comprises about 25 mM ascorbic acid. In some embodiments, a stable lyophilized composition comprises about 30 mM ascorbic acid. In some embodiments, a stable lyophilized composition comprises about 40 mM ascorbic acid. In some embodiments, a stable lyophilized composition comprises about 50 mM ascorbic acid. In some embodiments, a stable lyophilized composition comprises about 75 mM ascorbic acid. In some embodiments, a stable lyophilized composition comprises about 100 mM ascorbic acid. In some embodiments, a stable lyophilized composition comprises about 125 mM ascorbic acid. In some embodiments, a stable lyophilized composition comprises about 150 mM ascorbic acid. In some embodiments, a stable lyophilized composition comprises about 175 mM ascorbic acid. In some embodiments, a stable lyophilized composition comprises about 200 mM ascorbic acid. In some embodiments, a stable lyophilized composition comprises about 250 mM ascorbic acid. In some embodiments, a stable lyophilized composition comprises about 300 mM ascorbic acid. In some embodiments, a stable lyophilized composition comprises about 400 mM ascorbic acid. In some embodiments, a stable lyophilized composition comprises about 500 mM ascorbic acid.

DEFINITIONS

Figure 1:
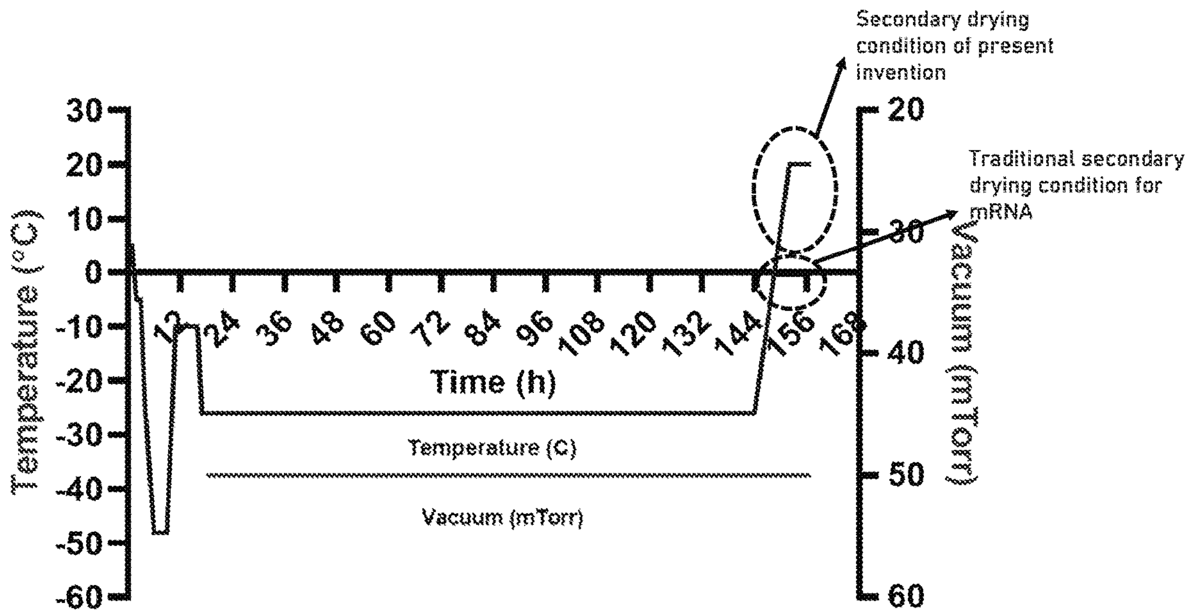
FIG. 1 depicts an exemplary graph showing lyophilization conditions of the present invention. Generally, lyophilization is carried out by freezing the mRNA in aqueous solution comprising a lyoprotectant, followed by primary and secondary drying steps. In this particular exemplary process shown in FIG. 1, the primary drying step starts when vacuum is at 50 mTorr.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, the term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term “amino acid” is used interchangeably with “amino acid residue,” and may refer to a free amino acid and/or to an amino acid residue of a peptide. It will be apparent from the context in which the term is used whether it refers to a free amino acid or a residue of a peptide.

Approximately or about: As used herein, the term “approximately” or “about,” as applied to one or more values of interest, refers to a value that is similar to a stated reference value. In certain embodiments, the term “approximately” or “about” refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Batch: As used herein, the term “batch” refers to a quantity or amount of mRNA purified at one time, e.g., purified according to a single manufacturing order during the same cycle of manufacture. A batch may refer to an amount of mRNA purified in one reaction.

Biologically active: As used herein, the phrase “biologically active” refers to a characteristic of any agent that has activity in a biological system, and particularly in an organism. For instance, an agent that, when administered to an organism, has a biological effect on that organism, is considered to be biologically active.

Delivery: As used herein, the term “delivery” encompasses both local and systemic delivery. For example, delivery of mRNA encompasses situations in which an mRNA is delivered to a target tissue and the encoded protein is expressed and retained within the target tissue (also referred to as “local distribution” or “local delivery”), and situations in which an mRNA is delivered to a target tissue and the encoded protein is expressed and secreted into patient’s circulation system (e.g., serum) and systematically distributed and taken up by other tissues (also referred to as “systemic distribution” or “systemic delivery). In some embodiments, delivery is pulmonary delivery, e.g., comprising nebulization.

Efficacy: As used herein, the term “efficacy,” or grammatical equivalents, refers to an improvement of a biologically relevant endpoint, as related to delivery of mRNA that encodes a relevant protein or peptide. In some embodiments, the biological endpoint is protecting against an ammonium chloride challenge at certain time points after administration.

Encapsulation: As used herein, the term “encapsulation,” or its grammatical equivalent, refers to the process of confining a nucleic acid molecule within a nanoparticle.

Expression: As used herein, “expression” of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms “expression” and “production,” and their grammatical equivalents, are used interchangeably.

Improve, increase, or reduce: As used herein, the terms “improve,” “increase” or “reduce,” or grammatical equivalents, indicate values that are relative to a baseline measurement, such as a measurement in the same individual prior to initiation of the treatment described herein, or a measurement in a control subject (or multiple control subject) in the absence of the treatment described herein. A “control subject” is a subject afflicted with the same form of disease as the subject being treated, who is about the same age as the subject being treated.

Impurities: As used herein, the term “impurities” refers to substances inside a confined amount of liquid, gas, or solid, which differ from the chemical composition of the target material or compound. Impurities are also referred to as contaminants.

In Vitro: As used herein, the term “in vitro” refers to events that occur in an artificial environment, e.g., in a test tube or reaction vessel, in cell culture, etc., rather than within a multi-cellular organism.

In Vivo: As used herein, the term “in vivo” refers to events that occur within a multi-cellular organism, such as a human and a non-human animal. In the context of cell-based systems, the term may be used to refer to events that occur within a living cell (as opposed to, for example, in vitro systems).

Isolated: As used herein, the term “isolated” refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is “pure” if it is substantially free of other components. As used herein, calculation of percent purity of isolated substances and/or entities should not include excipients (e.g., buffer, solvent, water, etc.).

Lipid nanoparticle: As used herein, the term “lipid nanoparticle” or “liposome” refers to any lamellar, multilamellar, or solid nanoparticle vesicle. Typically, a liposome as used herein can be formed by mixing one or more lipids or by mixing one or more lipids and polymer(s). In some embodiments, a liposome suitable for the present invention contains a cationic lipids(s) and optionally non-cationic lipid(s), optionally cholesterol-based lipid(s), and/or optionally PEG-modified lipid(s).

Local distribution or delivery: As used herein, the terms “local distribution,” “local delivery,” or grammatical equivalent, refer to tissue specific delivery or distribution. Typically, local distribution or delivery requires a peptide or protein (e.g., enzyme) encoded by mRNAs be translated and expressed intracellularly or with limited secretion that avoids entering the patient’s circulation system.

messenger RNA (mRNA): As used herein, the term “messenger RNA (mRNA)” refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

mRNA integrity: As used herein, the term "mRNA integrity" refers to the quality of mRNA. In particular, mRNA integrity refers to the percentage of mRNA that is not degraded. mRNA integrity may be determined using methods well known in the art, for example, by RNA agarose gel electrophoresis (e.g., Ausubel et al., John Weley & Sons, Inc., 1997, Current Protocols in Molecular Biology) or capillary electrophoresis. In some embodiments, mRNA integrity can be quantified and expressed as a percent. For example, capillary electrophoresis and similar methods can be uses to separate degraded mRNA from mRNA that is not degraded and then the percent integrity, i.e., percent of mRNA not degraded relative to total mRNA, can be calculated based on the relative areas from the resulting chromatogram.

N/P Ratio: As used herein, the term "N/P ratio" refers to a molar ratio of positively charged molecular units in the cationic lipids in a lipid nanoparticle relative to negatively charged molecular units in the mRNA encapsulated within that lipid nanoparticle. As such, N/P ratio is typically calculated as the ratio of moles of amine groups in cationic lipids in a lipid nanoparticle relative to moles of phosphate groups in mRNA encapsulated within that lipid nanoparticle.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Potency: As used herein, the term "potency," or grammatical equivalents, refers to level of expression of protein(s) or peptide(s) that the mRNA encodes and/or the resulting biological effect.

Salt: As used herein the term "salt" refers to an ionic compound that does or may result from a neutralization reaction between an acid and a base.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially free: As used herein, the term "substantially free" refers to a state in which relatively little or no amount of a substance to be removed (e.g., prematurely aborted RNA sequences) are present. For example, "substantially free of prematurely aborted RNA sequences" means the prematurely aborted RNA sequences are present at a level less than approximately 5%, 4%, 3%, 2%, 1.0%, 0.9%, 0.8%, 0.7%, 0.6%, 0.5%, 0.4%, 0.3%, 0.2%, 0.1% or less (w/w) of the impurity. Alternatively, "substantially free of prematurely aborted RNA sequences" means the prematurely aborted RNA sequences are present at a level less than about 100 ng, 90 ng, 80 ng, 70 ng, 60 ng, 50 ng, 40 ng, 30 ng, 20 ng, 10 ng, 1 ng, 500 pg, 100 pg, 50 pg, 10 pg, or less.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Therapeutic Index: As used herein, "Therapeutic Index" is the ratio of the concentration of a drug in the blood at which it becomes toxic, and the concentration at which it is effective. The larger the therapeutic index, the safer the drug is.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides, among other things, an improved process for preparing a stable lyophilized composition comprising mRNA encapsulated in lipid nanoparticles (mRNA-LNPs). Messenger RNAs, which are single stranded, are more structurally liable and unstable than the double stranded DNA or siRNA. It was also estimated that the half-life of the naked double-stranded DNA in the cytosol of mammalian cells is between about 50 and 90 minutes, while the half-life of naked mRNA is reported to be only seconds or less than a second; based on the half-life, mRNA is about 5,500 times more unstable than DNA. Prior art has focused on lyophilization of naked nucleic acids or liposome complexed nucleic acids, which are more stable and not restricted by structural changes. However, lipid nanoparticles encapsulating mRNA have to withstand various forces including temperature and pressure changes that can alter the size, PDI, and encapsulation efficiency of mRNA-LNPs while also preserving mRNA integrity. Therefore, maintaining quality and integrity of mRNA encapsulated in lipid nanoparticles during lyophilization while also maintaining size, PDI, and encapsulation efficiency of mRNA-LNPs is a challenge. The invention is based on the surprising discovery that each step of 1) adding ascorbic acid for lyophilization process, 2) pretreating the mRNA-LNP composition with a buffer to maintain pH prior to the lyophilization process, and 3) increasing and holding the temperature of the lyophilized composition (e.g., during the secondary drying step) to a high temperature (e.g., between 15° C. to 30° C.), can individually and collectively improve integrity of mRNA encapsulated in lipid nanoparticles post-lyophilization. Thus, in one aspect, the present invention provides an improved method of preparing stable lyophilized mRNA with high mRNA integrity for long-term and short-term storages.

Lyophilization Process

Lyophilization or freeze-drying is a process in which water is removed from a product after it is frozen and placed under a vacuum, allowing the ice to change directly from solid to vapor without passing through a liquid phase. The process consists of three separate, unique, and interdependent processes: freezing, primary drying (sublimation), and secondary drying (desorption).

During lyophilization, a sample containing a biomolecule is initially cooled below the freezing point of the solution and accordingly of the water contained therein. As a result, the water freezes. Depending, among other parameters, on temperature, cooling rate (freezing rate), and the time for freezing, crystals may be formed. This exerts physical stress on the biomolecule and other components of the solution, which may lead to a damage of the biomolecule such as—in the case of a nucleic acid-breakage of strands, loss of supercoiling, etc. Furthermore, due to the decrease of volume and loss of the hydration sphere, autocatalytic degradation processes are favored e.g. by traces of transition metals. In addition, the concentration of traces of acids and bases can result in significant changes of the pH value.

Lyophilization involves two types of stress, namely freezing and drying. Both types of stress are known to damage nucleic acids. In the literature, a number of cryoprotectants and lyoprotectants are discussed for lyophilization purposes to prevent these damages. In this context, cryoprotectants are understood as excipients, which allow influencing the structure of the ice and/or the eutectical temperature or glass transition temperature of the mixture. Lyoprotectants are typically excipients, which partially or totally replace the hydration sphere around a molecule and may thus at least partially prevent catalytic and hydrolytic processes. Lyophilization may cause some damage to nucleic acids due to the initial lyophilization process, potentially through changes in the structure, breaks of the nucleic acid chain(s) or the concentration of reactive elements such as contaminating metals.

Pretreatment

Prior to the freezing, the composition for lyophilization is typically "pretreated". Pretreatment includes any method of treating the product prior to freezing. This may include concentrating the product, formulation revision (i.e., addition of components to increase stability, preserve appearance, and/or improve processing), decreasing a high-vapor-pressure solvent, or increasing the surface area.

In some embodiments, a composition comprising mRNA encapsulated in lipid nanoparticles is pretreated prior to freezing. In some embodiments, an aqueous solution comprising mRNA encapsulated in lipid nanoparticles is washed with buffer comprising citrate buffer, EDTA, and trehalose. In some embodiments, an aqueous solution comprising mRNA encapsulated in lipid nanoparticles is washed with buffer comprising 10 mM citrate buffer (pH 7.0), 1 mM EDTA, and 10% trehalose. In some embodiments, an aqueous solution comprising mRNA encapsulated in lipid nanoparticles is washed twice with buffer comprising 10 mM citrate buffer (pH 7.0), 1 mM EDTA, and 10% trehalose.

In some embodiments, ascorbic acid is added to an aqueous solution comprising mRNA encapsulated in lipid nanoparticles prior to freezing. In some embodiments, an aqueous solution comprising mRNA encapsulated in lipid nanoparticles is buffer exchanged into a buffer comprising ascorbic acid. In some embodiments, an aqueous solution comprising mRNA encapsulated in lipid nanoparticles is buffer exchanged into a buffer comprising ascorbic acid and trehalose.

In some embodiments, an aqueous solution comprising mRNA encapsulated in lipid nanoparticles is washed with buffer comprising 10 mM citrate buffer (pH 7.0), 1 mM EDTA, and 10% trehalose, followed by buffer exchange into a buffer comprising 20 mM ascorbic acid and 10% trehalose Freezing Step During the freezing stage, the material is cooled below its triple point, the lowest temperature at which the solid, liquid and gas phases of the material can coexist. This ensures that sublimation rather than melting will occur in the following steps. To facilitate faster and more efficient freeze-drying, larger ice crystals are preferable. The large ice crystals form a network within the product, which promotes faster removal of water vapor during sublimation. To produce larger crystals, the product should be frozen slowly or can be cycled up and down in temperature in a process called annealing. The freezing phase is the most critical in the whole freeze-drying process, as the freezing method can impact the speed of reconstitution, duration of freeze-drying cycle, product stability, and appropriate crystallization.

In some embodiments, an aqueous solution comprising mRNA-LNP is brought to a temperature of between −20° C.-100° C. to obtain a frozen solution. In some embodiments, an aqueous solution comprising mRNA-LNP is brought to a temperature of between −30° C.-60° C. to obtain a frozen solution. In some embodiments, an aqueous solution comprising mRNA-LNP is brought to a temperature of between −40° C.-50° C. to obtain a frozen solution. In some embodiments, an aqueous solution comprising mRNA-LNP is brought to a temperature of about −40° C. to obtain a frozen solution. In some embodiments, an aqueous solution comprising mRNA-LNP is brought to a temperature of about −50° C. to obtain a frozen solution. In some embodiments, an aqueous solution comprising mRNA-LNP is brought to a temperature of about −45° C. to obtain a frozen solution. In some embodiments, an aqueous solution comprising mRNA-LNP is brought to a temperature of about −40° C. to obtain a frozen solution. In some embodiments, the freezing step lasts for about 20 hours. In some embodiments, the freezing step lasts for about 15 hours. In some embodiments, the freezing step lasts for about 12 hours. In some embodiments, the freezing step lasts for about 10 hours. In some embodiments, the freezing step lasts for about 8 hours. In some embodiments, the freezing step lasts for about 5 hours.

Primary Drying Step

During the primary drying phase, the pressure is lowered (to the range of a few millibars), and enough heat is supplied to the material for the ice to sublime. The amount of heat necessary can be calculated using the sublimating molecules' latent heat of sublimation. In this initial drying phase, about 95% of the water in the material is sublimated. In this phase, pressure is controlled through the application of partial vacuum. The vacuum speeds up the sublimation, making it useful as a deliberate drying process. Furthermore, a cold condenser chamber and/or condenser plates provide a surface(s) for the water vapor to re-liquify and solidify on.

In some embodiments, a primary drying step is performed at a temperature below freezing point. In some embodiments, a primary drying step is performed at a temperature of between 0° C. and −100° C. In some embodiments, a primary drying step is performed at a temperature of between −10° C. and −50° C. In some embodiments, a primary drying step is performed at a temperature of between −20° C. and −30° C. In some embodiments, a primary drying step is performed at a temperature of about −30° C. In some embodiments, a primary drying step is performed at a temperature of about −25° C. In some embodiments, a primary drying step is performed at a temperature of about −20° C. In some embodiments, a primary drying step is performed at a temperature of about −15° C. In some embodiments, a primary drying step is performed at a temperature of about −10° C.

In some embodiments, a primary drying step is performed at a pressure below 4580 mTorr (4.58 Torr). In some embodiments, a primary drying step is performed at a pressure of between 0 mTorr and 300 mTorr. In some embodiments, a primary drying step is performed at a pressure of between 10 mTorr and 200 mTorr. In some embodiments, a primary drying step is performed at a pressure of between 20 mTorr and 60 mTorr. In some embodiments, a primary drying step is performed at a pressure of about 100 mTorr. In some embodiments, a primary drying step is performed at a pressure of about 80 mTorr. In some embodiments, a primary drying step is performed at a pressure of about 60 mTorr. In some embodiments, a primary drying step is performed at a pressure of about 50 mTorr. In some embodiments, a primary drying step is performed at a pressure of about 40 mTorr. In some embodiments, a primary drying step is performed at a pressure of about 30 mTorr. In some embodiments, a primary drying step is performed at a pressure of about 20 mTorr.

In some embodiments, a primary drying step is performed for longer than 5 hours. In some embodiments, a primary drying step is performed for longer than 10 hours. In some embodiments, a primary drying step is performed for longer than 15 hours. In some embodiments, a primary drying step is performed for longer than 20 hours. In some embodiments, a primary drying step is performed for longer than 30 hours. In some embodiments, a primary drying step is performed for longer than 50 hours. In some embodiments, a primary drying step is performed for longer than 75 hours. In some embodiments, a primary drying step is performed for longer than 100 hours. In some embodiments, a primary drying step is performed for longer than 110 hours. In some embodiments, a primary drying step is performed for longer than 120 hours. In some embodiments, a primary drying step is performed for longer than 130 hours. In some embodiments, a primary drying step is performed for longer than 140 hours. In some embodiments, a primary drying step is performed for longer than 150 hours. In some embodiments, a primary drying step is performed for longer than 160 hours. In some embodiments, a primary drying step is performed for longer than 170 hours. In some embodiments, a primary drying step is performed for longer than 200 hours.

In some embodiments, a primary drying step is performed for about 10 to 300 hours. In some embodiments, a primary drying step is performed for about 50 to 200 hours. In some embodiments, a primary drying step is performed for about 100 to 150 hours. In some embodiments, a primary drying step is performed for about 120 hours. In some embodiments, a primary drying step is performed for about 130 hours. In some embodiments, a primary drying step is performed for about 140 hours. In some embodiments, a primary drying step is performed for about 150 hours. In some embodiments, a primary drying step is performed for about 160 hours.

Secondary Drying Step

The secondary drying phase aims to remove unfrozen water molecules, since the ice was removed in the primary drying phase. This part of the freeze-drying process is governed by the material's adsorption isotherms. In this phase, the temperature is raised higher than in the primary drying phase, and can even be above 0° C. (32° F.), to break any physico-chemical interactions that have formed between the water molecules and the frozen material. Usually the pressure is also lowered in this stage to encourage desorption (typically in the range of microbars, or fractions of a pascal). Typically, at the end of the secondary drying step of traditional lyophilization process, the moisture content is above 1%, e.g. ~3-4%.

In some embodiments, a secondary drying step is performed at a temperature of between 0° C. and 50° C. In some embodiments, a secondary drying step is performed at a temperature of between 5° C. and 40° C. In some embodiments, a secondary drying step is performed at a temperature of between 20° C. and 30° C. In some embodiments, a secondary drying step is performed at a temperature of about 20° C. In some embodiments, a secondary drying step is performed at a temperature of about 25° C. In some embodiments, a secondary drying step is performed at a temperature of about 30° C. In some embodiments, a secondary drying step is performed at a temperature of about 15° C. In some embodiments, a secondary drying step is performed at a temperature of about 10° C.

In some embodiments, a secondary drying step is performed at a pressure below 4580 mTorr (4.58 Torr). In some embodiments, a secondary drying step is performed at a pressure of between 0 mTorr and 300 mTorr. In some embodiments, a secondary drying step is performed at a pressure of between 10 mTorr and 200 mTorr. In some embodiments, a secondary drying step is performed at a pressure of between 20 mTorr and 60 mTorr. In some embodiments, a secondary drying step is performed at a pressure of about 100 mTorr. In some embodiments, a secondary drying step is performed at a pressure of about 80 mTorr. In some embodiments, a secondary drying step is performed at a pressure of about 60 mTorr. In some embodiments, a secondary drying step is performed at a pressure of about 50 mTorr. In some embodiments, a secondary drying step is performed at a pressure of about 40 mTorr. In some embodiments, a secondary drying step is performed at a pressure of about 30 mTorr. In some embodiments, a secondary drying step is performed at a pressure of about 20 mTorr.

In some embodiments, a secondary drying step is performed for less than 5 hours. In some embodiments, a secondary drying step is performed for less than 10 hours. In some embodiments, a secondary drying step is performed for less than 15 hours. In some embodiments, a secondary drying step is performed for less than 20 hours. In some embodiments, a secondary drying step is performed for less than 30 hours. In some embodiments, a secondary drying step is performed for less than 50 hours.

In some embodiments, a secondary drying step is performed for about 1 to 20 hours. In some embodiments, a secondary drying step is performed for about 3 to 15 hours. In some embodiments, a secondary drying step is performed for about 5 to 12 hours.

In some embodiments, a lyophilized composition comprising one or more lipid nanoparticles encapsulating mRNA comprises less than 3% of moisture content after a secondary drying step. In some embodiments, a lyophilized composition comprising one or more lipid nanoparticles encapsulating mRNA comprises less than 2.5% of moisture content after a secondary drying step. In some embodiments, a lyophilized composition comprising one or more lipid nanoparticles encapsulating mRNA comprises less than 2% of moisture content after a secondary drying step. In some embodiments, a lyophilized composition comprising one or more lipid nanoparticles encapsulating mRNA comprises less than 1% of moisture content after a secondary drying step. In some embodiments, a lyophilized composition comprising one or more lipid nanoparticles encapsulating mRNA comprises less than 0.8% of moisture content after a secondary drying step. In some embodiments, a lyophilized composition comprising one or more lipid nanoparticles encapsulating mRNA comprises less than 0.5% of moisture content after a secondary drying step. In some embodiments, a lyophilized composition comprising one or more lipid nanoparticles encapsulating mRNA comprises less than 0.3% of moisture content after a secondary drying step. In some embodiments, a lyophilized composition comprising one or more lipid nanoparticles encapsulating mRNA comprises about 0.1% to 3% of moisture content after a secondary drying step. In some embodiments, a lyophilized composition comprising one or more lipid nanoparticles encapsulating mRNA comprises about 0.5% to 1% of moisture content after a secondary drying step.

Lyoprotectant and Excipients

Lyoprotectant is a substance that is added to a formulation in order to protect the active ingredient, e.g., mRNA-LNP, during the drying stages. Examples of lyoprotectant are well known in the art. In some embodiment, lyoprotectant is carbohydrates such as glucose, fructose, galactose, sorbose, mannose, and combinations thereof. In some embodiments, lyoprotectant is disaccharides such as lactose, maltose, sucrose, trehalose, cellobiose, and combinations thereof. In some embodiments, lyoprotectant is polysaccharides, such as raffinose, melezitose, maltodextrins, dextrans, dextrins, cellulose, starches, and combinations thereof. In some embodiments, lyoprotectant is alditols, such as glycerol, mannitol, xylitol, maltitol, lactitol, xylitol sorbitol, pyranosyl sorbitol, myoinositol, and combinations thereof. In some embodiments, lyoprotectant is sugar, such as lactose, mannose, mannitol, sucrose, trehalose, or combinations thereof. Generally, a sugar that is preferred in this context, has a high water displacement activity and a high glass transition temperature. Furthermore, a sugar suitable for use is preferably hydrophilic but not hygroscopic. In addition, the sugar preferably has a low tendency to crystallize. In some embodiments, lyoprotectant is trehalose. Furthermore any of the below defined further components may be used as lyoprotectant. Particularly alcohols such as PEG, mannitol, sorbitol, cyclodextran, DMSO, amino acids and proteins such as prolin, glycine, phenylanaline, arginine, serine, albumin and gelatine may be used as lyoprotectant. Additionally metal ions, surfactants and salts as defined below may be used as lyoprotectant. Furthermore, polymers may be used as lyoprotectant, particularly polyvinylpyrrolidone.

In some embodiments, the method comprises adding cryoprotectant. Cryoprotectants are understood as substances that are added to a formulation in order to protect the active ingredient, e.g., mRNA-LNP, during the freezing stages. Examples of cryoprotectants are well known in the art. In some embodiments, cryoprotectant is dimethyl sulfoxide (DMSO). In some embodiments, cryoprotectant is ethylene glycol. In some embodiments, cryoprotectant is glycerol. In some embodiments, cryoprotectant is propylene glycol. In some embodiments, cryoprotectant is 2-methyl-2, 4-pentanediol (MPD). In some embodiments, cryoprotectant is trehalose. In some embodiments, cryoprotectant is formamide, glycerol 3-phosphate, proline, sorbitol, diethyl glycol, sucrose, triethylene glycol, or polymers.

In some embodiments, the method comprises adding an excipient. In some embodiments, the method comprises adding an antioxidant. In some embodiments, the method comprises adding ascorbic acid. In some embodiments, the method comprises adding citric acid. In some embodiments, the method comprises adding methionine. In some embodiments, the method comprises adding tocopherols. In some embodiments, the method comprises adding propyl gallate. In some embodiments, the method comprises adding tertiary butylhydroquinone. In some embodiments, the method comprises adding butylated hydroxyanisole. In some embodiments, the method comprises adding butylated hydroxytolune. In some embodiments, an excipient is added to an aqueous solution prior to the freezing step. In some embodiments, ascorbic is added to an aqueous solution comprising one or more lipid nanoparticles encapsulating mRNA prior to the freezing step.

Characterization of Lyophilized mRNA

The lyophilization methods provided herein result in a stable lyophilized mRNA-LNP composition that has substantially high mRNA integrity and maintains integrity after both short- and long-term storage. As used herein, the term "mRNA integrity" generally refers to the quality of mRNA encapsulated in lipid nanoparticles after lyophilization. mRNA integrity may be determined using methods well known in the art, for example, by RNA agarose gel electrophoresis or Capillary Electrophoresis (CE). In some embodiments, mRNA integrity is determined by CE. In some embodiments, mRNA integrity is determined by Capillary Gel Electrophoresis (CGE). In some embodiments, mRNA integrity is determined by Capillary Zone Electrophoresis (CZE). In some embodiments, mRNA integrity may be determined by banding patterns of RNA agarose gel electrophoresis. In some embodiments, mRNA purified according to present invention shows little or no banding compared to reference band of RNA agarose gel electrophoresis.

RNA Integrity Analysis by Capillary Electrophoresis (CE)

RNA integrity and can be assessed using a Capillary Electrophoresis (CE) by methods known in the art. Briefly, RNA samples are separated electrophoretically, and fragments are detected via UV detection spectrometer or laser-induced fluorescence measurement. The relative amount of full-length or abortive transcripts of synthesized mRNA is determined by the relative peak areas corresponding to the full-length or abortive transcripts.

RNA Integrity Analysis by Capillary Gel Electrophoresis (CGE)

RNA integrity can be assessed using a Capillary Gel Electrophoresis (CGE) by methods known in the art. Briefly, RNA samples are separated on a gel. Then, the gels are analyzed to determine whether the banding pattern and apparent nucleotide length is consistent with an analytical reference standard.

In some embodiments, an mRNA integrity of the lyophilized composition is about or higher than 20% upon storage at a temperature of between 2° C. and 8° C. for longer than one month. In some embodiments, an mRNA integrity of the lyophilized composition is about or higher than 30% upon storage at a temperature of between 2° C. and 8° C. for longer than one month. In some embodiments, an mRNA integrity of the lyophilized composition is about or higher than 40% upon storage at a temperature of between 2° C. and 8° C. for longer than one month. In some embodiments, an mRNA integrity of the lyophilized composition is about or higher than 45% upon storage at a temperature of between 2° C. and 8° C. for longer than one month. In some embodiments, an mRNA integrity of the lyophilized composition is about or higher than 50% upon storage at a temperature of between 2° C. and 8° C. for longer than one month. In some embodiments, an mRNA integrity of the lyophilized composition is about or higher than 55% upon storage at a temperature of between 2° C. and 8° C. for longer than one month. In some embodiments, an mRNA integrity of the lyophilized composition is about or higher than 60% upon storage at a temperature of between 2° C. and 8° C. for longer than one month. In some embodiments, an mRNA integrity of the lyophilized composition is about or higher than 65% upon storage at a temperature of between 2° C. and 8° C. for longer than one month. In some embodiments, an mRNA integrity of the lyophilized composition is about or higher than 70% upon storage at a temperature of between 2° C. and 8° C. for longer than one month. In some embodiments, an mRNA integrity of the lyophilized composition is about or higher than 80% upon storage at a temperature of between 2° C. and 8° C. for longer than one month.

In some embodiments, an mRNA integrity of the lyophilized composition is about or higher than 20% upon storage at a temperature of between 2° C. and 8° C. for longer than two months. In some embodiments, an mRNA integrity of the lyophilized composition is about or higher than 30% upon storage at a temperature of between 2° C. and 8° C. for longer than two months. In some embodiments, an mRNA integrity of the lyophilized composition is about or higher than 40% upon storage at a temperature of between 2° C. and 8° C. for longer than two months. In some embodiments, an mRNA integrity of the lyophilized composition is about or higher than 45% upon storage at a temperature of between 2° C. and 8° C. for longer than two months. In some embodiments, an mRNA integrity of the lyophilized composition is about or higher than 50% upon storage at a temperature of between 2° C. and 8° C. for longer than two months. In some embodiments, an mRNA integrity of the lyophilized composition is about or higher than 55% upon storage at a temperature of between 2° C. and 8° C. for longer than two months. In some embodiments, an mRNA integrity of the lyophilized composition is about or higher than 60% upon storage at a temperature of between 2° C. and 8° C. for longer than two months. In some embodiments, an mRNA integrity of the lyophilized composition is about or higher than 65% upon storage at a temperature of between 2° C. and 8° C. for longer than two months. In some embodiments, an mRNA integrity of the lyophilized composition is about or higher than 70% upon storage at a temperature of between 2° C. and 8° C. for longer than two months. In some embodiments, an mRNA integrity of the lyophilized composition is about or higher than 80% upon storage at a temperature of between 2° C. and 8° C. for longer than two months.

In some embodiments, an mRNA integrity of the lyophilized composition is about or higher than 20% upon storage at a temperature of between 2° C. and 8° C. for longer than three months. In some embodiments, an mRNA integrity of the lyophilized composition is about or higher than 30% upon storage at a temperature of between 2° C. and 8° C. for longer than three months. In some embodiments, an mRNA integrity of the lyophilized composition is about or higher than 40% upon storage at a temperature of between 2° C. and 8° C. for longer than three months. In some embodiments, an mRNA integrity of the lyophilized composition is about or higher than 45% upon storage at a temperature of between 2° C. and 8° C. for longer than three months. In some embodiments, an mRNA integrity of the lyophilized composition is about or higher than 50% upon storage at a temperature of between 2° C. and 8° C. for longer than three months. In some embodiments, an mRNA integrity of the lyophilized composition is about or higher than 55% upon storage at a temperature of between 2° C. and 8° C. for longer than three months. In some embodiments, an mRNA integrity of the lyophilized composition is about or higher than 60% upon storage at a temperature of between 2° C. and 8° C. for longer than three months. In some embodiments, an mRNA integrity of the lyophilized composition is about or higher than 65% upon storage at a temperature of between 2° C. and 8° C. for longer than three months. In some embodiments, an mRNA integrity of the lyophilized composition is about or higher than 70% upon storage at a temperature of between 2° C. and 8° C. for longer than three months. In some embodiments, an mRNA integrity of the lyophilized composition is about or higher than 80% upon storage at a temperature of between 2° C. and 8° C. for longer than three months.

In some embodiments, an mRNA integrity of the lyophilized composition is about or higher than 20% upon storage at a temperature of between 2° C. and 8° C. for longer than five months. In some embodiments, an mRNA integrity of the lyophilized composition is about or higher than 30% upon storage at a temperature of between 2° C. and 8° C. for longer than five months. In some embodiments, an mRNA integrity of the lyophilized composition is about or higher than 40% upon storage at a temperature of between 2° C. and 8° C. for longer than five months. In some embodiments, an mRNA integrity of the lyophilized composition is about or higher than 45% upon storage at a temperature of between 2° C. and 8° C. for longer than five months. In some embodiments, an mRNA integrity of the lyophilized composition is about or higher than 50% upon storage at a temperature of between 2° C. and 8° C. for longer than five months. In some embodiments, an mRNA integrity of the lyophilized composition is about or higher than 55% upon storage at a temperature of between 2° C. and 8° C. for longer than five months. In some embodiments, an mRNA integrity of the lyophilized composition is about or higher than 60% upon storage at a temperature of between 2° C. and 8° C. for longer than five months. In some embodiments, an mRNA integrity of the lyophilized composition is about or higher than 65% upon storage at a temperature of between 2° C. and 8° C. for longer than five months. In some embodiments, an mRNA integrity of the lyophilized composition is about or higher than 70% upon storage at a temperature of between 2° C. and 8° C. for longer than five months. In some embodiments, an mRNA integrity of the lyophilized composition is about or higher than 80% upon storage at a temperature of between 2° C. and 8° C. for longer than five months.

In some embodiments, an mRNA integrity of the lyophilized composition is about or higher than 20% upon storage at a temperature of between 2° C. and 8° C. for longer than six months. In some embodiments, an mRNA integrity of the lyophilized composition is about or higher than 30% upon storage at a temperature of between 2° C. and 8° C. for longer than six months. In some embodiments, an mRNA integrity of the lyophilized composition is about or higher than 40% upon storage at a temperature of between 2° C. and 8° C. for longer than six months. In some embodiments, an mRNA integrity of the lyophilized composition is about or higher than 45% upon storage at a temperature of between 2° C. and 8° C. for longer than six months. In some embodiments, an mRNA integrity of the lyophilized composition is about or higher than 50% upon storage at a temperature of between 2° C. and 8° C. for longer than six months. In some embodiments, an mRNA integrity of the lyophilized composition is about or higher than 55% upon storage at a temperature of between 2° C. and 8° C. for longer than six months. In some embodiments, an mRNA integrity of the lyophilized composition is about or higher than 60% upon storage at a temperature of between 2° C. and 8° C. for longer than six months. In some embodiments, an mRNA integrity of the lyophilized composition is about or higher than 65% upon storage at a temperature of between 2° C. and 8° C. for longer than six months. In some embodiments, an mRNA integrity of the lyophilized composition is about or higher than 70% upon storage at a temperature of between 2° C. and 8° C. for longer than six months. In some embodiments, an mRNA integrity of the lyophilized composition is about or higher than 80% upon storage at a temperature of between 2° C. and 8° C. for longer than six months.

In some embodiments, an mRNA integrity of the lyophilized composition is about or higher than 20% upon storage at a temperature of between 2° C. and 8° C. for longer than one year. In some embodiments, an mRNA integrity of the lyophilized composition is about or higher than 30% upon storage at a temperature of between 2° C. and 8° C. for longer than one year. In some embodiments, an mRNA integrity of the lyophilized composition is about or higher than 40% upon storage at a temperature of between 2° C. and 8° C. for longer than one year. In some embodiments, an mRNA integrity of the lyophilized composition is about or higher than 45% upon storage at a temperature of between 2° C. and 8° C. for longer than one year. In some embodiments, an mRNA integrity of the lyophilized composition is about or higher than 50% upon storage at a temperature of between 2° C. and 8° C. for longer than one year. In some embodiments, an mRNA integrity of the lyophilized composition is about or higher than 55% upon storage at a temperature of between 2° C. and 8° C. for longer than one year. In some embodiments, an mRNA integrity of the lyophilized composition is about or higher than 60% upon storage at a temperature of between 2° C. and 8° C. for longer than one year. In some embodiments, an mRNA integrity of the lyophilized composition is about or higher than 65% upon storage at a temperature of between 2° C. and 8° C. for longer than one year. In some embodiments, an mRNA integrity of the lyophilized composition is about or higher than 70% upon storage at a temperature of between 2° C. and 8° C. for longer than one year. In some embodiments, an mRNA integrity of the lyophilized composition is about or higher than 80% upon storage at a temperature of between 2° C. and 8° C. for longer than one year.

In some embodiments, an mRNA integrity of the lyophilized composition is about or higher than 20% upon storage at a room temperature (e.g., between 15° C. and 25° C.) for longer than three days. In some embodiments, an mRNA integrity of the lyophilized composition is about or higher than 20% upon storage at a temperature of between 15° C. and 25° C. for longer than three days. In some embodiments, an mRNA integrity of the lyophilized composition is about or higher than 30% upon storage at a temperature of between 15° C. and 25° C. for longer than three days. In some embodiments, an mRNA integrity of the lyophilized composition is about or higher than 40% upon storage at a temperature of between 15° C. and 25° C. for longer than three days. In some embodiments, an mRNA integrity of the lyophilized composition is about or higher than 45% upon storage at a temperature of between 15° C. and 25° C. for longer than three days. In some embodiments, an mRNA integrity of the lyophilized composition is about or higher than 50% upon storage at a temperature of between 15° C. and 25° C. for longer than three days. In some embodiments, an mRNA integrity of the lyophilized composition is about or higher than 55% upon storage at a temperature of between 15° C. and 25° C. for longer than three days. In some embodiments, an mRNA integrity of the lyophilized composition is about or higher than 60% upon storage at a temperature of between 15° C. and 25° C. for longer than three days. In some embodiments, an mRNA integrity of the lyophilized composition is about or higher than 65% upon storage at a temperature of between 15° C. and 25° C. for longer than three days. In some embodiments, an mRNA integrity of the lyophilized composition is about or higher than 70% upon storage at a temperature of between 15° C. and 25° C. for longer than three days.

In some embodiments, an mRNA integrity of the lyophilized composition is about or higher than 20% upon storage at a room temperature (e.g., between 15° C. and 25° C.) for longer than one week. In some embodiments, an mRNA integrity of the lyophilized composition is about or higher than 20% upon storage at a temperature of between 15° C. and 25° C. for longer than one week. In some embodiments, an mRNA integrity of the lyophilized composition is about or higher than 30% upon storage at a temperature of between 15° C. and 25° C. for longer than one week. In some embodiments, an mRNA integrity of the lyophilized composition is about or higher than 40% upon storage at a temperature of between 15° C. and 25° C. for longer than one week. In some embodiments, an mRNA integrity of the lyophilized composition is about or higher than 45% upon storage at a temperature of between 15° C. and 25° C. for longer than one week. In some embodiments, an mRNA integrity of the lyophilized composition is about or higher than 50% upon storage at a temperature of between 15° C. and 25° C. for longer than one week. In some embodiments, an mRNA integrity of the lyophilized composition is about or higher than 55% upon storage at a temperature of between 15° C. and 25° C. for longer than one week. In some embodiments, an mRNA integrity of the lyophilized composition is about or higher than 60% upon storage at a temperature of between 15° C. and 25° C. for longer than one week. In some embodiments, an mRNA integrity of the lyophilized composition is about or higher than 65% upon storage at a temperature of between 15° C. and 25° C. for longer than one week. In some embodiments, an mRNA integrity of the lyophilized composition is about or higher than 70% upon storage at a temperature of between 15° C. and 25° C. for longer than one week.

In some embodiments, an mRNA integrity of the lyophilized composition is about or higher than 20% upon storage at a room temperature (e.g., between 15° C. and 25° C.) for longer than two weeks. In some embodiments, an mRNA integrity of the lyophilized composition is about or higher than 20% upon storage at a temperature of between 15° C. and 25° C. for longer than two weeks. In some embodiments, an mRNA integrity of the lyophilized composition is about or higher than 30% upon storage at a temperature of between 15° C. and 25° C. for longer than two weeks. In some embodiments, an mRNA integrity of the lyophilized composition is about or higher than 40% upon storage at a temperature of between 15° C. and 25° C. for longer than two weeks. In some embodiments, an mRNA integrity of the lyophilized composition is about or higher than 45% upon storage at a temperature of between 15° C. and 25° C. for longer than two weeks. In some embodiments, an mRNA integrity of the lyophilized composition is about or higher than 50% upon storage at a temperature of between 15° C. and 25° C. for longer than two weeks. In some embodiments, an mRNA integrity of the lyophilized composition is about or higher than 55% upon storage at a temperature of between 15° C. and 25° C. for longer than two weeks. In some embodiments, an mRNA integrity of the lyophilized composition is about or higher than 60% upon storage at a temperature of between 15° C. and 25° C. for longer than two weeks. In some embodiments, an mRNA integrity of the lyophilized composition is about or higher than 65% upon storage at a temperature of between 15° C. and 25° C. for longer than two weeks. In some embodiments, an mRNA integrity of the lyophilized composition is about or higher than 70% upon storage at a temperature of between 15° C. and 25° C. for longer than two weeks.

In some embodiments, an mRNA integrity of the lyophilized composition is about or higher than 20% upon storage at a room temperature (e.g., between 15° C. and 25° C.) for longer than three weeks. In some embodiments, an mRNA integrity of the lyophilized composition is about or higher than 20% upon storage at a temperature of between 15° C. and 25° C. for longer than three weeks. In some embodiments, an mRNA integrity of the lyophilized composition is about or higher than 30% upon storage at a temperature of between 15° C. and 25° C. for longer than three weeks. In some embodiments, an mRNA integrity of the lyophilized composition is about or higher than 40% upon storage at a temperature of between 15° C. and 25° C. for longer than three weeks. In some embodiments, an mRNA integrity of the lyophilized composition is about or higher than 45% upon storage at a temperature of between 15° C. and 25° C. for longer than three weeks. In some embodiments, an mRNA integrity of the lyophilized composition is about or higher than 50% upon storage at a temperature of between 15° C. and 25° C. for longer than three weeks. In some embodiments, an mRNA integrity of the lyophilized composition is about or higher than 55% upon storage at a temperature of between 15° C. and 25° C. for longer than three weeks. In some embodiments, an mRNA integrity of the lyophilized composition is about or higher than 60% upon storage at a temperature of between 15° C. and 25° C. for longer than three weeks. In some embodiments, an mRNA integrity of the lyophilized composition is about or higher than 65% upon storage at a temperature of between 15° C. and 25° C. for longer than three weeks. In some embodiments, an mRNA integrity of the lyophilized composition is about or higher than 70% upon storage at a temperature of between 15° C. and 25° C. for longer than three weeks.

In some embodiments, an mRNA integrity of the lyophilized composition is about or higher than 20% upon storage at a room temperature (e.g., between 15° C. and 25° C.) for longer than four weeks. In some embodiments, an mRNA integrity of the lyophilized composition is about or higher than 20% upon storage at a temperature of between 15° C. and 25° C. for longer than four weeks. In some embodiments, an mRNA integrity of the lyophilized composition is about or higher than 30% upon storage at a temperature of between 15° C. and 25° C. for longer than four weeks. In some embodiments, an mRNA integrity of the lyophilized composition is about or higher than 40% upon storage at a temperature of between 15° C. and 25° C. for longer than four weeks. In some embodiments, an mRNA integrity of the lyophilized composition is about or higher than 45% upon storage at a temperature of between 15° C. and 25° C. for longer than four weeks. In some embodiments, an mRNA integrity of the lyophilized composition is about or higher than 50% upon storage at a temperature of between 15° C. and 25° C. for longer than four weeks. In some embodiments, an mRNA integrity of the lyophilized composition is about or higher than 55% upon storage at a temperature of between 15° C. and 25° C. for longer than four weeks. In some embodiments, an mRNA integrity of the lyophilized composition is about or higher than 60% upon storage at a temperature of between 15° C. and 25° C. for longer than four weeks. In some embodiments, an mRNA integrity of the lyophilized composition is about or higher than 65% upon storage at a temperature of between 15° C. and 25° C. for longer than four weeks. In some embodiments, an mRNA integrity of the lyophilized composition is about or higher than 70% upon storage at a temperature of between 15° C. and 25° C. for longer than four weeks.

In some embodiments, an mRNA integrity of the lyophilized composition is about or higher than 20% upon storage at a room temperature (e.g., between 15° C. and 25° C.) for longer than five weeks. In some embodiments, an mRNA integrity of the lyophilized composition is about or higher than 20% upon storage at a temperature of between 15° C. and 25° C. for longer than five weeks. In some embodiments, an mRNA integrity of the lyophilized composition is about or higher than 30% upon storage at a temperature of between 15° C. and 25° C. for longer than five weeks. In some embodiments, an mRNA integrity of the lyophilized composition is about or higher than 40% upon storage at a temperature of between 15° C. and 25° C. for longer than five weeks. In some embodiments, an mRNA integrity of the lyophilized composition is about or higher than 45% upon storage at a temperature of between 15° C. and 25° C. for longer than five weeks. In some embodiments, an mRNA integrity of the lyophilized composition is about or higher than 50% upon storage at a temperature of between 15° C. and 25° C. for longer than five weeks. In some embodiments, an mRNA integrity of the lyophilized composition is about or higher than 55% upon storage at a temperature of between 15° C. and 25° C. for longer than five weeks. In some embodiments, an mRNA integrity of the lyophilized composition is about or higher than 60% upon storage at a temperature of between 15° C. and 25° C. for longer than five weeks. In some embodiments, an mRNA integrity of the lyophilized composition is about or higher than 65% upon storage at a temperature of between 15° C. and 25° C. for longer than five weeks. In some embodiments, an mRNA integrity of the lyophilized composition is about or higher than 70% upon storage at a temperature of between 15° C. and 25° C. for longer than five weeks.

mRNA Synthesis mRNAs according to the present invention may be synthesized according to any of a variety of known methods. Various methods are described in published U.S. Application No. US 2018/0258423, and can be used to practice the present invention, all of which are incorporated herein by reference. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

In some embodiments, a suitable mRNA sequence is an mRNA sequence encoding a protein or a peptide. In some embodiments, a suitable mRNA sequence is codon optimized for efficient expression human cells. In some embodiments, a suitable mRNA sequence is naturally-occurring or a wild-type sequence. In some embodiments, a suitable mRNA sequence encodes a protein or a peptide that contains one or mutations in amino acid sequence.

The present invention may be used to prepare stable lyophilized mRNA of a variety of lengths. In some embodiments, the present invention may be used to deliver in vitro synthesized mRNA of or greater than about 0.5 kb, 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, 20 kb, 30 kb, 40 kb, or 50 kb in length. In some embodiments, the present invention may be used to deliver in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-50 kb in length.

In some embodiments, for the preparation of mRNA according to the invention, a DNA template is transcribed in vitro. A suitable DNA template typically has a promoter, for example, a T3, T7 or SP6 promoter, for in vitro transcription, followed by desired nucleotide sequence for desired mRNA and a termination signal.

Nucleotides

Various naturally-occurring or modified nucleosides may be used to produce mRNA according to the present invention. In some embodiments, an mRNA is or comprises naturally-occurring nucleosides (or unmodified nucleotides; e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose): and/or modified phosphate groups (e.g., phosphorothioates and 5'-N-phosphoramidite linkages).

In some embodiments, a suitable mRNA may contain backbone modifications, sugar modifications and/or base modifications. For example, modified nucleotides may include, but not be limited to, modified purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, the mRNA comprises one or more nonstandard nucleotide residues. The nonstandard nucleotide residues may include, e.g., 5-methyl-cytidine ("5mC"), pseudouridine ("ψU"), and/or 2-thio-uridine ("2sU"). See, e.g., U.S. Pat. No. 8,278,036 or WO 2011/012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US 2012/0195936 and international publication WO 2011/012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g., cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published U.S. Application No. US 2016/0032356 and published U.S. Application No. US 2018/0125989, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and for chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol: chloroform: isoamyl alcohol solution, well known to one of skill in the art. In some embodiments, the mRNA is purified using Tangential Flow Filtration. Suitable purification methods include those described in published U.S. Application No. US 2016/0040154, published U.S. Application No. US 2015/0376220, published U.S. Application No. US 2018/0251755, published U.S. Application No. US 2018/0251754, U.S. Provisional Application No. 62/757,612 filed on Nov. 8, 2018, and U.S. Provisional Application No. 62/891,781 filed on Aug. 26, 2019, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of Purified mRNA

The mRNA composition described herein is substantially free of contaminants comprising short abortive RNA species, long abortive RNA species, double-stranded RNA (dsRNA), residual plasmid DNA, residual in vitro transcription enzymes, residual solvent and/or residual salt.

The mRNA composition described herein has a purity of about between 60% and about 100%. Accordingly, in some embodiments, the purified mRNA has a purity of about 60%. In some embodiments, the purified mRNA has a purity of about 6.5%. In some embodiments, the purified mRNA has a purity of about 70%. In some embodiments, the purified mRNA has a purity of about 75%. In some embodiments, the purified mRNA has a purity of about 80%. In some embodiments, the purified mRNA has a purity of about 85%. In some embodiments, the purified mRNA has a purity of about 90%. In some embodiments, the purified mRNA has a purity of about 91%. In some embodiments, the purified mRNA has a purity of about 92%. In some embodiments, the purified mRNA has a purity of about 93%. In some embodiments, the purified mRNA has a purity of about 94%. In some embodiments, the purified mRNA has a purity of about 95%. In some embodiments, the purified mRNA has a purity of about 96%. In some embodiments, the purified mRNA has a purity of about 97%. In some embodiments, the purified mRNA has a purity of about 98%. In some embodiments, the purified mRNA has a purity of about 99%. In some embodiments, the purified mRNA has a purity of about 100%.

In some embodiments, the mRNA composition described herein has less than 10%, less than 9%, less than 8%, less than 7%, less than 6%, less than 5%, less than 4%, less than 3%, less than 2%, less than 1%, less than 0.5%, and/or less than 0.1% impurities other than full-length mRNA. The impurities include IVT contaminants, e.g., proteins, enzymes, DNA templates, free nucleotides, residual solvent, residual salt, double-stranded RNA (dsRNA), prematurely aborted RNA sequences ("shortmers" or "short abortive RNA species"), and/or long abortive RNA species. In some embodiments, the purified mRNA is substantially free of process enzymes.

In some embodiments, the residual plasmid DNA in the purified mRNA of the present invention is less than about 1 pg/mg, less than about 2 pg/mg, less than about 3 pg/mg, less than about 4 pg/mg, less than about 5 pg/mg, less than about 6 pg/mg, less than about 7 pg/mg, less than about 8 pg/mg, less than about 9 pg/mg, less than about 10 pg/mg, less than about 11 pg/mg, or less than about 12 pg/mg. Accordingly, the residual plasmid DNA in the purified mRNA is less than about 1 pg/mg. In some embodiments, the residual plasmid DNA in the purified mRNA is less than about 2 pg/mg. In some embodiments, the residual plasmid DNA in the purified mRNA is less than about 3 pg/mg. In some embodiments, the residual plasmid DNA in the purified mRNA is less than about 4 pg/mg. In some embodiments, the residual plasmid DNA in the purified mRNA is less than about 5 pg/mg. In some embodiments, the residual plasmid DNA in the purified mRNA is less than about 6 pg/mg. In some embodiments, the residual plasmid DNA in the purified mRNA is less than about 7 pg/mg. In some embodiments, the residual plasmid DNA in the purified mRNA is less than about 8 pg/mg. In some embodiments, the residual plasmid DNA in the purified mRNA is less than about 9 pg/mg. In some embodiments, the residual plasmid DNA in the purified mRNA is less than about 10 pg/mg. In some embodiments, the residual plasmid DNA in the purified mRNA is less than about 11 pg/mg. In some embodiments, the residual plasmid DNA in the purified mRNA is less than about 12 pg/mg.

Delivery Vehicles

According to the present invention, mRNA encoding a protein or a peptide (e.g., a full length, fragment, or portion of a protein or a peptide) as described herein may be delivered in a lipid nanoparticle.

In some embodiments, mRNAs encoding at least one protein or peptide may be delivered via a single delivery vehicle. In some embodiments, mRNAs encoding at least one protein or peptide may be delivered via one or more delivery vehicles each of a different composition. In some embodiments, the one or more mRNAs and/or are encapsulated within the same lipid nanoparticles. In some embodiments, the one or more mRNAs are encapsulated within separate lipid nanoparticles. In some embodiments, lipid nanoparticles are empty.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired nucleic acid (e.g., mRNA) to a target cell or tissue. In some embodiments, a nanoparticle delivery vehicle is a liposome. In some embodiments, a liposome comprises one or more cationic lipids, one or more non-cationic lipids, one or more cholesterol-based lipids, or one or more PEG-modified lipids. In some embodiments, a liposome comprises no more than three distinct lipid components. In some embodiments, one distinct lipid component is a sterol-based cationic lipid.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of.

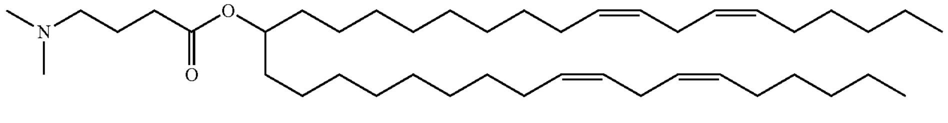 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

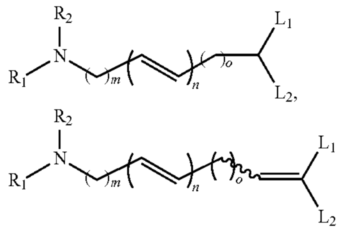

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

(HGT-5000)

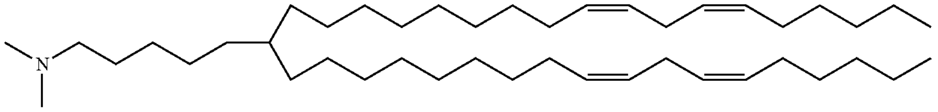

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

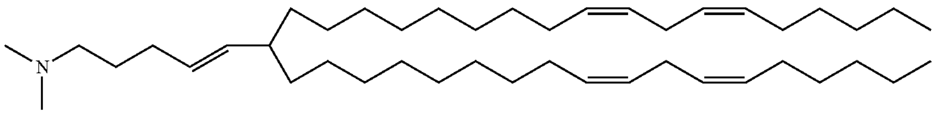

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

(HGT-5002)

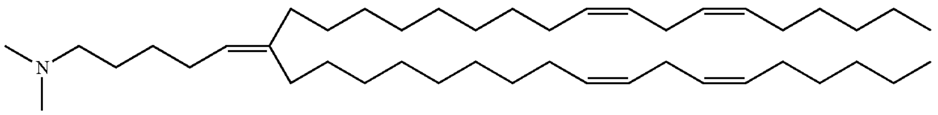

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

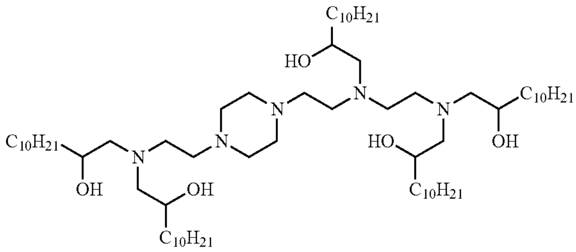

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

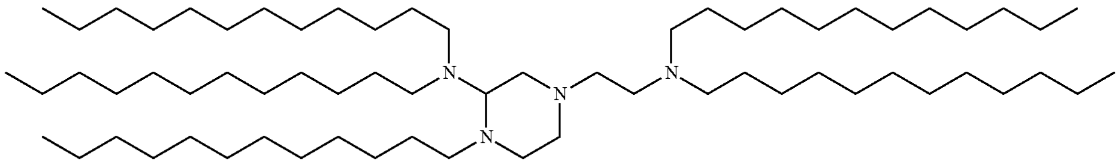 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

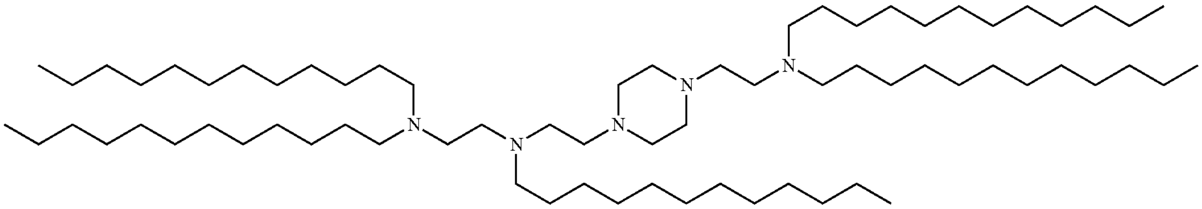 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

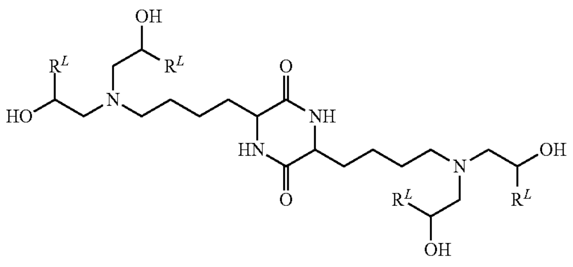

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

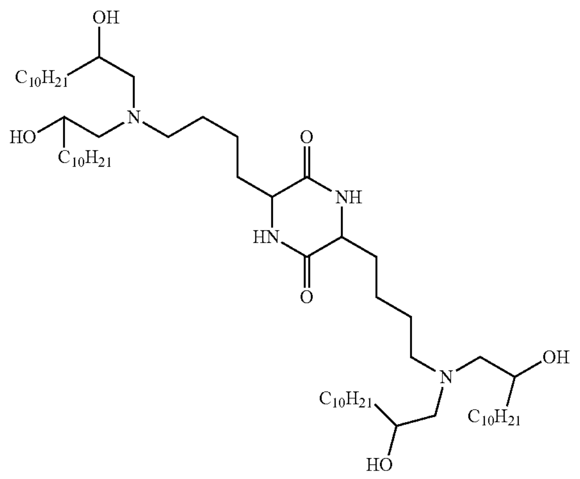

and pharmaceutically acceptable salts thereof. In certain embodiments, the compositions and methods of the present invention include a cationic lipid having a compound structure of:

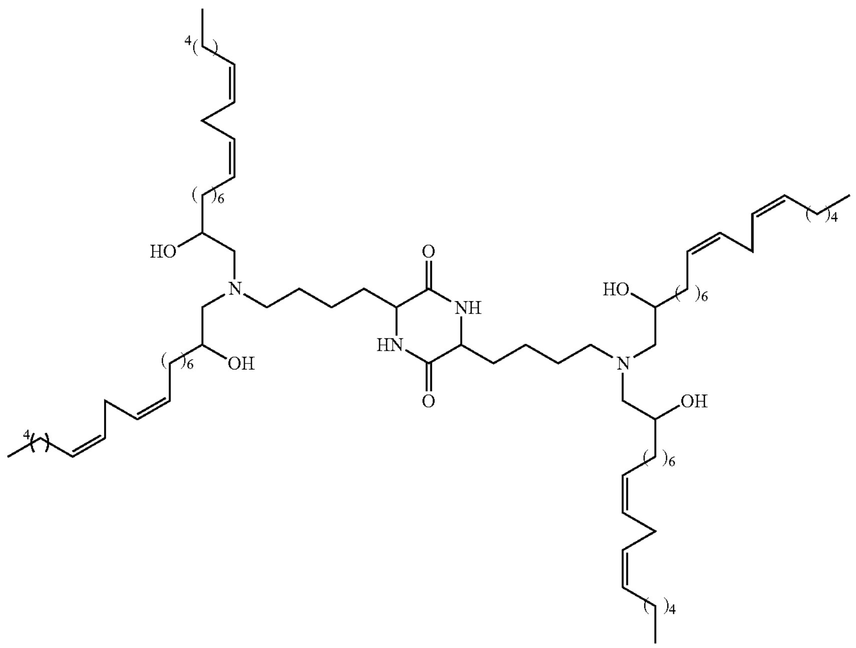

and pharmaceutically acceptable salts thereof. In certain embodiments, the compositions and methods of the present invention include a cationic lipid having a compound structure of:

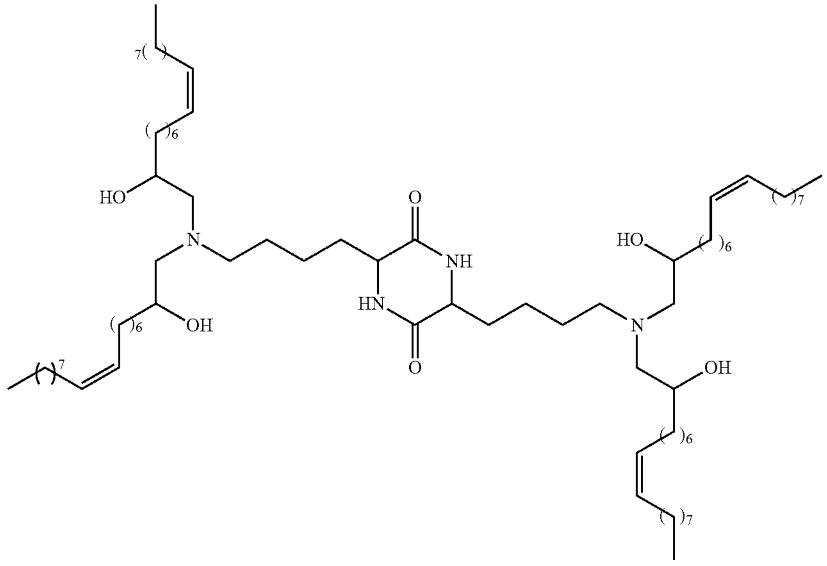

and pharmaceutically acceptable salts thereof. In certain embodiments, the compositions and methods of the present invention include a cationic lipid having a compound structure of:

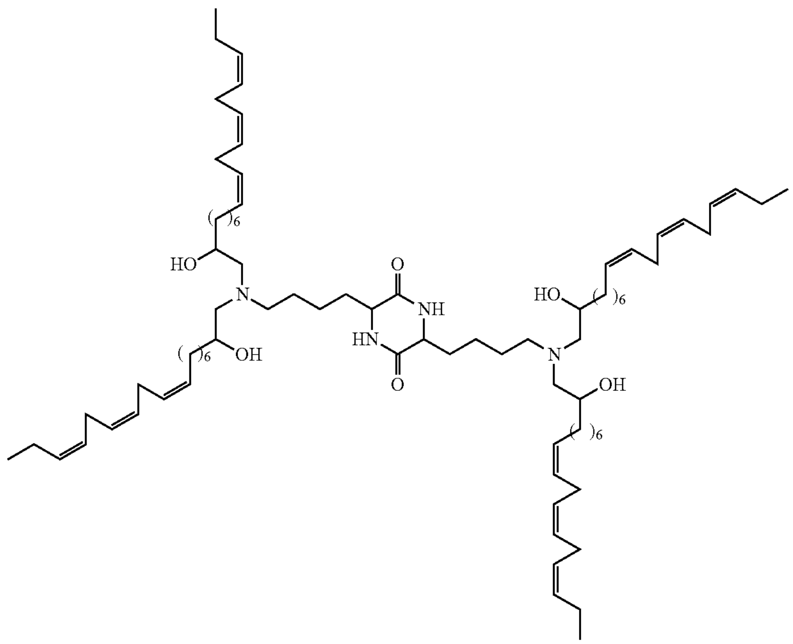

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

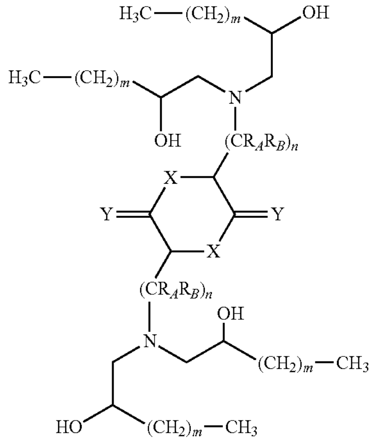

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each RB is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

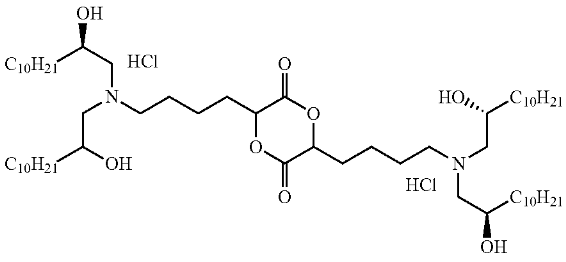

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

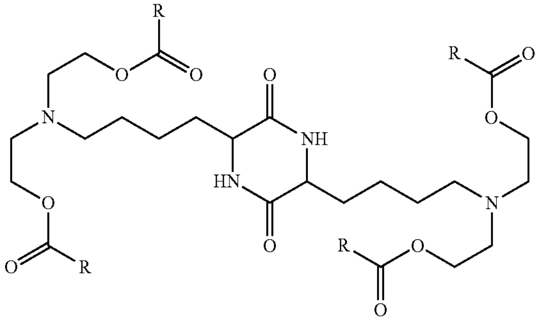

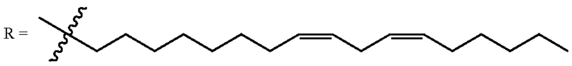

or a pharmaceutically acceptable salt thereof. In some embodiments, the compositions and methods of the present invention include a cationic lipid having the compound structure:

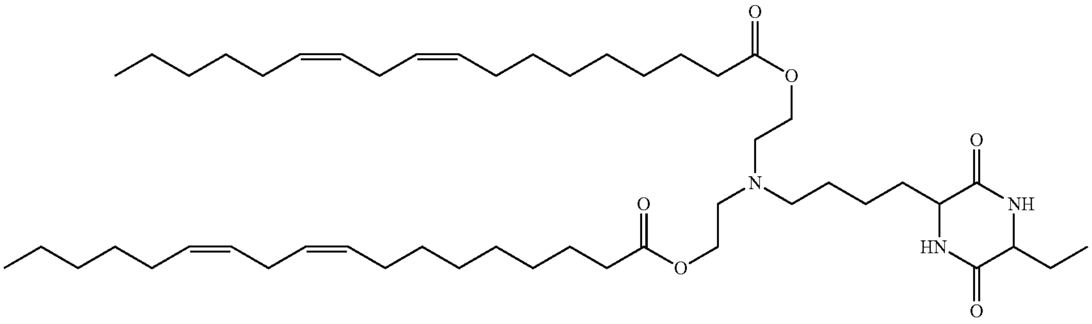 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

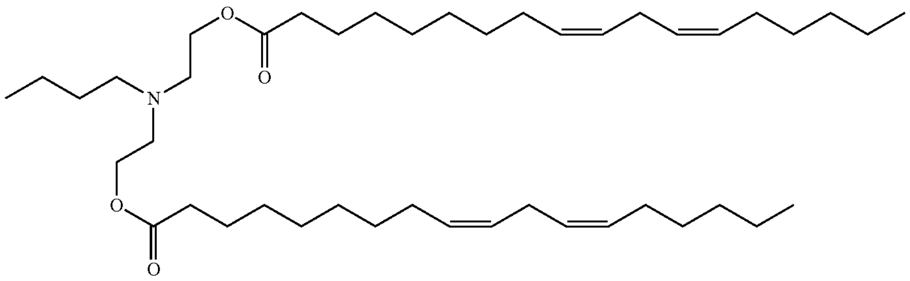 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

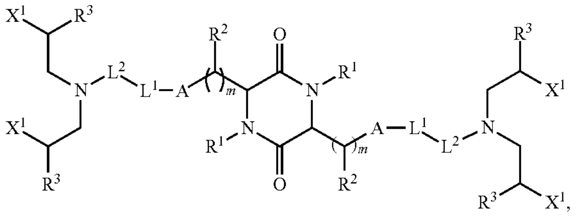

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

(Compound 1)

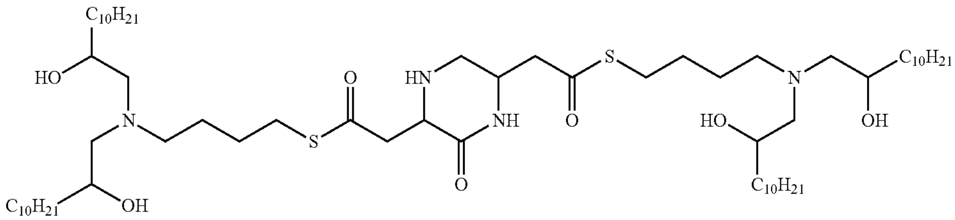

or a pharmaceutically acceptable salt thereof. In some embodiments, the compositions and methods of the present invention include a cationic lipid of the following formula:

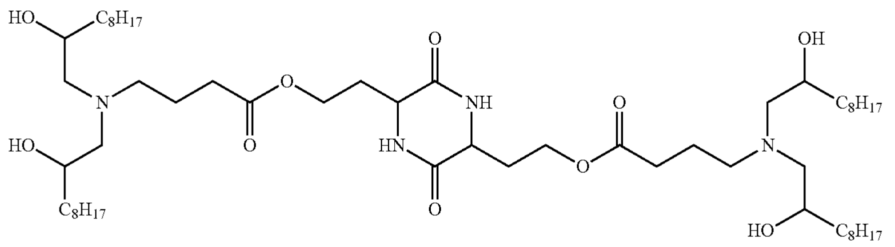

or a pharmaceutically acceptable salt thereof. In some embodiments, the compositions and methods of the present invention include a cationic lipid of the following formula:

(Compound 3)

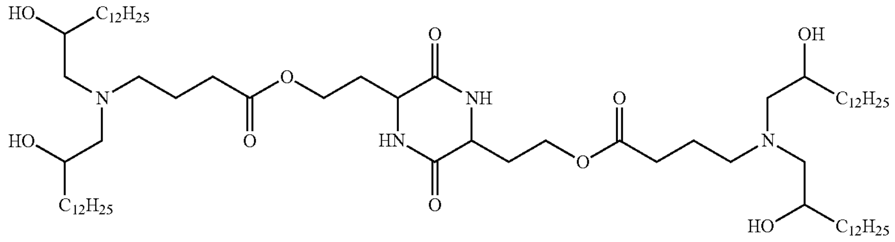

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

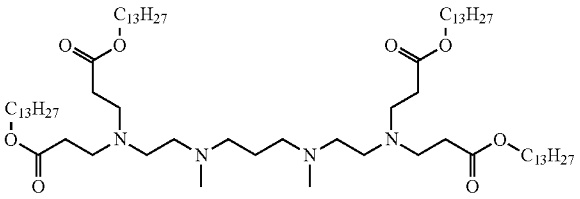

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

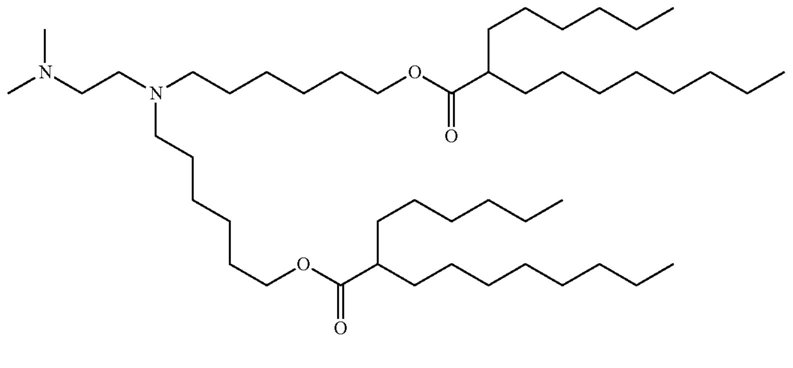 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

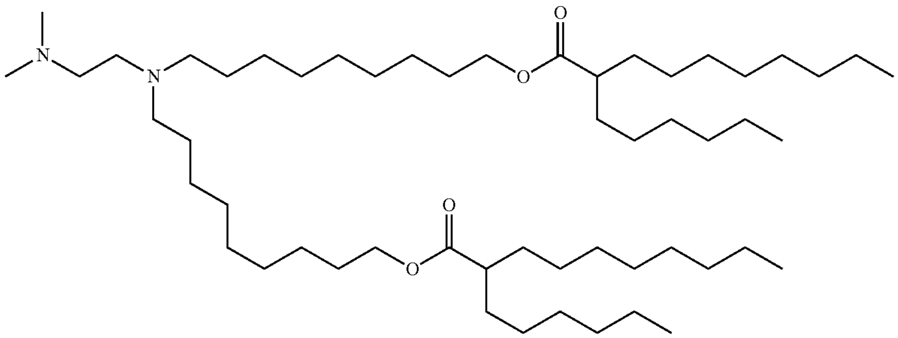 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

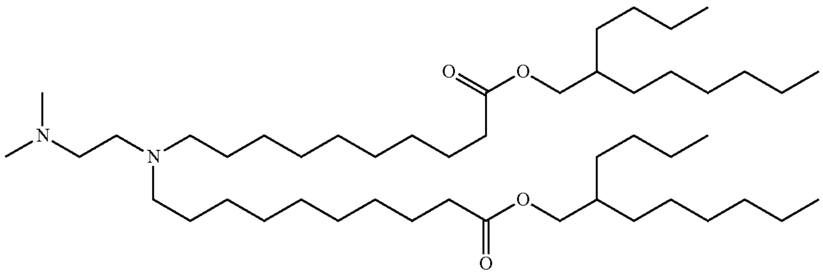 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

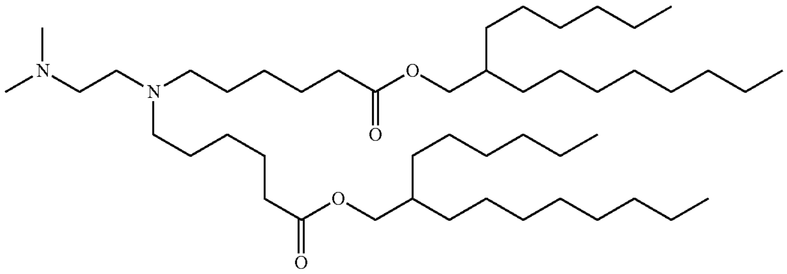 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

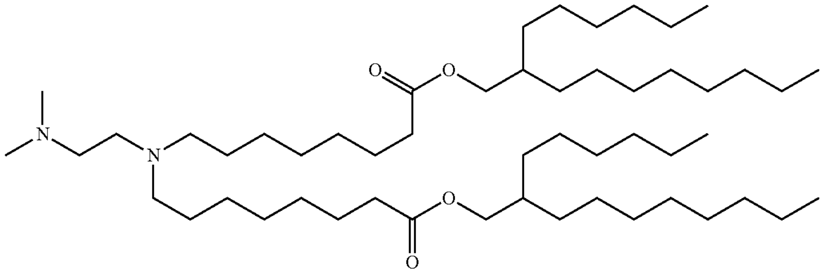 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

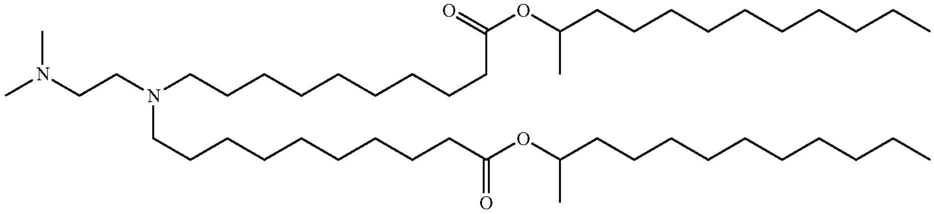 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

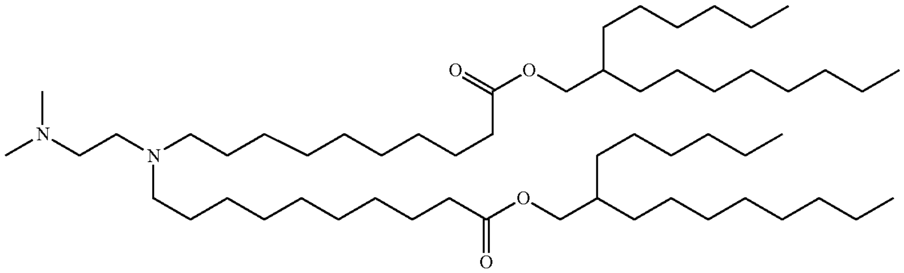 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

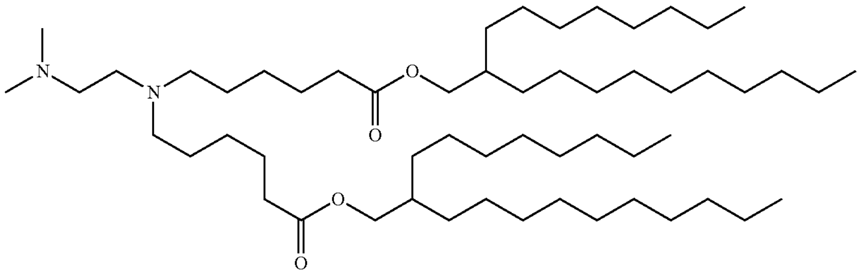 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

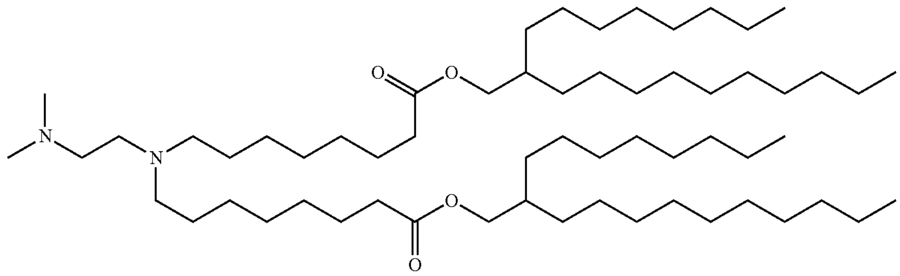 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

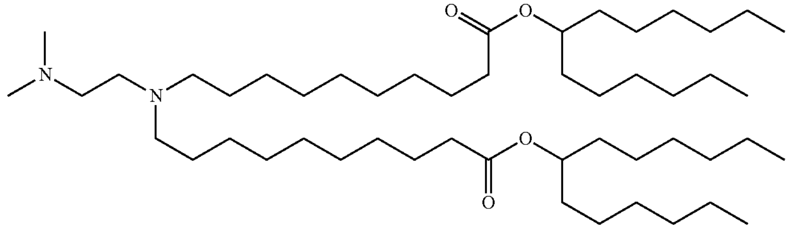 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

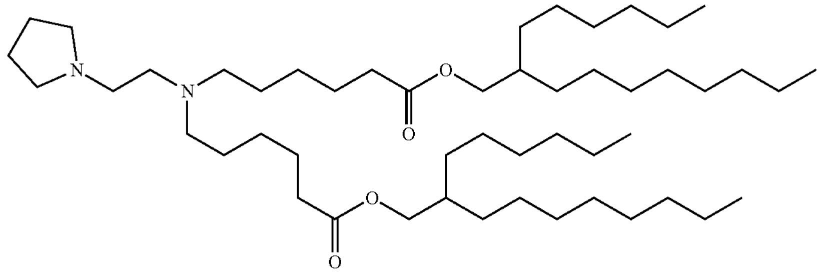 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

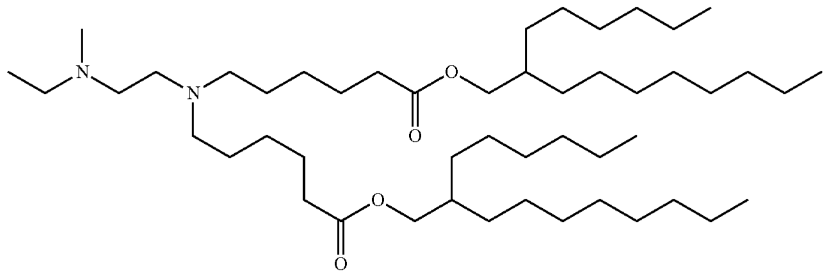 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

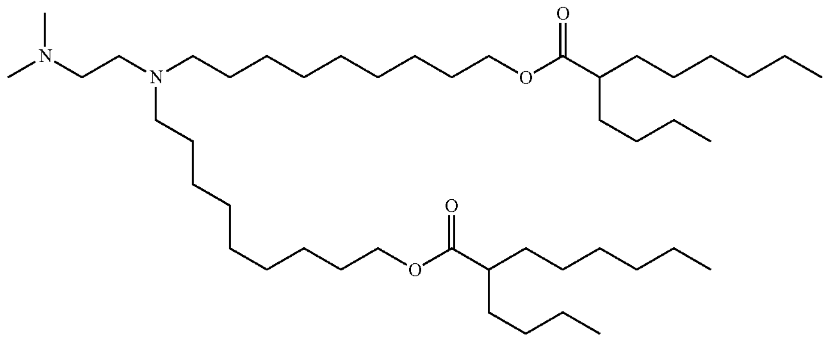 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

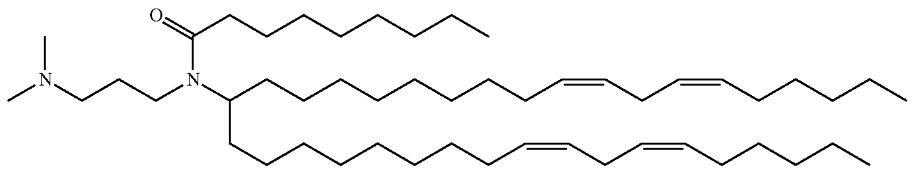 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

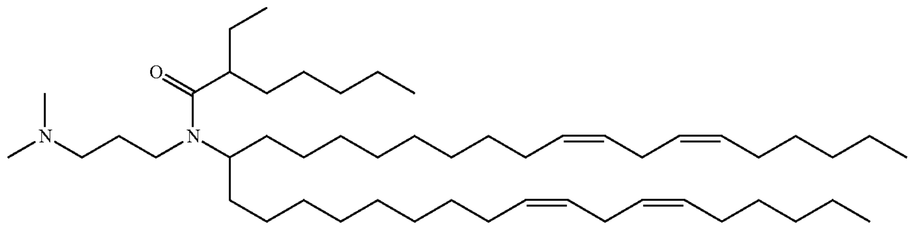 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

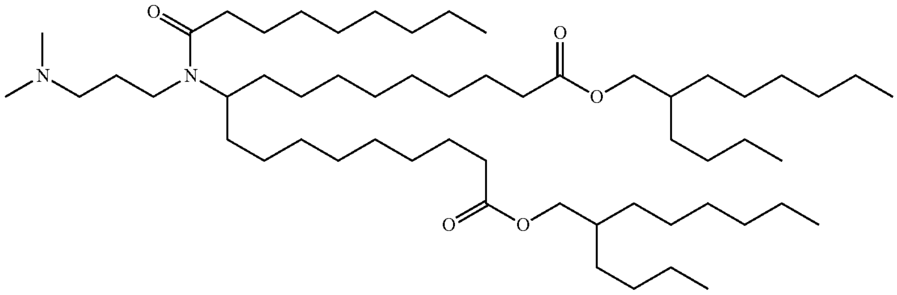 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

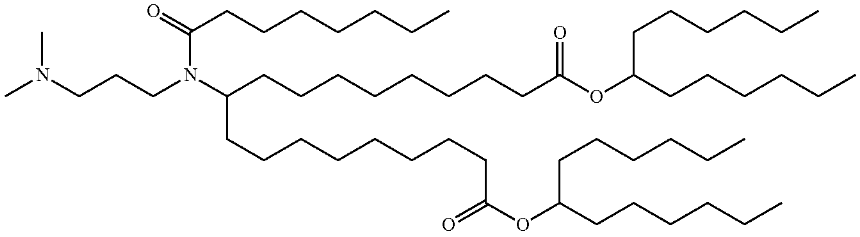 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

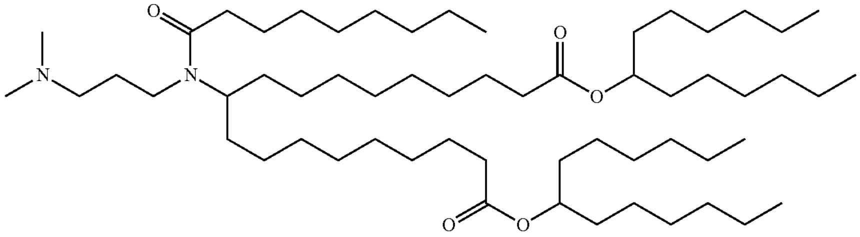 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

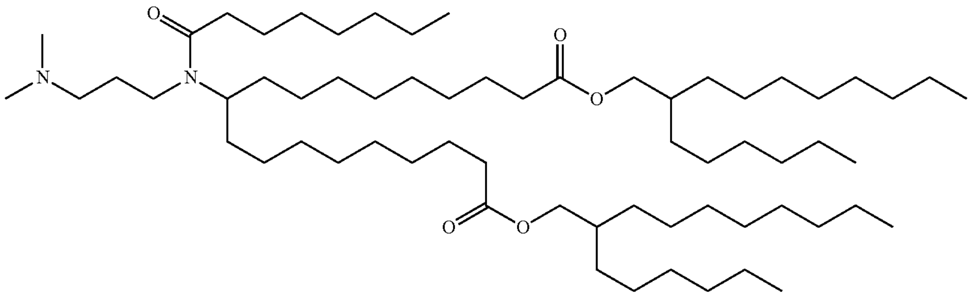 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

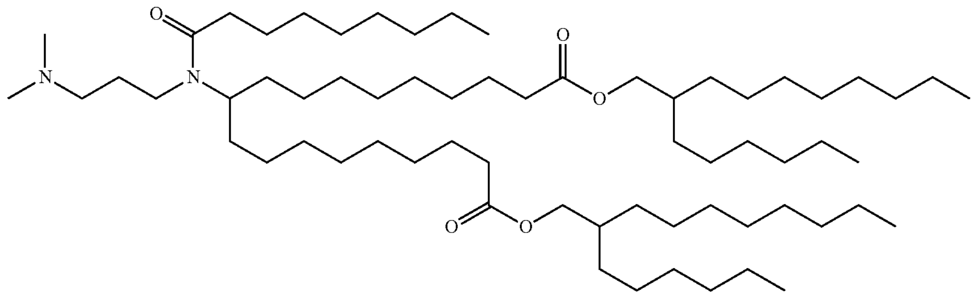 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

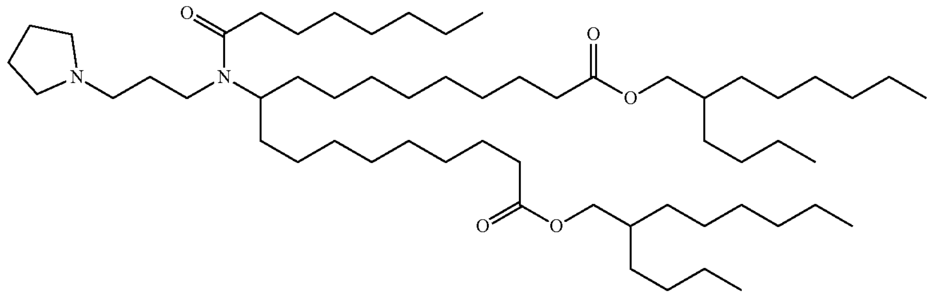 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

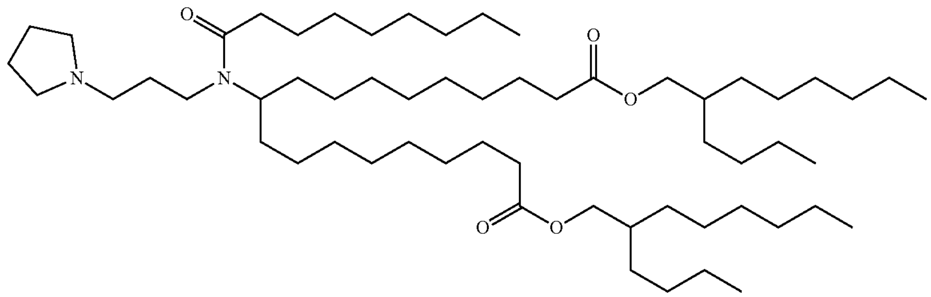 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

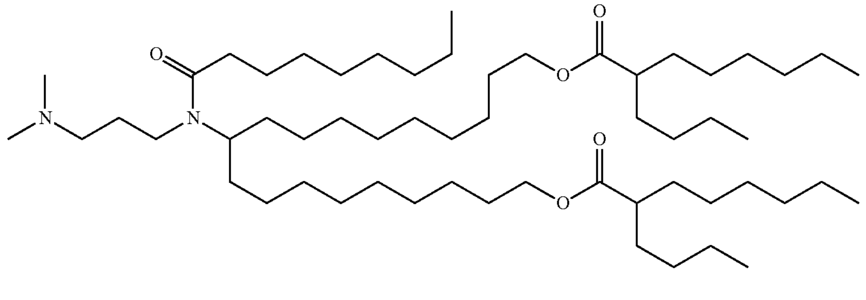 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

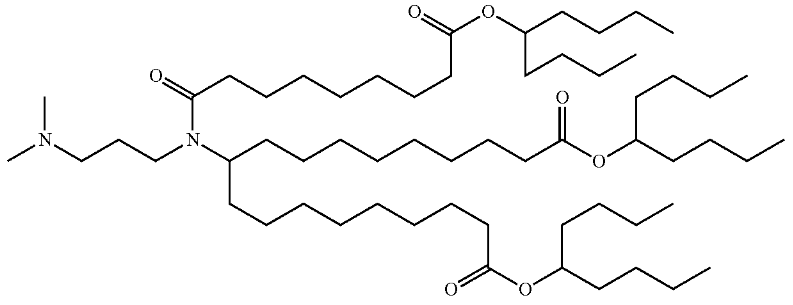 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

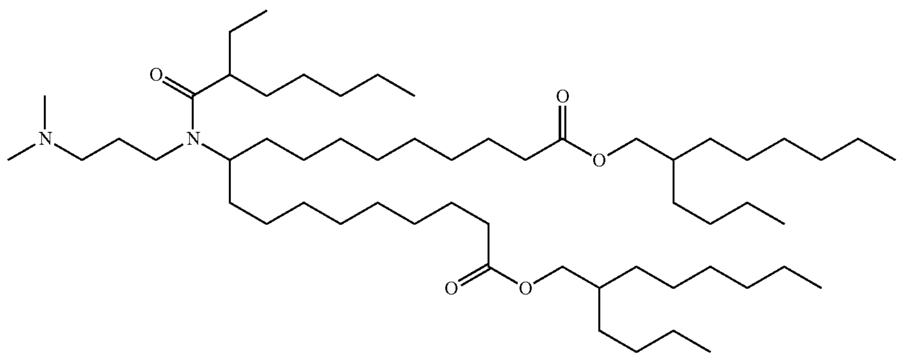 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

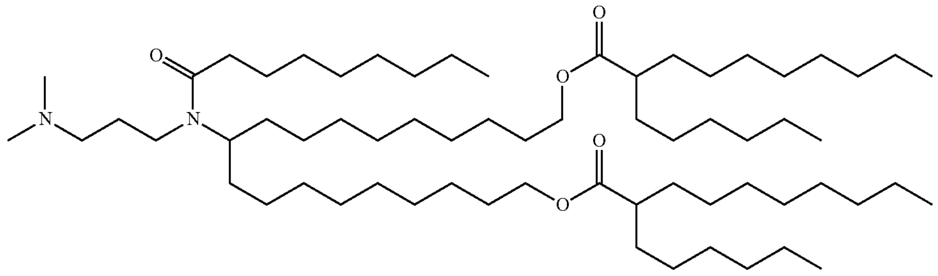 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

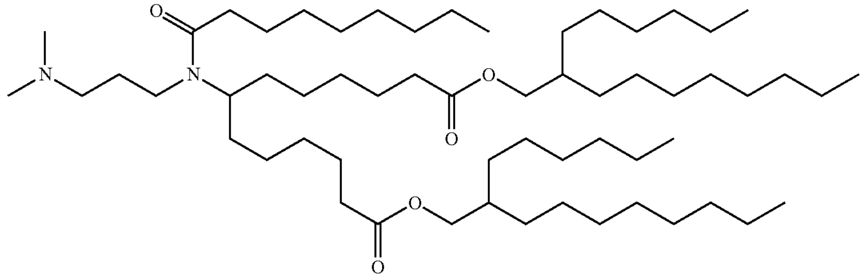 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

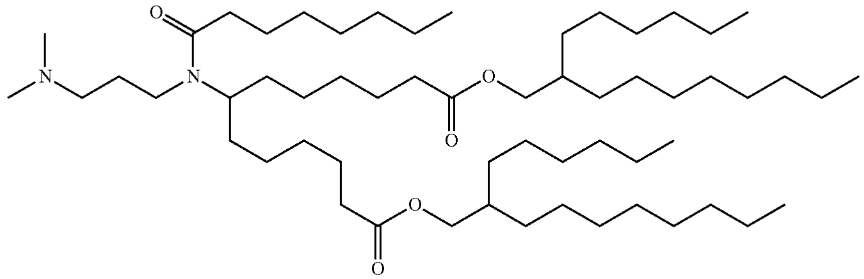

and pharmaceutically acceptable salts thereof. In some embodiments, the compositions and methods of the present invention include a cationic lipid having the compound structure:

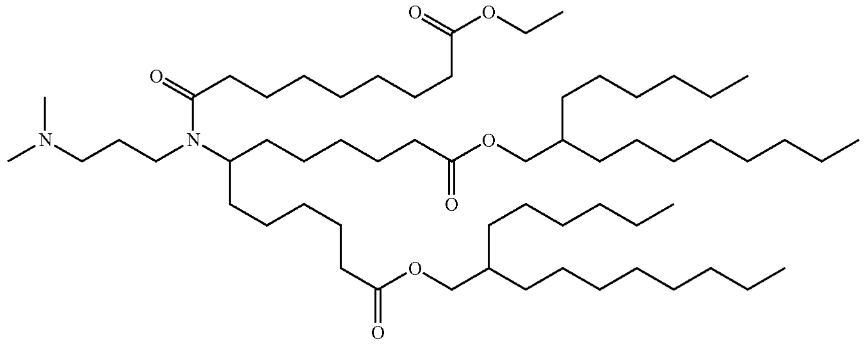 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

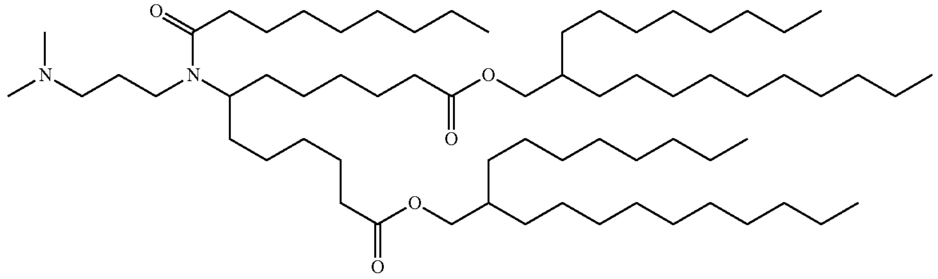 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

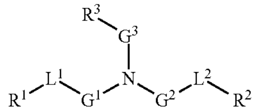

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$ C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

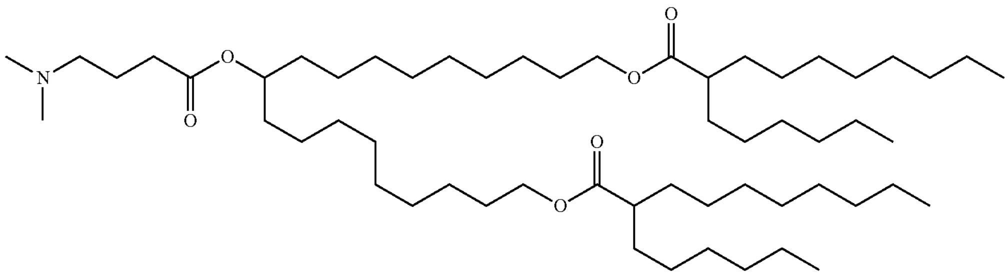 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

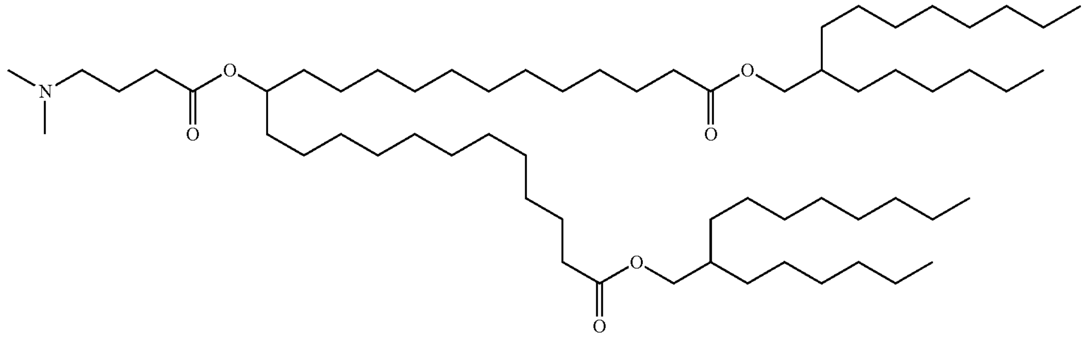 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

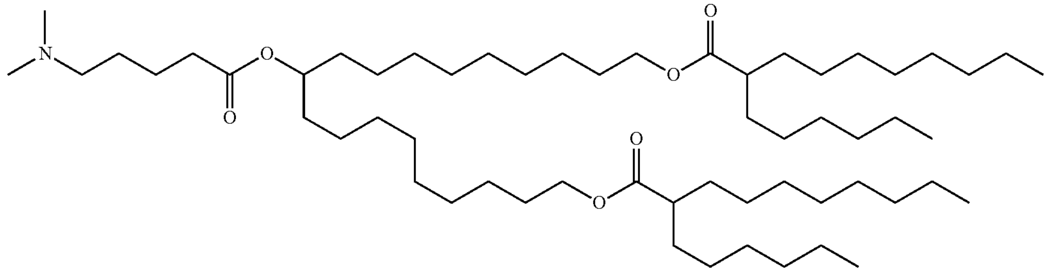 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

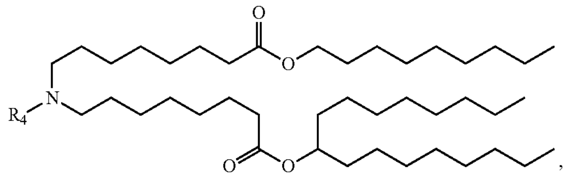

,

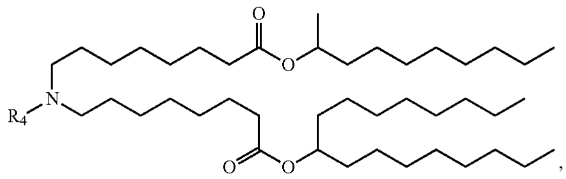

,

-continued

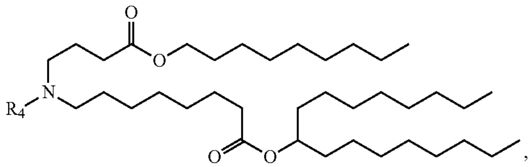

, and

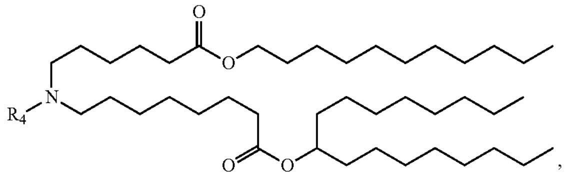

, and pharmaceutically acceptable salts thereof. For any one of these four formulas, $R_4$ is independently selected from $-(CH_2)_nQ$ and $-(CH_2)_nCHQR$; Q is selected from the group consisting of $-OR$, $-OH$, $-O(CH_2)_nN(R)_2$, $-OC(O)R$, $-CX_3$, $-CN$, $-N(R)C(O)R$, $-N(H)C(O)R$, $-N(R)S(O)_2R$, $-N(H)S(O)_2R$, $-N(R)C(O)N(R)_2$, $-N(H)C(O)N(R)_2$, $-N(H)C(O)N(H)(R)$, $-N(R)C(S)N(R)_2$, $-N(H)C(S)N(R)_2$, $-N(H)C(S)N(H)(R)$, and a heterocycle; and n is 1, 2, or 3. In certain embodiments, the compositions and methods of the present invention include a cationic lipid having a compound structure of:

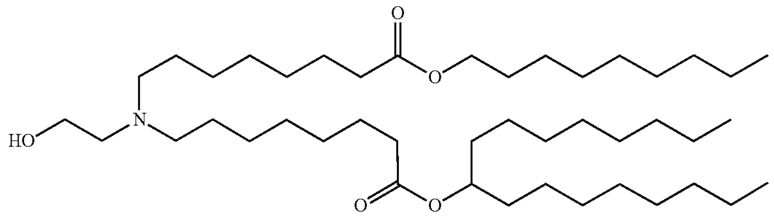 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

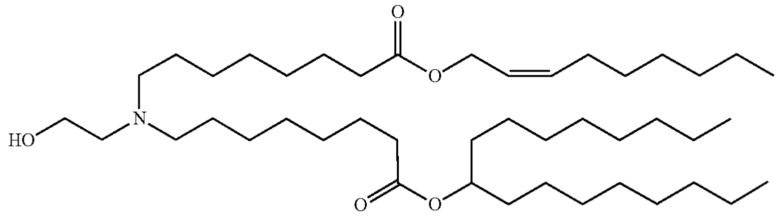 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

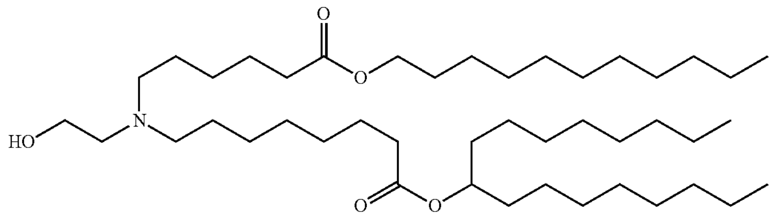 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

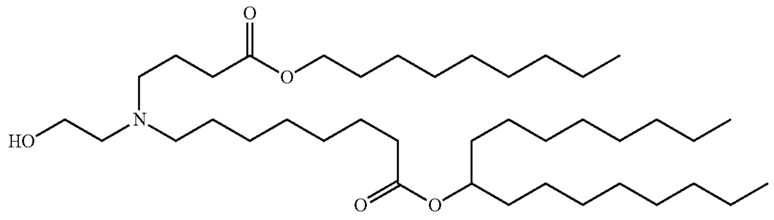 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

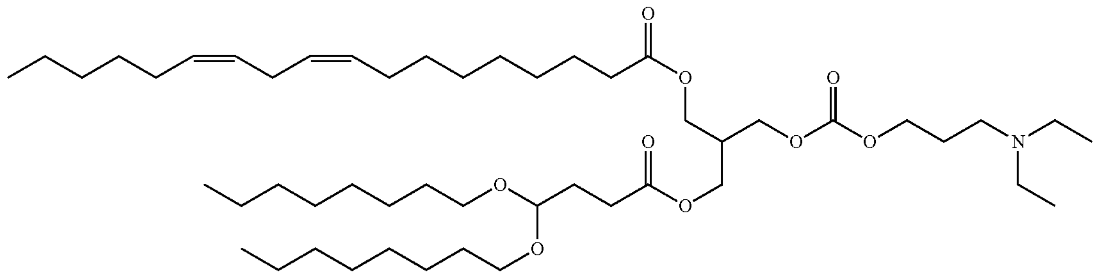

and pharmaceutically acceptable salts thereof. In certain embodiments, the compositions and methods of the present invention include a cationic lipid having a compound structure of:

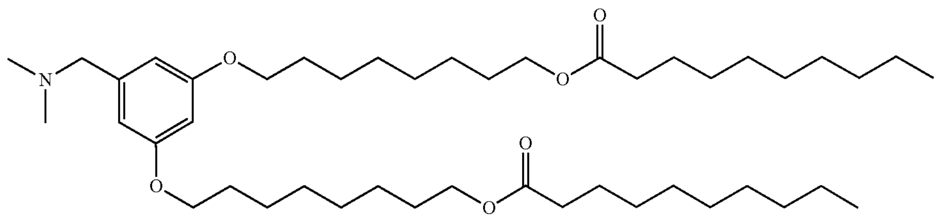 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

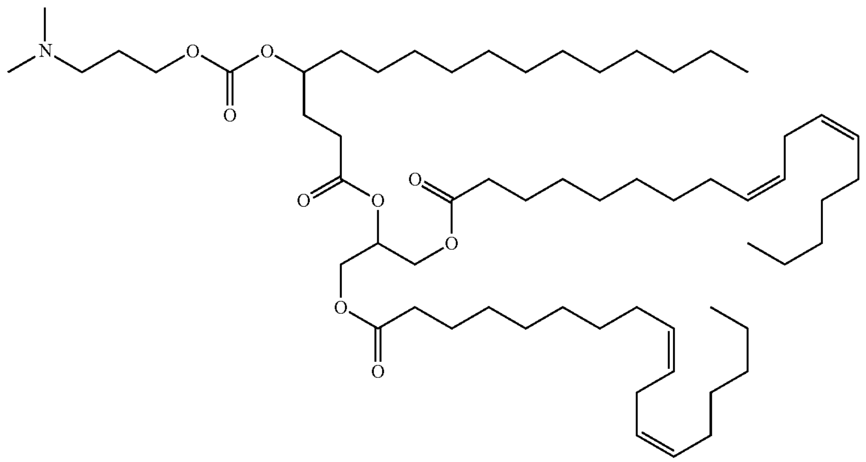 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

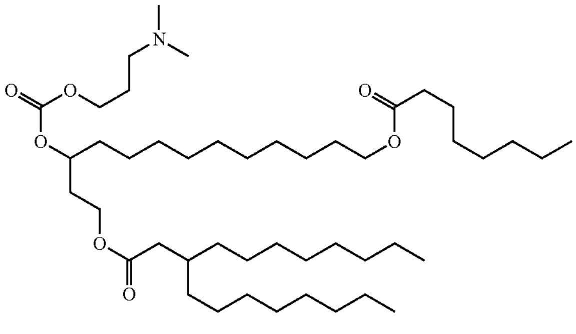 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

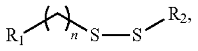

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

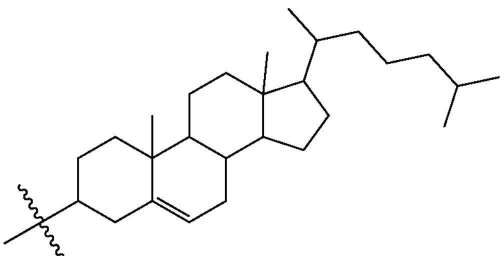

and

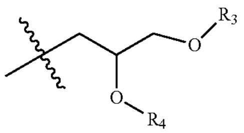

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

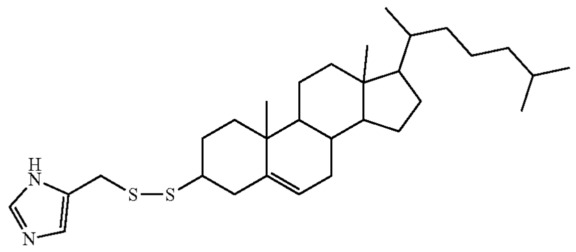

and pharmaceutically acceptable salts thereof. In certain embodiments, the compositions and methods of the present invention include a cationic lipid, "HGT4002," having a compound structure of:

(HGT4002)

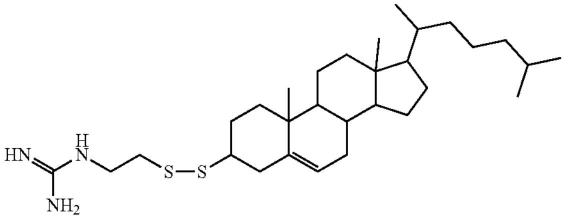

and pharmaceutically acceptable salts thereof. In certain embodiments, the compositions and methods of the present invention include a cationic lipid, "HGT4003," having a compound structure of.

(HGT4003)

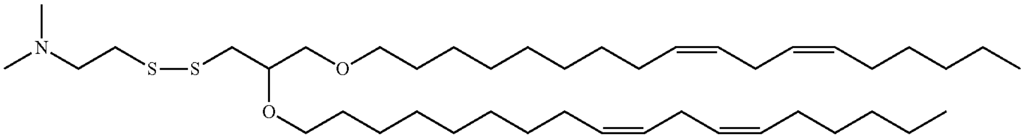

and pharmaceutically acceptable salts thereof. In certain embodiments, the compositions and methods of the present invention include a cationic lipid, "HGT4004," having a compound structure of:

(HGT4004)

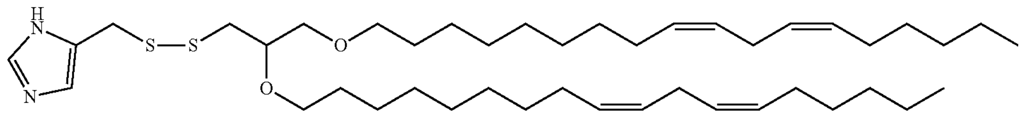

and pharmaceutically acceptable salts thereof. In certain embodiments, the compositions and methods of the present invention include a cationic lipid "HGT4005," having a compound structure of:

(HGT4005)

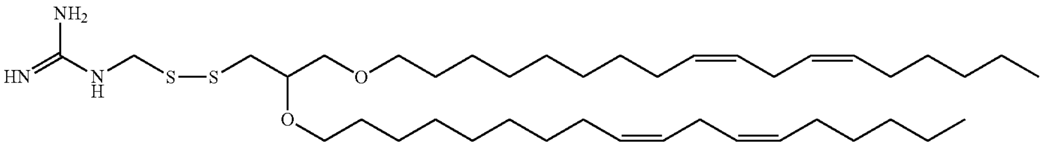

and pharmaceutically acceptable salts thereof.

Other suitable cationic lipids for use in the compositions and methods of the present invention include cleavable cationic lipids as described in International Application No. PCT/US2019/032522, and incorporated herein by reference. In certain embodiments, the compositions and methods of the present invention include a cationic lipid that is any of general formulas or any of structures (1a)-(21a) and (1b)-(21b) and (22H237) described in International Application No. PCT/US2019/032522. In certain embodiments, the compositions and methods of the present invention include a cationic lipid that has a structure according to Formula (I'), (I')

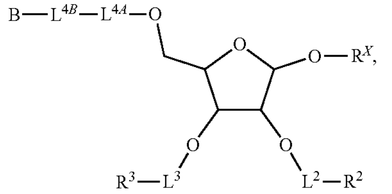

wherein:

- $R^X$ is independently —H, $-L^1-R^1$, or $-L^{5A}-L^{5B}-B'$; each of $L^1$, $L^2$, and $L^3$ is independently a covalent bond, —C(O)—, —C(O)O—, —C(O)S—, or —C(O)$NR^L$—;
- each $L^{4A}$ and $L^{5A}$ is independently —C(O)—, —C(O)O—, or —C(O)$NR^L$—;
- each $L^{4B}$ and $L^{5B}$ is independently $C_1$-$C_{20}$ alkylene; $C_2$-$C_{20}$ alkenylene; or $C_2$-$C_{20}$ alkynylene;
- each B and B' is $NR^4R^5$ or a 5- to 10-membered nitrogen-containing heteroaryl;
- each $R^1$, $R^2$, and $R^3$ is independently $C_6$-$C_{30}$ alkyl, $C_6$-$C_{30}$ alkenyl, or $C_6$-$C_{30}$ alkynyl; each $R^4$ and $R^5$ is independently hydrogen, $C_1$-$C_{10}$ alkyl; $C_2$-$C_{10}$ alkenyl; or $C_2$-$C_{10}$ alkynyl; and
- each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of International Application No. PCT/US2019/032522, having a compound structure of:

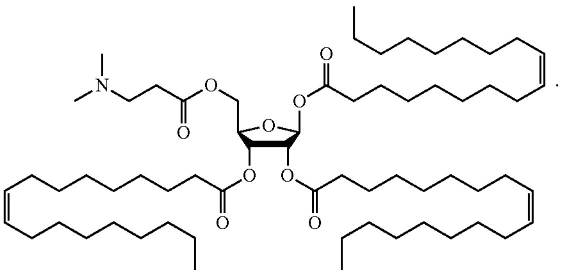

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido)ethyl]-N,N-dimethyl-1-propanaminium ("DOSPA") (Behr el al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-

(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N, N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,1 2-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50/a, about 30-45%, about 30-40%, about 35-50%, about 35-45%, or about 35-40%), measured as mol %, of the total lipid content in the composition, e.g., a lipid nanoparticle.

Non-Cationic/Helper Lipids

In some embodiments, the liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), 1,2-Dierucoyl-sn-glycero-3-phosphoethanolamine (DEPE), or a mixture thereof.

In some embodiments, a non-cationic lipid is a neutral lipid, i.e., a lipid that does not carry a net charge in the conditions under which the composition is formulated and/or administered.

In some embodiments, such non-cationic lipids may be used alone, but are preferably used in combination with other lipids, for example, cationic lipids.

In some embodiments, a non-cationic lipid may be present in a molar ratio (mol %) of about 5% to about 90/o, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 mol %, greater than about 10 mol %, greater than about 20 mol %, greater than about 30 mol %, or greater than about 40 mol %. In some embodiments, the percentage total non-cationic lipids in a liposome may be greater than about 5 mol %, greater than about 10 mol %, greater than about 20 mol %, greater than about 30 mol %, or greater than about 40 mol %. In some embodiments, the percentage of non-cationic lipid in a liposome is no more than about 5 mol %, no more than about 10 mol %, no more than about 20 mol %, no more than about 30 mol %, or no more than about 40 mol %. In some embodiments, the percentage total non-cationic lipids in a liposome may be no more than about 5 mol %, no more than about 10 mol %, no more than about 20 mol %, no more than about 30 mol %, or no more than about 40 mol %.

In some embodiments, a non-cationic lipid may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 wt %, greater than about 10 wt %, greater than about 20 wt %, greater than about 30 wt %, or greater than about 40 wt %. In some embodiments, the percentage total non-cationic lipids in a liposome may be greater than about 5 wt %, greater than about 10 wt %, greater than about 20 wt %, greater than about 30 wt %, or greater than about 40 wt %. In some embodiments, the percentage of non-cationic lipid in a liposome is no more than about 5 wt %, no more than about 10 wt %, no more than about 20 wt %, no more than about 30 wt %, or no more than about 40 wt %. In some embodiments, the percentage total non-cationic lipids in a liposome may be no more than about 5 wt %, no more than about 10 wt %, no more than about 20 wt %, no more than about 30 wt %, or no more than about 40 wt %.

Cholesterol-Based Lipids

In some embodiments, the liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or imidazole cholesterol ester (ICE), which has the following structure,

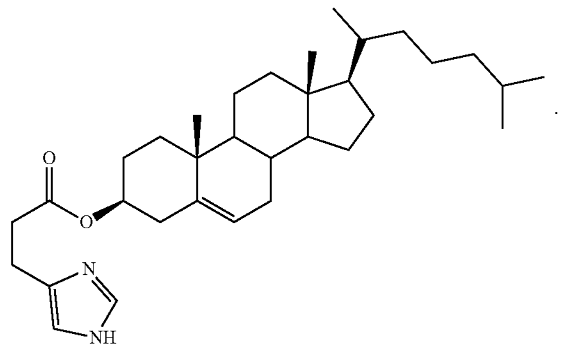

("ICE")

In embodiments, a cholesterol-based lipid is cholesterol.

In some embodiments, the cholesterol-based lipid may comprise a molar ratio (mol %) of about 1% to about 30%, or about 5% to about 20% of the total lipids present in a liposome. In some embodiments, the percentage of cholesterol-based lipid in the lipid nanoparticle may be greater than about 5 mol %, greater than about 10 mol %, greater than about 20 mol %, greater than about 30 mol %, or greater than about 40 mol %. In some embodiments, the percentage of cholesterol-based lipid in the lipid nanoparticle may be no more than about 5 mol %, no more than about 10 mol %, no more than about 20 mol %, no more than about 30 mol %, or no more than about 40 mol %.

In some embodiments, a cholesterol-based lipid may be present in a weight ratio (wt %) of about 1% to about 30%, or about 5% to about 20% of the total lipids present in a liposome. In some embodiments, the percentage of cholesterol-based lipid in the lipid nanoparticle may be greater than about 5 wt %, greater than about 10 wt %, greater than about 20 wt %, greater than about 30 wt %, or greater than about 40 wt %. In some embodiments, the percentage of cholesterol-based lipid in the lipid nanoparticle may be no more than about 5 wt %, no more than about 10 wt %, no more than about 20 wt %, no more than about 30 wt %, or no more than about 40 wt %.

PEG-Modified Lipids

In some embodiments, the liposome comprises one or more PEGylated lipids.

For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle).

Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., $C_{14}$ or $C_{18}$).

The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle. In some embodiments, one or more PEG-modified lipids constitute about 4% of the total lipids by molar ratio. In some embodiments, one or more PEG-modified lipids constitute about 5% of the total lipids by molar ratio. In some embodiments, one or more PEG-modified lipids constitute about 6% of the total lipids by molar ratio.

Amphiphilic Block Copolymers

In some embodiments, a suitable composition contains amphiphilic block copolymers (e.g., poloxamers).

Various amphiphilic block copolymers may be used to practice the present invention. In some embodiments, an amphiphilic block copolymer is also referred to as a surfactant or a non-ionic surfactant.

In some embodiments, an amphiphilic polymer suitable for the invention is selected from poloxamers (Pluronic®), poloxamines (Tetronic®), polyoxyethylene glycol sorbitan alkyl esters (polysorbates) and polyvinyl pyrrolidones (PVPs).

Poloxamers

In some embodiments, a suitable amphiphilic polymer is a poloxamer. For example, a suitable poloxamer is of the following structure:

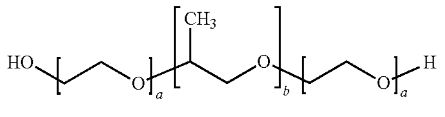

wherein a is an integer between 10 and 150 and b is an integer between 20 and 60. For example, a is about 12 and b is about 20, or a is about 80 and b is about 27, or a is about 64 and b is about 37, or a is about 141 and b is about 44, or a is about 101 and b is about 56.

In some embodiments, a poloxamer suitable for the invention has ethylene oxide units from about 10 to about 150. In some embodiments, a poloxamer has ethylene oxide units from about 10 to about 100.

In some embodiments, a suitable poloxamer is poloxamer 84. In some embodiments, a suitable poloxamer is poloxamer 101. In some embodiments, a suitable poloxamer is poloxamer 105. In some embodiments, a suitable poloxamer is poloxamer 108. In some embodiments, a suitable poloxamer is poloxamer 122. In some embodiments, t a suitable poloxamer is poloxamer 123. In some embodiments, a suitable poloxamer is poloxamer 124. In some embodiments, a suitable poloxamer is poloxamer 181. In some embodiments, a suitable poloxamer is poloxamer 182. In some embodiments, a suitable poloxamer is poloxamer 183. In some embodiments, a suitable poloxamer is poloxamer 184. In some embodiments, a suitable poloxamer is poloxamer 185. In some embodiments, a suitable poloxamer is poloxamer 188. In some embodiments, a suitable poloxamer is poloxamer 212. In some embodiments, a suitable poloxamer is poloxamer 215. In some embodiments, a suitable poloxamer is poloxamer 217. In some embodiments, a suitable poloxamer is poloxamer 231. In some embodiments, a suitable poloxamer is poloxamer 234. In some embodiments, a suitable poloxamer is poloxamer 235. In some embodiments, a suitable poloxamer is poloxamer 237. In some embodiments, a suitable poloxamer is poloxamer 238. In some embodiments, a suitable poloxamer is poloxamer 282. In some embodiments, a suitable poloxamer is poloxamer 284. In some embodiments, a suitable poloxamer is poloxamer 288. In some embodiments, a suitable poloxamer is poloxamer 304. In some embodiments, a suitable poloxamer is poloxamer 331. In some embodiments, a suitable poloxamer is poloxamer 333. In some embodiments, a suitable poloxamer is poloxamer 334. In some embodiments, a suitable poloxamer is poloxamer 335. In some embodiments, a suitable poloxamer is poloxamer 338. In some embodiments, a suitable poloxamer is poloxamer 401. In some embodiments, a suitable poloxamer is poloxamer 402. In some embodiments, a suitable poloxamer is poloxamer 403. In some embodiments, a suitable poloxamer is poloxamer 407. In some embodiments, a suitable poloxamer is a combination thereof.

In some embodiments, a suitable poloxamer has an average molecular weight of about 4,000 g/mol to about 20,000 g/mol. In some embodiments, a suitable poloxamer has an average molecular weight of about 1,000 g/mol to about 50,000 g/mol. In some embodiments, a suitable poloxamer has an average molecular weight of about 1,000 g/mol. In some embodiments, a suitable poloxamer has an average molecular weight of about 2,000 g/mol. In some embodiments, a suitable poloxamer has an average molecular weight of about 3,000 g/mol. In some embodiments, a suitable poloxamer has an average molecular weight of about 4,000 g/mol. In some embodiments, a suitable poloxamer has an average molecular weight of about 5,000 g/mol. In some embodiments, a suitable poloxamer has an average molecular weight of about 6,000 g/mol. In some embodiments, a suitable poloxamer has an average molecular weight of about 7,000 g/mol. In some embodiments, a suitable poloxamer has an average molecular weight of about 8,000 g/mol. In some embodiments, a suitable poloxamer has an average molecular weight of about 9,000 g/mol. In some embodiments, a suitable poloxamer has an average molecular weight of about 10,000 g/mol. In some embodiments, a suitable poloxamer has an average molecular weight of about 20,000 g/mol. In some embodiments, a suitable poloxamer has an average molecular weight of about 25,000 g/mol. In some embodiments, a suitable poloxamer has an average molecular weight of about 30,000 g/mol. In some embodiments, a suitable poloxamer has an average molecular weight of about 40,000 g/mol. In some embodiments, a suitable poloxamer has an average molecular weight of about 50,000 g/mol.

Other Amphiphilic Polymers

In some embodiments, an amphiphilic polymer is a poloxamine, e.g., tetronic 304 or tetronic 904.

In some embodiments, an amphiphilic polymer is a polyvinylpyrrolidone (PVP), such as PVP with molecular weight of 3 kDa, 10 kDa, or 29 kDa.

In some embodiments, an amphiphilic polymer is a polyethylene glycol ether (Brij), polysorbate, sorbitan, and derivatives thereof. In some embodiments, an amphiphilic polymer is a polysorbate, such as PS 20.

In some embodiments, an amphiphilic polymer is polyethylene glycol ether (Brij), poloxamer, polysorbate, sorbitan, or derivatives thereof.

In some embodiments, an amphiphilic polymer is a polyethylene glycol ether. In some embodiments, a suitable polyethylene glycol ether is a compound of Formula (S-1):

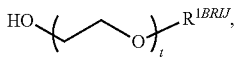

(S-1)

or a salt or isomer thereof, wherein:

t is an integer between 1 and 100, $R^{1BRIJ}$ independently is $C_{10-40}$ alkyl, $C_{10-40}$ alkenyl, or $C_{10-40}$ alkynyl; and optionally one or more methylene groups of $R^{5PEG}$ are independently replaced with $C_{3-10}$ carbocyclylene, 4 to 10 membered heterocyclylene, $C_{6-10}$ arylene, 4 to 10 membered heteroarylene, —N($R^N$)—, —O—, —S—, —C(O)—, —C(O)N($R^N$)—, —$NR^N$C(O)—, —NR C(O)N(R)—, —C(O)O— —OC(O)—, —OC(O)O— —OC(O)N($R^N$)—, —$NR^N$C(O)O— —C(O)S— —SC(O)—, —C(=$NR^N$)—, —C(=NR)N(R)—, —$NR^N$C(=$NR^N$)— —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O— —OS(O)O— —$OS(O)_2$— —$S(O)_2O$— —$OS(O)_2O$— —N($R^N$)S(O)—, —S(O)N($R^N$)— —N($R^N$)S(O)N($R^N$)— —OS(O)N($R^N$)— —N($R^N$)S(O)O— —$S(O)_2$— —N($R^N$)$S(O)_2$— —$S(O)_2$N($R^N$)—, —N($R^N$)$S(O)_2$N($R^N$)— —$OS(O)_2$N($R^N$)— or —N($R^N$)$S(O)_2O$—; and each instance of $R^N$ is independently hydrogen, $C_{1-6}$ alkyl, or a nitrogen protecting group.

In some embodiment, $R^{IBRU}$ is C is alkyl. For example, the polyethylene glycol ether is a compound of Formula (S-1a):

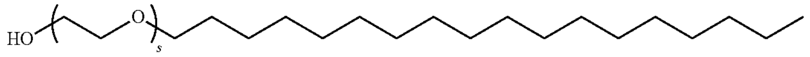

(S-1a)

or a salt or isomer thereof, wherein s is an integer between 1 and 100.

In some embodiments, $R^{IBRU}$ is C is alkenyl. For example, a suitable polyethylene glycol ether is a compound of Formula (S-1b):

(S-1b)

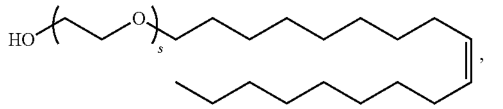

or a salt or isomer thereof, wherein s is an integer between 1 and 100.

Typically, an amphiphilic polymer (e.g., a poloxamer) is present in a formulation at an amount lower than its critical micelle concentration (CMC). In some embodiments, an amphiphilic polymer (e.g., a poloxamer) is present in the mixture at an amount about 1%, about 2%, about 3%, about 4%, about 5%, about 6%, about 7%, about 8%, about 9%, about 10%, about 15%, about 20%, about 25%, about 30%, about 350, about 40%, about 450, or about 50% lower than its CMC. In some embodiments, an amphiphilic polymer (e.g., a poloxamer) is present in the mixture at an amount about 0.9%, 0.8%, 0.7%, 0.6%, 0.5%, 0.4%, 0.3%, 0.2%, 0.1% lower than its CMC. In some embodiments, an amphiphilic polymer (e.g., a poloxamer) is present in the mixture at an amount about 55%, 60%, 65%, 70%, 75%, 80%, 90°/c, or 95% lower than its CMC.

In some embodiments, less than about 0.1%, 0.09%, 0.08%, 0.07%, 0.06%, 0.05%, 0.04%, 0.03%, 0.02%, or 0.01% of the original amount of the amphiphilic polymer (e.g., the poloxamer) present in the formulation remains upon removal. In some embodiments, a residual amount of the amphiphilic polymer (e.g., the poloxamer) remains in a formulation upon removal. As used herein, a residual amount means a remaining amount after substantially all of the substance (an amphiphilic polymer described herein such as a poloxamer) in a composition is removed. A residual amount may be detectable using a known technique qualitatively or quantitatively. A residual amount may not be detectable using a known technique.

In some embodiments, a suitable composition comprises less than 5% amphiphilic block copolymers (e.g., poloxamers). In some embodiments, a suitable composition comprises less than 3% amphiphilic block copolymers (e.g., poloxamers). In some embodiments, a suitable composition comprises less than 2.5% amphiphilic block copolymers (e.g., poloxamers). In some embodiments, a suitable composition comprises less than 2% amphiphilic block copolymers (e.g., poloxamers). In some embodiments, a suitable composition comprises less than 1.5% amphiphilic block copolymers (e.g., poloxamers). In some embodiments, a suitable composition comprises less than 1% amphiphilic block copolymers (e.g., poloxamers). In some embodiments, a suitable composition comprises less than 0.5% (e.g., less than 0.4%, 0.3%, 0.2%, 0.1%) amphiphilic block copolymers (e.g., poloxamers). In some embodiments, a suitable composition comprises less than 0.09%, 0.08%, 0.07%, 0.06%, 0.05%, 0.04%, 0.03%, 0.02%, or 0.01% amphiphilic block copolymers (e.g., poloxamers). In some embodiments, a suitable composition comprises less than 0.01% amphiphilic block copolymers (e.g., poloxamers). In some embodiments, a suitable composition contains a residual amount of amphiphilic polymers (e.g., poloxamers). As used herein, a residual amount means a remaining amount after substantially all of the substance (an amphiphilic polymer described herein such as a poloxamer) in a composition is removed. A residual amount may be detectable using a known technique qualitatively or quantitatively. A residual amount may not be detectable using a known technique.

Polymers

In some embodiments, a suitable composition is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

According to various embodiments, the selection of cationic lipids, non-cationic lipids, PEG-modified lipids, cholesterol-based lipids, and/or amphiphilic block copolymers which comprise the lipid nanoparticle, as well as the relative molar ratio of such components (lipids) to each other, is based upon the characteristics of the selected lipid(s), the nature of the intended target cells, the characteristics of the nucleic acid to be delivered. Additional considerations include, for example, the saturation of the alkyl chain, as well as the size, charge, pH, Pak, fusogenicity and tolerability of the selected lipid(s). Thus the molar ratios may be adjusted accordingly.

Ratio of Distinct Lipid Components

A suitable liposome for the present invention may include one or more of any of the cationic lipids, non-cationic lipids, cholesterol lipids, PEG-modified lipids, amphiphilic block copolymers and/or polymers described herein at various ratios. In some embodiments, a lipid nanoparticle comprises five and no more than five distinct components of nanoparticle. In some embodiments, a lipid nanoparticle comprises four and no more than four distinct components of nanoparticle. In some embodiments, a lipid nanoparticle comprises three and no more than three distinct components of nanoparticle. As non-limiting examples, a suitable liposome formulation may include a combination selected from cKK-E12 (also known as ML2), DOPE, cholesterol and DMG-PEG2K; $C_{12}$-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

In embodiments where a lipid nanoparticle comprises three and no more than three distinct components of lipids, the ratio of total lipid content (i.e., the ratio of lipid component (1):lipid component (2):lipid component (3)) can be represented as x:y:z, wherein $$(y+z)=100-x.$$

In some embodiments, each of "x," "y," and "z" represents molar percentages of the three distinct components of lipids, and the ratio is a molar ratio.

In some embodiments, each of "x," "y," and "z" represents weight percentages of the three distinct components of lipids, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z" is a PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%, at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "z," representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the molar percentage of lipid component (3) (e.g., a PEG lipid) is about 1%, 2%, 3%, 4%, 5%, 6%, 7%, 8%, 9%, 10%. In embodiments, variable "z," representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the weight percentage of lipid component (3) (e.g., a PEG lipid) is about 1%, 2%, 3%, 4%, 5%, 6%, 7%, 8%, 9%, 10%. In embodiments, variable "z," representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

Therapeutic Use of Compositions

The present invention provides, among other things, therapeutic mRNA-LNP composition useful for treating patients. The mRNA encapsulated in lipid nanoparticles can be delivered to cells or subjects in vivo and encode a protein or polypeptide. Accordingly, in certain embodiments the present invention provides a method for producing a therapeutic composition comprising mRNA that encode a peptide or polypeptide for use in the delivery to or treatment of the lung of a subject or a lung cell. In certain embodiments the present invention provides a method for producing a therapeutic composition having mRNA that encode for cystic fibrosis transmembrane conductance regulator (CFTR) protein. In certain embodiments the present invention provides a method for producing a therapeutic composition having mRNA that encode for ATP-binding cassette sub-family A member 3 protein. In certain embodiments the present invention provides a method for producing a therapeutic composition having mRNA that encode for dynein axonemal intermediate chain 1 protein. In certain embodiments the present invention provides a method for producing a therapeutic composition having mRNA that encode for dynein axonemal heavy chain 5 (DNAH5) protein. In certain embodiments the present invention provides a method for producing a therapeutic composition having mRNA that encode for alpha-1-antitrypsin protein. In certain embodiments the present invention provides a method for producing a therapeutic composition having mRNA that encode for forkhead box P3 (FOXP3) protein. In certain embodiments the present invention provides a method for producing a therapeutic composition having mRNA that encode one or more surfactant protein, e.g., one or more of surfactant A protein, surfactant B protein, surfactant C protein, and surfactant D protein.

In certain embodiments the present invention provides a method for producing a therapeutic composition having mRNA that encode a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched mRNA provide a therapeutic benefit.

In certain embodiments the present invention provides a method for producing a therapeutic composition having mRNA that encode for a protein associated with a urea cycle disorder. In certain embodiments the present invention provides a method for producing a therapeutic composition having mRNA that encode for ornithine transcarbamylase (OTC) protein. In certain embodiments the present invention provides a method for producing a therapeutic composition having mRNA that encode for arginosuccinate synthetase 1 protein. In certain embodiments the present invention provides a method for producing a therapeutic composition having mRNA that encode for carbamoyl phosphate synthetase I protein. In certain embodiments the present invention provides a method for producing a therapeutic composition having mRNA that encode for arginosuccinate lyase protein. In certain embodiments the present invention provides a method for producing a therapeutic composition having mRNA that encode for arginase protein.

In certain embodiments the present invention provides a method for producing a therapeutic composition having mRNA that encode for a protein associated with a lysosomal storage disorder. In certain embodiments the present invention provides a method for producing a therapeutic composition having mRNA that encode for alpha galactosidase protein. In certain embodiments the present invention provides a method for producing a therapeutic composition having mRNA that encode for glucocerebrosidase protein. In certain embodiments the present invention provides a method for producing a therapeutic composition having mRNA that encode for iduronate-2-sulfatase protein. In certain embodiments the present invention provides a method for producing a therapeutic composition having mRNA molecules that encode for iduronidase protein. In certain embodiments the present invention provides a method for producing a therapeutic composition having mRNA that encode for N-acetyl-alpha-D-glucosaminidase protein. In certain embodiments the present invention provides a method for producing a therapeutic composition having mRNA that encode for heparan N-sulfatase protein. In certain embodiments the present invention provides a method for producing a therapeutic composition having mRNA that encode for galactosamine-6 sulfatase protein. In certain embodiments the present invention provides a method for producing a therapeutic composition having mRNA that encode for beta-galactosidase protein. In certain embodiments the present invention provides a method for producing a therapeutic composition having mRNA that encode for lysosomal lipase protein. In certain embodiments the present invention provides a method for producing a therapeutic composition having mRNA that encode for arylsulfatase B (N-acetylgalactosamine-4-sulfatase) protein. In certain embodiments the present invention provides a method for producing a therapeutic composition having mRNA molecules that encode for transcription factor EB (TFEB).

In certain embodiments the present invention provides a method for producing a therapeutic composition having mRNA that encode for a protein associated with a glycogen storage disorder. In certain embodiments the present invention provides a method for producing a therapeutic composition having mRNA that encode for acid alpha-glucosidase protein. In certain embodiments the present invention provides a method for producing a therapeutic composition having mRNA that encode for glucose-6-phosphatase (G6PC) protein. In certain embodiments the present invention provides a method for producing a therapeutic composition having mRNA that encode for liver glycogen phosphorylase protein. In certain embodiments the present invention provides a method for producing a therapeutic composition having mRNA that encode for muscle phosphoglycerate mutase protein. In certain embodiments the present invention provides a method for producing a therapeutic composition having mRNA that encode for glycogen debranching enzyme.

In certain embodiments the present invention provides a method for producing a therapeutic composition having mRNA that encode for a protein associated with amino acid metabolism. In certain embodiments the present invention provides a method for producing a therapeutic composition having mRNA that encode for phenylalanine hydroxylase enzyme. In certain embodiments the present invention provides a method for producing a therapeutic composition having mRNA that encode for glutaryl-CoA dehydrogenase enzyme. In certain embodiments the present invention provides a method for producing a therapeutic composition having mRNA that encode for propionyl-CoA caboxylase enzyme. In certain embodiments the present invention provides a method for producing a therapeutic composition having mRNA that encode for oxalase alanine-glyoxylate aminotransferase enzyme.

In certain embodiments the present invention provides a method for producing a therapeutic composition having mRNA that encode for a protein associated with a lipid metabolism or fibrotic disorder. In certain embodiments the present invention provides a method for producing a therapeutic composition having mRNA that encode for a mTOR inhibitor. In certain embodiments the present invention provides a method for producing a therapeutic composition having mRNA that encode for ATPase phospholipid transporting 8B1 (ATP8B1) protein. In certain embodiments the present invention provides a method for producing a therapeutic composition having mRNA that encode for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition having mRNA that encode for PPAR-gamma protein or an active variant.

In certain embodiments the present invention provides a method for producing a therapeutic composition having mRNA that encode for a protein associated with methylmalonic acidemia. For example, in certain embodiments the present invention provides a method for producing a therapeutic composition having mRNA that encode for methylmalonyl CoA mutase protein. In certain embodiments the present invention provides a method for producing a therapeutic composition having mRNA that encode for methylmalonyl CoA epimerase protein.

In certain embodiments the present invention provides a method for producing a therapeutic composition having full-length mRNA for which delivery to or treatment of the liver can provide therapeutic benefit. In certain embodiments the present invention provides a method for producing a therapeutic composition having mRNA that encode for ATP7B protein, also known as Wilson disease protein. In certain embodiments the present invention provides a method for producing a therapeutic composition having mRNA that encode for porphobilinogen deaminase enzyme. In certain embodiments the present invention provides a method for producing a therapeutic composition having mRNA that encode for one or clotting enzymes, such as Factor VIII, Factor IX, Factor VII, and Factor X. In certain embodiments the present invention provides a method for producing a therapeutic composition having mRNA that encode for human hemochromatosis (HFE) protein.

In certain embodiments the present invention provides a method for producing a therapeutic composition having mRNA that encode a peptide or polypeptide for use in the delivery to or treatment of the cardiovasculature of a subject or a cardiovascular cell. In certain embodiments the present invention provides a method for producing a therapeutic composition having mRNA that encode for vascular endothelial growth factor A protein. In certain embodiments the present invention provides a method for producing a therapeutic composition having mRNA that encode for relaxin protein. In certain embodiments the present invention provides a method for producing a therapeutic composition having mRNA that encode for bone morphogenetic protein-9 protein. In certain embodiments the present invention provides a method for producing a therapeutic composition having mRNA that encode for bone morphogenetic protein-2 receptor protein.

In certain embodiments the present invention provides a method for producing a therapeutic composition having mRNA that encode a peptide or polypeptide for use in the delivery to or treatment of the muscle of a subject or a muscle cell. In certain embodiments the present invention provides a method for producing a therapeutic composition having mRNA that encode for dystrophin protein. In certain embodiments the present invention provides a method for producing a therapeutic composition having mRNA that encode for frataxin protein. In certain embodiments the present invention provides a method for producing a therapeutic composition having mRNA that encode a peptide or polypeptide for use in the delivery to or treatment of the cardiac muscle of a subject or a cardiac muscle cell. In certain embodiments the present invention provides a method for producing a therapeutic composition having mRNA that encode for a protein that modulates one or both of a potassium channel and a sodium channel in muscle tissue or in a muscle cell. In certain embodiments the present invention provides a method for producing a therapeutic composition having mRNA that encode for a protein that modulates a Kv7.1 channel in muscle tissue or in a muscle cell. In certain embodiments the present invention provides a method for producing a therapeutic composition having mRNA that encode for a protein that modulates a Nav1.5 channel in muscle tissue or in a muscle cell.

In certain embodiments the present invention provides a method for producing a therapeutic composition having RNA that encode a peptide or polypeptide for use in the delivery to or treatment of the nervous system of a subject or a nervous system cell. For example, in certain embodiments the present invention provides a method for producing a therapeutic composition having mRNA that encode for survival motor neuron 1 protein. For example, in certain embodiments the present invention provides a method for producing a therapeutic composition having mRNA that encode for survival motor neuron 2 protein. In certain embodiments the present invention provides a method for producing a therapeutic composition having mRNA that encode for frataxin protein. In certain embodiments the present invention provides a method for producing a therapeutic composition having mRNA that encode for ATP binding cassette subfamily D member 1 (ABCD1) protein. In certain embodiments the present invention provides a method for producing a therapeutic composition having mRNA that encode for CLN3 protein.

In certain embodiments the present invention provides a method for producing a therapeutic composition having mRNA that encode a peptide or polypeptide for use in the delivery to or treatment of the blood or bone marrow of a subject or a blood or bone marrow cell. In certain embodiments the present invention provides a method for producing a therapeutic composition having mRNA that encode for beta globin protein. In certain embodiments the present invention provides a method for producing a therapeutic composition having mRNA that encode for Bruton's tyrosine kinase protein. In certain embodiments the present invention provides a method for producing a therapeutic composition having mRNA that encode for one or clotting enzymes, such as Factor VIII, Factor IX, Factor VII, and Factor X.

In certain embodiments the present invention provides a method for producing a therapeutic composition having mRNA that encode a peptide or polypeptide for use in the delivery to or treatment of the kidney of a subject or a kidney cell. In certain embodiments the present invention provides a method for producing a therapeutic composition having mRNA that encode for collagen type IV alpha 5 chain (COL4A5) protein.

In certain embodiments the present invention provides a method for producing a therapeutic composition having mRNA that encode a peptide or polypeptide for use in the delivery to or treatment of the eye of a subject or an eye cell. In certain embodiments the present invention provides a method for producing a therapeutic composition having mRNA that encode for ATP-binding cassette sub-family A member 4 (ABCA4) protein. In certain embodiments the present invention provides a method for producing a therapeutic composition having mRNA that encode for retinoschisin protein. In certain embodiments the present invention provides a method for producing a therapeutic composition having mRNA that encode for retinal pigment epithelium-specific 65 kDa (RPE65) protein. In certain embodiments the present invention provides a method for producing a therapeutic composition having mRNA that encode for centrosomal protein of 290 kDa (CEP290).

In certain embodiments the present invention provides a method for producing a therapeutic composition having mRNA that encode a peptide or polypeptide for use in the delivery of or treatment with a vaccine for a subject or a cell of a subject. For example, in certain embodiments the present invention provides a method for producing a therapeutic composition having mRNA that encode for an antigen from an infectious agent, such as a virus. In certain embodiments the present invention provides a method for producing a therapeutic composition having mRNA that encode for an antigen from coronavirus. In certain embodiments the present invention provides a method for producing a therapeutic composition having mRNA that encode for an antigen from COVID virus. In certain embodiments the present invention provides a method for producing a therapeutic composition having mRNA that encode for an antigen from influenza virus. In certain embodiments the present invention provides a method for producing a therapeutic composition having mRNA that encode for an antigen from respiratory syncytial virus. In certain embodiments the present invention provides a method for producing a therapeutic composition having mRNA that encode for an antigen from rabies virus. In certain embodiments the present invention provides a method for producing a therapeutic composition having mRNA that encode for an antigen from cytomegalovirus. In certain embodiments the present invention provides a method for producing a therapeutic composition having mRNA that encode for an antigen from rotavirus. In certain embodiments the present invention provides a method for producing a therapeutic composition having mRNA that encode for an antigen from a hepatitis virus, such as hepatitis A virus, hepatitis B virus, or hepatitis C virus. In certain embodiments the present invention provides a method for producing a therapeutic composition having mRNA that encode for an antigen from human papillomavirus. In certain embodiments the present invention provides a method for producing a therapeutic composition having mRNA that encode for an antigen from a herpes simplex virus, such as herpes simplex virus 1 or herpes simplex virus 2. In certain embodiments the present invention provides a method for producing a therapeutic composition having mRNA that encode for an antigen from a human immunodeficiency virus, such as human immunodeficiency virus type 1 or human immunodeficiency virus type 2. In certain embodiments the present invention provides a method for producing a therapeutic composition having mRNA that encode for an antigen from a human metapneumovirus. In certain embodiments the present invention provides a method for producing a therapeutic composition having mRNA that encode for an antigen from a human parainfluenza virus, such as human parainfluenza virus type 1, human parainfluenza virus type 2, or human parainfluenza virus type 3. In certain embodiments the present invention provides a method for producing a therapeutic composition having mRNA that encode for an antigen from malaria virus. In certain embodiments the present invention provides a method for producing a therapeutic composition having mRNA that encode for an antigen from zika virus. In certain embodiments the present invention provides a method for producing a therapeutic composition having mRNA that encode for an antigen from chikungunya virus.

To facilitate expression of mRNA in vivo, compositions encapsulating mRNA can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Lyophilized composition of the present invention can be reconstituted with purified water for administration to a subject in need thereof. In certain embodiments, upon reconstitution with an appropriate rehydration media (e.g., purified water, deionized water, 5% dextrose (w/v), 10% trehalose (w/v) and/or normal saline, the reconstituted composition demonstrates pharmacological or biological activity comparable with that observed prior to lyophilization. In some embodiments, lyophilized compositions of the present invention can be reconstituted with a pH-buffered solution for administration to a subject in need thereof. In certain embodiments, upon reconstitution with an appropriately buffered solution, the reconstituted composition can comprise a desired pH. In some embodiments, lyophilized compositions of the present invention are reconstituted with a pH-buffered solution to yield a reconstituted composition having a pH of pH 5 to pH 8. In some embodiments, lyophilized compositions of the present invention are reconstituted with a pH-buffered solution to yield a reconstituted composition having a pH of pH 5.5 to pH 7.5. In some embodiments, lyophilized compositions of the present invention are reconstituted with a pH-buffered solution to yield a reconstituted composition having a pH of pH 6.0 to pH 7.0. In some embodiments, lyophilized compositions of the present invention are reconstituted with a pH-buffered solution to yield a reconstituted composition having a pH 6.0. In some embodiments, lyophilized compositions of the present invention are reconstituted with a pH-buffered solution to yield a reconstituted composition having a pH 6.5. In some embodiments, lyophilized compositions of the present invention are reconstituted with a pH-buffered solution to yield a reconstituted composition having a pH 6.8. In some embodiments, lyophilized compositions of the present invention are reconstituted with a pH-buffered solution to yield a reconstituted composition having a pH 7.0. In some embodiments, lyophilized compositions of the present invention are reconstituted with a pH-buffered solution to yield a reconstituted composition having a pH 7.2. In some embodiments, lyophilized compositions of the present invention are reconstituted with a pH-buffered solution to yield a reconstituted composition having a pH 7.5. In some embodiments, lyophilized compositions of the present invention are reconstituted with a pH-buffered solution to yield a reconstituted composition having a pH 7.7.

Provided mRNA-encapsulated within nanoparticles, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical, and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

The present invention provides methods of delivering mRNA encapsulated in lipid nanoparticles (mRNA-LNP) for in vivo protein production, comprising administering a composition comprising mRNA-LNP to a subject in need of delivery. In some embodiments, a composition comprising mRNA-LNP is administered via intravenous delivery, subcutaneous delivery, oral delivery, subdermal delivery, ocular delivery, intratracheal injection pulmonary delivery (e.g. nebulization), intramuscular delivery, intrathecal delivery, or intraarticular delivery.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

In some embodiments, a composition comprising mRNA-LNP is administered by intravenous delivery. In some embodiments, a composition comprising mRNA-LNP is administered by subcutaneous delivery. In some embodiments, a composition comprising mRNA-LNP is administered by oral delivery. In some embodiments, a composition comprising mRNA-LNP is administered by subdermal delivery. In some embodiments, a composition comprising mRNA-LNP is administered by ocular delivery. In some embodiments, a composition comprising mRNA-LNP is administered by intratracheal delivery. In some embodiments, a composition comprising mRNA-LNP is administered by pulmonary delivery. In some embodiments, a composition comprising mRNA-LNP is administered by nebulization delivery. In some embodiments, a composition comprising mRNA-LNP is administered by intramuscular delivery. In some embodiments, a composition comprising mRNA-LNP is administered by intrathecal delivery. In some embodiments, a composition comprising mRNA-LNP is administered by intraarticular delivery. In some embodiments, a composition comprising mRNA-LNP is administered by rectal delivery. In some embodiments, a composition comprising mRNA-LNP is administered by vaginal delivery. In some embodiments, a composition comprising mRNA-LNP is administered by transmucosal delivery. In some embodiments, a composition comprising mRNA-LNP is administered by intestinal delivery. In some embodiments, a composition comprising mRNA-LNP is administered by parental delivery. In some embodiments, a composition comprising mRNA-LNP is administered by intradermal delivery. In some embodiments, a composition comprising mRNA-LNP is administered by subcutaneous delivery. In some embodiments, a composition comprising mRNA-LNP is administered by intraventricular delivery. In some embodiments, a composition comprising mRNA-LNP is administered by intraperitoneal delivery. In some embodiments, a composition comprising mRNA-LNP is administered by intranasal delivery.

In some embodiments, the intramuscular administration is to a muscle selected from the group consisting of skeletal muscle, smooth muscle and cardiac muscle. In some embodiments, the administration results in delivery of the mRNA to a muscle cell. In some embodiments, the administration results in delivery of the mRNA to a hepatocyte (i.e., liver cell). In a particular embodiment, the intramuscular administration results in delivery of the mRNA to a muscle cell.

Additional teaching of pulmonary delivery and nebulization are described in published U.S. Application No. US 2018/0125989 and published U.S. Application No. US 2018/0333457, each of which is incorporated by reference in its entirety.

Alternatively or additionally, mRNA-loaded nanoparticles and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., mRNA) described herein. Therapeutic agents can be administered at regular intervals, depending on the nature, severity and extent of the subject's condition. In some embodiments, a therapeutically effective amount of the therapeutic agents (e.g., mRNA) of the present invention may be administered intrathecally periodically at regular intervals (e.g., once every year, once every six-months, once every five-months, once every three-months, bimonthly (once every two-months), monthly (once every month), biweekly (once every two-weeks), twice a month, once every 30-days, once every 28-days, once every 14-days, once every 10-days, once every 7-days, weekly, twice a week, daily, or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily, or every other day. In a preferred embodiment, the compositions of the present invention are administered to a subject twice a week, once a week, once every 7-days, once every 10-days, once every 14-days, once every 28-days, once every 30-days, once every two-weeks, once every three-weeks, or more-preferably once every four-weeks, once-a-month, twice-a-month, once every six-weeks, once every eight-weeks, once every other month, once every three-months, once every four-months, once every six-months, once every eight-months, once every nine-months, or annually. Also contemplated are compositions and liposomes that are formulated for depot administration (e.g., intramuscularly, subcutaneously, intravitreally) to either deliver or release therapeutic agent (e.g., mRNA) over extended periods of time. Preferably, the extended-release means employed are combined with modifications made to the mRNA to enhance stability.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating a disease or disorder). For example, a therapeutically effective amount may be an amount sufficient to achieve a desired therapeutic and/or prophylactic effect. Generally, the amount of a therapeutic agent (e.g., mRNA) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

Also contemplated herein are lyophilized pharmaceutical compositions that can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

In some embodiments, administering the provided composition results in an increased mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts) . In some embodiments, administering the provided composition results in an increased mRNA expression level by at least about 10%, 20%, 30%, 40%, 50%, 60%, 70%, 80%, 90%, or 95% as compared to the baseline level immediately before treatment. In some embodiments, administering the provided composition results in an increased mRNA expression level as compared to an mRNA expression level in subjects who are not treated According to various embodiments, the timing of expression of delivered mRNA can be tuned to suit a particular medical need. In some embodiments, the expression of the protein encoded by delivered mRNA is detectable 1, 2, 3, 6, 12, 24, 48, 72, and/or 96 hours after administration of provided liposomes and/or compositions. In some embodiments, the expression of the protein encoded by delivered mRNA is detectable one-week, two-weeks, and/or one-month after administration.

The present invention also provides delivering a composition having mRNA molecules encoding a peptide or polypeptide of interest for use in the treatment of a subject, e.g., a human subject or a cell of a human subject or a cell that is treated and delivered to a human subject.

EXAMPLES

While certain compounds, compositions and methods of the present invention have been described with specificity in accordance with certain embodiments, the following examples serve only to illustrate the invention and are not intended to limit the same.

Example 1. Lyophilization of mRNA with Ascorbic Acid

This example illustrates an exemplary lyophilization process of the present invention. This example shows that addition of ascorbic acid for lyophilization of lipid nanoparticles encapsulating mRNA (mRNA-LNP) increases the mRNA integrity of the lyophilized composition comprising mRNA-LNP after both short- and long-term storage. Furthermore, performing the secondary drying step at a higher temperature (e.g., 20° C.) also increased the stability of lyophilized composition, as determined by mRNA integrity over a period of time.

A solution containing in vitro synthesized CFTR mRNA encapsulated in lipid nanoparticle (mRNA-LNP) was buffer exchanged into an aqueous solution comprising lyoprotectant (e.g. 10% trehalose) with or without ascorbic acid at 10 mM, 20 mM, and 50 mM, as shown in Tables 1 and 2. For sample J (as shown in Tables 1 and 2), the mRNA-LNP formulation was pretreated by washing twice with buffer comprising 10 mM citrate (pH 7.0), 1 mM EDTA and 10% trehalose, followed by buffer exchange into 20 mM ascorbic acid in 10% trehalose. The mRNA-LNP formulation solutions were then subjected to a lyophilization process characterized by specific parameters for the freezing, primary drying, and secondary drying steps, as shown in FIG. 1, followed by reconstitution of the lyophilized mRNA-LNP composition. Notably, the secondary drying step was performed at a temperature of about 20'° C. Traditionally, for lyophilization of mRNA, secondary drying step is performed at 4° C. as mRNA is unstable and extremely sensitive to temperature. With the secondary drying step at a temperature of about 20° C., the moisture content of the lyophilized mRNA was about 0.5-1%, which is significantly less the 3-4% moisture content of the lyophilized sample with the traditional secondary drying condition.

Each sample of the lyophilized mRNA-LNP composition was stored at room temperature for four weeks and at 2-8° C. for 3 months. mRNA integrity of the lyophilized mRNA-LNP composition was determined by capillary electrophoresis (CE) at different time points as shown in the Tables 1 and 2.

TABLE 1 mRNA integrity of lyophilized sample stored at room temperature

| Sample | Lyophilization Condition: Secondary Drying Temperature | Lyophilization Condition: Ascorbic Acid | mRNA integrity after storage: 0 week | mRNA integrity after storage: 1 week | mRNA integrity after storage: 4 weeks |
|---|---|---|---|---|---|
| A | 20° C. | 0 mM | 59% | 37% | 14% |
| B | 20° C. | 0 mM | 64% | 42% | 17% |
| C | 4° C. | 0 mM | 43% | 21% | 4% |
| D | 4° C. | 0 mM | 55% | 13% | 1% |
| E | 4° C. | 0 mM | 69% | 15% | 2% |
| F | 20° C. | 50 mM | 59% | 47% | 36% |
| G | 20° C. | 20 mM | 58% | 44% | 30% |
| H | 20° C. | 20 mM | 58% | 46% | 29% |
| I | 20° C. | 10 mM | 59% | 49% | 32% |
| J | 20° C. | 20 mM | 55% | 47% | 30% |

Figure 2:
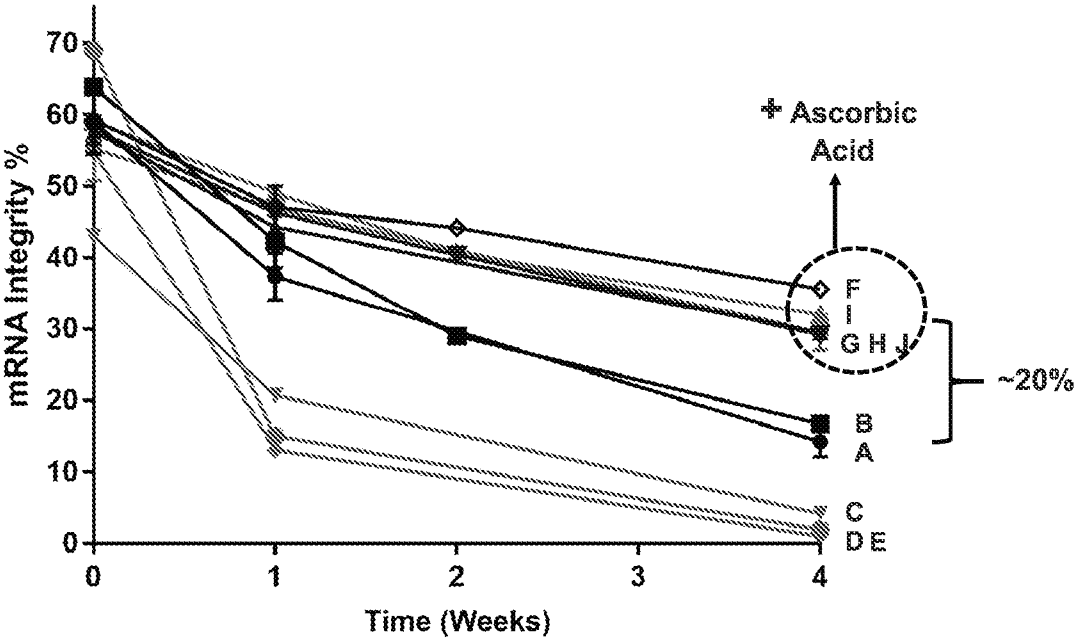
FIG. 2 depicts an exemplary graph showing mRNA integrity of lyophilized composition comprising mRNA encapsulated in lipid nanoparticles (mRNA-LNPs) over 4 weeks upon storage at room temperature. Notably, lyophilized mRNA samples with ascorbic acid have substantially high mRNA integrity as compared to samples without ascorbic acid.

As shown in Table 1 and FIG. 2, the addition of ascorbic acid for the lyophilization process prolonged mRNA integrity when stored at room temperature for both and 4 weeks. Notably, samples F-J, which contained various concentrations of ascorbic acid, had about 20% higher mRNA integrity after 4 weeks as compared to controls (samples A and B), which did not have any ascorbic acid.

Figure 3:
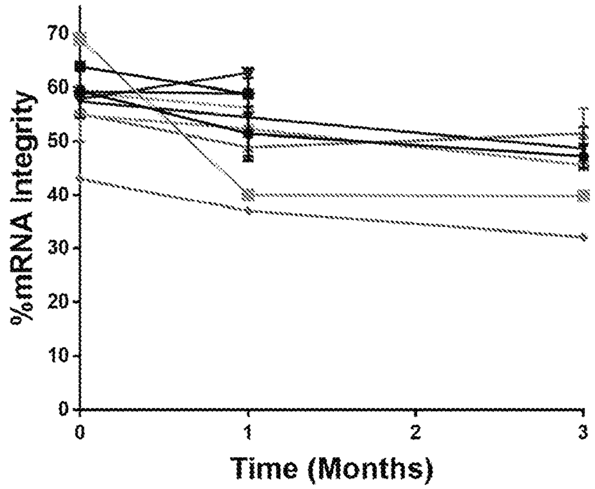
FIG. 3 depicts an exemplary graph and an accompanying table showing mRNA integrity of lyophilized composition comprising mRNA encapsulated in lipid nanoparticles (mRNA-LNPs) over 3 months upon storage at 2-8° C.

Furthermore, the addition of ascorbic acid for the lyophilization process maintained the mRNA integrity when stored at 2-8° C. for 3 months, as shown in Table 2 and FIG. 3. Samples A-B and F-J, which went through secondary drying step at 20° C. generally maintained higher mRNA integrity for long time, as compared to samples C-E, which went through a secondary drying step at 4° C.

TABLE 2 mRNA integrity of lyophilized sample stored at 2-8° C.

| Sample | Lyophilization Condition: Secondary Drying Temperature | Lyophilization Condition: Ascorbic Acid | mRNA integrity after storage: 0 month | mRNA integrity after storage: 1 month | mRNA integrity after storage: 3 months |
|---|---|---|---|---|---|
| A | 20° C. | 0 mM | 59 | 51 | 47 |
| B | 20° C. | 0 mM | 64 | 59 | |
| C | 4° C. | 0 mM | 43 | 37 | 32 |
| D | 4° C. | 0 mM | 55 | 52 | 46 |
| E | 4° C. | 0 mM | 69 | 40 | 40 |
| F | 20° C. | 50 mM | 59 | 59 | |
| G | 20° C. | 20 mM | 57 | 55 | 49 |
| H | 20° C. | 20 mM | 58 | 63 | |
| I | 20° C. | 10 mM | 59 | 56 | |
| J | 20° C. | 20 mM | 55 | 49 | 51 |

Overall, the data in this example show that the addition of ascorbic acid and performing secondary drying step at 20° C. for lyophilizing mRNA improve mRNA integrity for short- and long-term storage.

Example 2. mRNA Integrity of Lyophilized mRNA Encapsulated in LNP at Room Temperature and at 2-8° C.

This example further illustrates that the secondary drying step at high temperature (e.g., 20° C.) during the lyophilization process, the addition of ascorbic acid in the mRNA-LNP formulation, and pretreating the mRNA-LNP formulation with a buffer ("pretreatment") contribute to stability and integrity of lyophilized mRNA encapsulated in the lipid nanoparticle over a long period of time at room temperature and at 2-8° C.

A solution containing in vitro synthesized CFTR mRNA encapsulated in lipid nanoparticle (mRNA-LNP) was buffer exchanged into an aqueous solution comprising lyoprotectant (e.g. 10% trehalose) with or without 20 mM ascorbic acid, as shown in Table 3-4. For sample E (as shown in Tables 3 and 4), the mRNA-LNP formulation was pretreated by washing twice with buffer comprising 10 mM citrate (pH 7.0), 1 mM EDTA and 10% trehalose, followed by buffer exchange into 20 mM Ascorbic acid in 10% trehalose.

The solutions comprising mRNA-LNPs were then subjected to a lyophilization process as explained in Example 1, with different conditions as shown in Tables 3-4, followed by reconstitution of the lyophilized mRNA-LNP composition. Each sample of the lyophilized mRNA-LNP composition was stored at room temperature for four weeks and at 2-8° C. for 6 months. mRNA integrity of the lyophilized mRNA was determined by capillary electrophoresis (CE) at different time points as shown in the Tables 3 and 4.

TABLE 3 mRNA integrity of lyophilized sample stored at room temperature

| Sample | Lyophilization Condition: Secondary Drying Temperature | Ascorbic Acid | Pretreatment | mRNA integrity after storage at RT (%): 0 week | 1 week | 4 weeks | Drop in mRNA integrity post 1 week storage |
|---|---|---|---|---|---|---|---|
| A | 4° C. | 0 mM | No | 55 | 13 | 14 | 42 |
| B | 4° C. | 0 mM | No | 69 | 15 | 2 | 54 |
| C | 20° C. | 0 mM | No | 59 | 37 | 14 | 22 |
| D | 20° C. | 20 mM | No | 58 | 44 | 30 | 14 |
| E | 20° C. | 20 mM | Yes | 55 | 47 | 30 | 8 |

TABLE 4 mRNA integrity of lyophilized sample stored at 2-8° C.

| Sample | Lyophilization Condition: Secondary Drying Temperature | Ascorbic Acid | Pretreatment | mRNA integrity after storage at RT (%): 0 month | 3 months | 6 months | Drop in mRNA integrity post 6 months storage |
|---|---|---|---|---|---|---|---|
| A | 4° C. | 0 mM | No | 69 | 40 | 43 | 26 |
| C | 20° C. | 0 mM | No | 59 (±5) | 47 (±2) | 45 (±1) | 14 |
| D | 20° C. | 20 mM | No | 58 (±2) | 47 (±4) | 46 | 12 |
| E | 20° C. | 20 mM | Yes | 55 (±5) | 50 (±5) | 47 (±0.3) | 8 |

Figure 4:
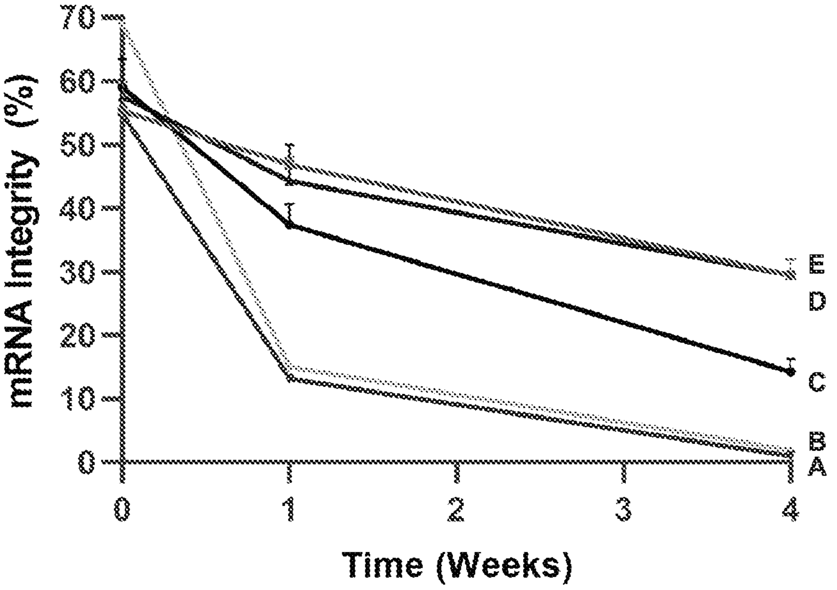
FIG. 4 depicts an exemplary graph showing mRNA integrity of lyophilized composition comprising mRNA encapsulated in lipid nanoparticles (mRNA-LNPs) over 4 weeks upon storage at room temperature.

As shown in Table 3 and FIG. 4, each of the lyophilization conditions—1) the secondary drying step at 20° C., 2) the addition of ascorbic acid, and 3) pretreatment step—prolonged mRNA integrity when stored at room temperature for both 1 and 4 weeks. Notably, samples C-E, which were lyophilized with a secondary drying step at 20° C. had significantly smaller drop in mRNA integrity after 4 weeks, as compared to samples A-B, which were lyophilized with a secondary drying step at 4'° C. Furthermore, the addition of ascorbic acid to the mRNA-LNP formulation prior to lyophilization significantly helped in maintaining the mRNA integrity of the lyophilized composition at room temperature. The pretreatment step also further prolonged mRNA integrity as shown by significantly smaller drop in mRNA integrity after 1-week and 4-week storage at room temperature (sample E).

Figure 5:
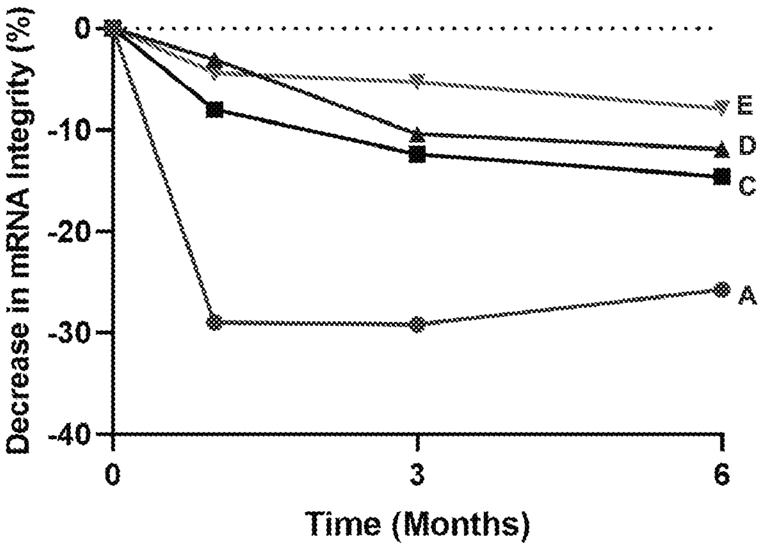
FIG. 5 depicts an exemplary graph showing mRNA integrity of lyophilized composition comprising mRNA encapsulated in lipid nanoparticles (mRNA-LNPs) over 6 months upon storage at 2-8° C.

The same trend was observed when the samples were stored at 2-8° C., as shown in Table 4 and FIG. 5. Drop in mRNA integrity after 6-month storage at 2-8° C. of sample E was about 6 fold lower than sample A (Table 5), illustrating that the lyophilization conditions of the present invention can significantly prolong the mRNA integrity of lyophilized mRNA-LNP composition.

TABLE 5

Decrease in mRNA integrity of lyophilized sample stored at 2-8° C. over a period of time

| Sample | Lyophilization Condition: Secondary Drying Temperature | Ascorbic Acid | Pretreatment | Drop in mRNA integrity at each time point as compared to 0 time point: 0 month | 1 month | 3 months | 6 months |
|---|---|---|---|---|---|---|---|
| A | 4° C. | 0 mM | No | 0 | 29 | 29 | 26 |
| C | 20° C. | 0 mM | No | 0 | 8 | 12 | 14 |
| D | 20° C. | 20 mM | No | 0 | 3 | 11 | 12 |
| E | 20° C. | 20 mM | Yes | 0 | 4 | 5 | 8 |

Overall, this example shows that each of the lyophilization conditions of the present invention—1) the secondary drying step at 20° C., 2) the addition of ascorbic acid, and 3) pretreatment step—can individually and collectively prolong the mRNA integrity of lyophilized mRNA-LNP composition for both short-term and long-term storage.

Example 3. Ascorbic Acid Addition Contributes to Improvement of mRNA Integrity During Lyophilization of mRNA-LNP This example examines whether the low pH or the pretreatment with ascorbic acid can improve mRNA integrity as shown in Examples 2-3.

Various samples comprising mRNA-LNPs were prepared for lyophilization as shown in Table 6. For sample A, solution containing in vitro synthesized mRNA encapsulated in lipid nanoparticle (mRNA-LNP) was buffer exchanged into 10% trehalose. For sample B, the mRNA-LNP formulation was pretreated by washing twice with buffer comprising 20 mM ascorbic acid in 10% trehalose, followed by buffer exchange into 10% trehalose. For sample C, the mRNA-LNP formulation was buffer exchanged into a buffer comprising pH of 3.0 and 10% trehalose. Buffer with pH 3.0 was prepared with 1N HCl. For sample D, mRNA-LNP formulation was buffer exchanged into 10% trehalose with 20 mM ascorbic acid.

Samples A-D, each comprising mRNA-LNPs, were then subjected to a lyophilization process as explained in Example 1 with a secondary drying step at 20° C., followed by reconstitution of the lyophilized mRNA-LNP composition. Each lyophilized mRNA-LNP sample was stored at room temperature for four weeks and mRNA integrity was determined by capillary electrophoresis (CE) at different time points as shown in the Table 6.

TABLE 6 mRNA integrity of lyophilized sample stored at room temperature

| Sample | Condition | mRNA integrity after storage at RT (%) | | |
|---|---|---|---|---|
| | | 0 week | 2 weeks | 4 weeks |
| A | Control | 62 | 22 | 15 |
| B | Pretreatment with ascorbic acid | 62 | 32 | 19 |
| C | Formulation with low pH (pH 3) | 62 | 33 | 21 |
| D | 20 mM ascorbic acid | 58 | 41 | 30 |

Figure 6:
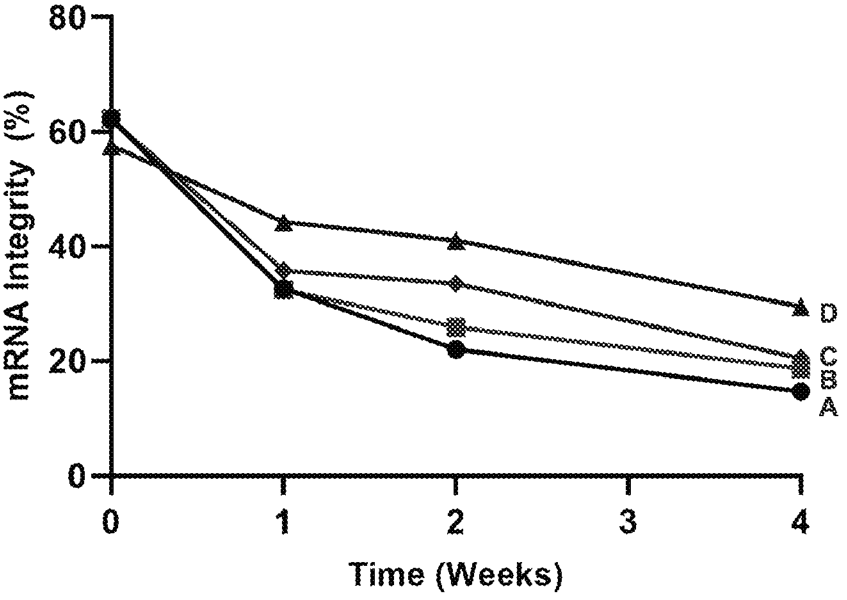
FIG. 6 depicts an exemplary graph showing mRNA integrity of various lyophilized composition comprising mRNA encapsulated in lipid nanoparticles (mRNA-LNPs) over 4 weeks upon storage at room temperature.

As shown in Table 6 and FIG. 6, low pH formulation (sample C) and pretreatment with ascorbic acid (sample D) were not as effective in prolonging mRNA integrity of mRNA-LNP compared to sample D, which had 20 mM ascorbic acid.

Example 4. Effect of Ascorbic Acid at Various Concentrations

This example explores the effect of ascorbic acid concentrations on mRNA integrity of mRNA-LNP compositions post lyophilization and reconstitution.

A solution containing mRNA-LNP was buffer exchanged into an aqueous solution comprising lyoprotectant (e.g. 10% trehalose) with or without ascorbic acid at 3 mM, 5 mM, 10 mM, 20 mM, and 50 mM as shown in Table 7. Then, the solutions comprising mRNA-LNPs were then subjected to a lyophilization process as explained in Example 1, with a secondary drying step at 20° C., followed by reconstitution of the lyophilized mRNA-LNP composition. The lyophilized mRNA-LNP composition was stored at room temperature for four weeks, and mRNA integrity was determined by capillary electrophoresis (CE) at different time points as shown in the Table 7.

TABLE 7

Decrease in mRNA integrity of lyophilized sample stored at 2-8° C. over a period of time

| Sample | Lyophilization Condition | | mRNA integrity (%) | | |
|---|---|---|---|---|---|
| | Ascorbic Acid (mM) | pH | 0 week | 2 weeks | 4 weeks |
| A | 0 | 4.6 | 64 | 29 | 17 |
| B | 3 | | 60 | 32 | NA |
| C | 5 | | 57 | 39 | 25 |
| D | 10 | 3.4 | 60 | 41 | 32 |
| E | 20 | 3.3 | 58 | 40 | 29 |
| F | 50 | 2.9 | 59 | 44 | 36 |

Figure 7:
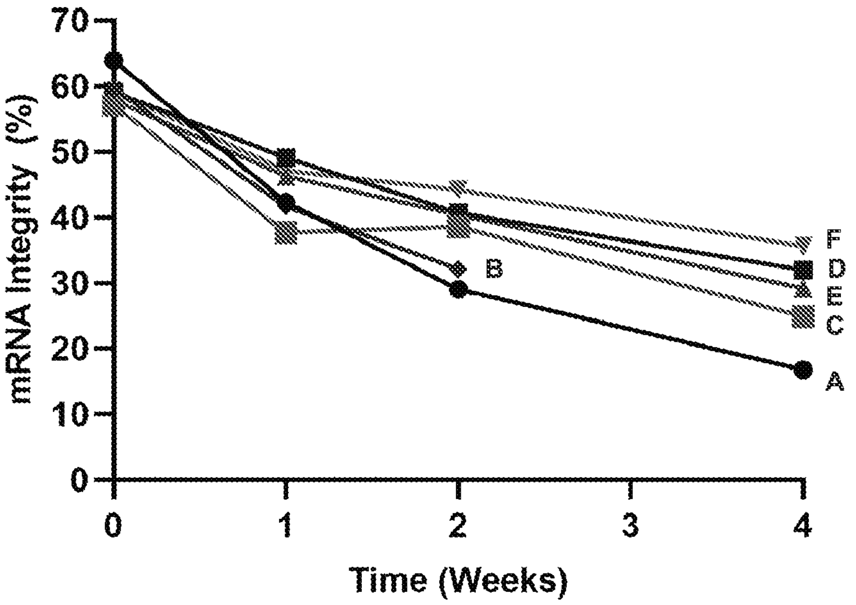
FIG. 7 depicts an exemplary graph showing mRNA integrity of lyophilized composition comprising mRNA encapsulated in lipid nanoparticles (mRNA-LNPs), prepared with various concentrations of ascorbic acid, over 4 weeks upon storage at room temperature.

As shown in Table 7 and FIG. 7, addition of ascorbic acid to mRNA-LNP composition at a concentration of above or at 10 mM prior to lyophilization was effective in prolonging mRNA integrity. Over the 4-week storage at room temperature, a drop in mRNA integrity of the lyophilized mRNA-LNP composition was significantly lower when ascorbic acid was added at or above 10 mM (samples D-F in Table 7).

Addition of ascorbic acid lowers pH of the mRNA-LNP composition to about 2.9-3.4 as shown in Table 7. However for in vivo study or for clinical purposes, it is beneficial to have the pH of the mRNA-LNP composition to be near the physiological pH. To increase the pH of the mRNA-LNP composition lyophilized with ascorbic acid, different buffers were added to the mRNA-LNP composition at various concentrations and the pH was measured.

TABLE 8

Adjustment of pH post-lyophilization with ascorbic acid

| Buffer | Buffer Concentration (mM) | Ascorbic Acid Concentration (mM) added prior to lyophilization process | Final pH |
|---|---|---|---|
| Tris pH 7.5 | 75 | 20 | 4.8 |
| | 100 | 20 | 6.9 |
| Tris pH 8.0 | 20 | 20 | 4.2 |
| | 50 | 20 | 6.9 |
| Phosphate pH 7.0 | 10 | 10 | 4.8 |
| | 20 | 10 | 6.3 |
| | 50 | 20 | 4.7 |
| | 60 | 20 | 6.2 |
| | 50 | 50 | 3.9 |
| | 75 | 50 | 4.2 |

Table 8 shows that for samples that were added with 10 mM or 20 mM ascorbic acid prior to the lyophilization process, the pH of the mRNA-LNP composition could be increased by addition of various buffers. However, the pH of the samples that were added with 50 nM ascorbic acid prior to the lyophilization remained around 4 even when high concentration (e.g., 50 mM and 75 mM) of the buffer was added to the samples.

Example 5. Formulation Characteristics Pre- and Post-Lyophilization

This example shows that the overall integrity of mRNA encapsulated LNPs (mRNA-LNPs) is well maintained post-lyophilization process, and that addition of ascorbic acid does not adversely affect integrity of lipid nanoparticles encapsulating mRNA, as demonstrated by size, polydispersity index (PDI) and encapsulation efficiency.

A solution containing in vitro synthesized mRNA encapsulated in lipid nanoparticle (mRNA-LNP) was buffer exchanged into an aqueous solution comprising lyoprotectant (e.g. 10% trehalose) with or without 10 mM, 20 mM, and 30 mM ascorbic acid, as shown in Table 9. The solutions comprising mRNA-LNPs were then subjected to a lyophilization process as explained in Example 1, with a secondary drying step at 20° C., followed by reconstitution of the lyophilized mRNA-LNP composition. Size, PDI, and encapsulation efficiency of mRNA-LNPs were measured pre- and post-lyophilization/reconstitution for samples shown in Table 9.

TABLE 9

Characteristics of mRNA-LNPs pre- and post-lyophilization process

| | | Size (mM) | | PDI | | Encapsulation Efficiency (%) | |
|---|---|---|---|---|---|---|---|
| Sample | Ascorbic Acid | Pre-lyo | Post-lyo | Pre-lyo | Post-lyo | Pre-lyo | Post-lyo |
| A | 0 mM | 50 | 53 | 0.134 | 0.163 | 87 | 88 |
| B | 10 mM | 52 | 52 | 0.140 | 0.165 | 87 | 82 |
| C | 20 mM | 52 | 52 | 0.151 | 0.176 | 87 | 84 |
| D | 30 mM | 53 | 53 | 0.155 | 0.140 | 84 | 84 |

As shown in Table 9, size, PDI, and encapsulation efficiency of mRNA-LNPs were maintained after the mRNA-LNPs have gone through the lyophilization process of the present invention. This data shows that the lyophilization conditions and process of the present invention are effective in prolonging the integrity of mRNA encapsulated into LNPS while also preserving the size, PDI, and encapsulation efficiency of the mRNA-LNPs post-lyophilization.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of preparing a stable lyophilized composition comprising a lipid nanoparticle encapsulating mRNA, the method comprising the steps of:

adding between 5 mM and 200 mM of ascorbic acid to an aqueous solution comprising the lipid nanoparticle encapsulating mRNA having an initial mRNA integrity, freezing the aqueous solution to obtain a frozen solution, and drying the frozen solution for a period of greater than 10 hours to obtain the stable lyophilized composition, wherein:

the step of drying the frozen solution comprises a primary drying phase and a secondary drying phase;

the primary drying phase is performed at a first temperature between 0° C. and −100° C.;

the secondary drying phase is performed at a second temperature between 5° C. and 40° C.;

the primary drying phase and/or the secondary drying phase is performed at a pressure of between 10 mTorr and 80 mTorr;

the stable lyophilized composition has a moisture content of less than 1% after the secondary drying phase; and upon reconstitution of the stable lyophilized composition following storage of the stable lyophilized composition for four weeks at a temperature of 15° C. to 25° C., an mRNA integrity following reconstitution is at least 50% of the initial mRNA integrity.

2. The method of claim 1, wherein the method further comprises a step of removing citric acid from the aqueous solution prior to the step of adding between 5 mM and 200 mM of the ascorbic acid to the aqueous solution.

3. The method of claim 2, wherein the step of removing the citric acid from the aqueous solution comprises washing the aqueous solution with a citrate buffer comprising EDTA in which the buffer has a pH of 6 to 8.

4. The method of claim 3, wherein the citrate buffer is between 1 mM to 10 mM.

5. The method of claim 1, wherein the second temperature is between 15° C. to 30° C.

6. The method of claim 1, wherein the aqueous solution comprises about 10 mM to 50 mM of the ascorbic acid.

7. The method of claim 1, wherein the initial mRNA integrity is higher than 50%.

8. The method of claim 1, wherein the primary drying phase and the secondary drying phase are each performed at a pressure of between 10 mTorr and 80 mTorr.

9. The method of claim 8, wherein the primary drying phase and the secondary drying phase are each performed at a pressure of between 20 mTorr and 60 mTorr.

10. The method of claim 1, wherein the aqueous solution further comprises trehalose or sucrose.

11. A stable lyophilized composition comprising a lipid nanoparticle encapsulating mRNA and between 10 mM and 200 mM of ascorbic acid, wherein:

the stable lyophilized composition has a moisture content of less than 1%; and upon reconstitution of the stable lyophilized composition following storage of the stable lyophilized composition for four weeks at a temperature of 15° C. to 25° C., an integrity of the mRNA following reconstitution is at least 50% of an initial mRNA integrity.

12. The stable lyophilized composition of claim 11, wherein the stable lyophilized composition has less than 0.1 mM citrate.

13. The stable lyophilized composition of claim 11, wherein the stable lyophilized composition comprises between 10 mM and 50 mM of the ascorbic acid.

14. The stable lyophilized composition of claim 11, wherein the initial mRNA integrity is higher than 50%.

15. The stable lyophilized composition of claim 11, wherein the stable lyophilized composition comprises trehalose or sucrose.

16. The stable lyophilized composition of claim 11, wherein the stable lyophilized composition has a pH below 7.0.

17. The stable lyophilized composition of claim 11, wherein the lipid nanoparticle comprises a cationic lipid, a helper lipid and a PEG-modified lipid.

18. The stable lyophilized composition of claim 17, wherein the lipid nanoparticle further comprises cholesterol.

19. The stable lyophilized composition of claim 17, wherein the helper lipid is DOPE or DEPE.

20. The stable lyophilized composition of claim 17, wherein the PEG-modified lipid is DMG-PEG 2000.

* * * * *